(12) United States Patent
Ibragimova et al.

(10) Patent No.: US 11,415,653 B2
(45) Date of Patent: Aug. 16, 2022

(54) METHOD AND A DEVICE FOR DETECTING SUBSTANCES AND THEIR CONCENTRATIONS IN A MIXTURE USING MAGNETIC RESONANCE

(71) Applicants: Olena Ibragimova, Ottweiler-Fuerth (DE); Ilgiz Ibragimov, Ottweiler-Fuerth (DE)

(72) Inventors: Olena Ibragimova, Ottweiler-Fuerth (DE); Ilgiz Ibragimov, Ottweiler-Fuerth (DE)

(73) Assignee: Elegant Mathematics LLC, Sheridan, WY (US)

( * ) Notice: Subject to any disclaimer, the term of this patent is extended or adjusted under 35 U.S.C. 154(b) by 316 days.

(21) Appl. No.: 16/695,200

(22) Filed: Nov. 26, 2019

(65) Prior Publication Data

US 2020/0166592 A1     May 28, 2020

Related U.S. Application Data

(60) Provisional application No. 62/939,647, filed on Nov. 24, 2019, provisional application No. 62/772,003, filed on Nov. 27, 2018.

(51) Int. Cl.
*G01R 33/465*     (2006.01)
*G01N 15/06*     (2006.01)

(52) U.S. Cl.
CPC ....... *G01R 33/465* (2013.01); *G01N 15/0656* (2013.01)

(58) Field of Classification Search
USPC ........................................................ 324/309
See application file for complete search history.

(56) References Cited

U.S. PATENT DOCUMENTS

2007/0184455 A1\*   8/2007   Arrowsmith ......... G01N 24/088
                                                             435/6.12
2018/0340997 A1\*   11/2018   Ibragimova ............ G01R 33/32

\* cited by examiner

*Primary Examiner* — Rodney E Fuller
(74) *Attorney, Agent, or Firm* — Elegant Mathematics LLC

(57) ABSTRACT

A method and a device for detecting substances and their concentrations in a mixture using magnetic resonance, containing one or more markers deposited on a surface of a carrier in contact with the mixture, wherein the marker is a substance that through intermolecular interactions causes a predetermined orientation of molecules for at least one of the mixture components.

41 Claims, 22 Drawing Sheets

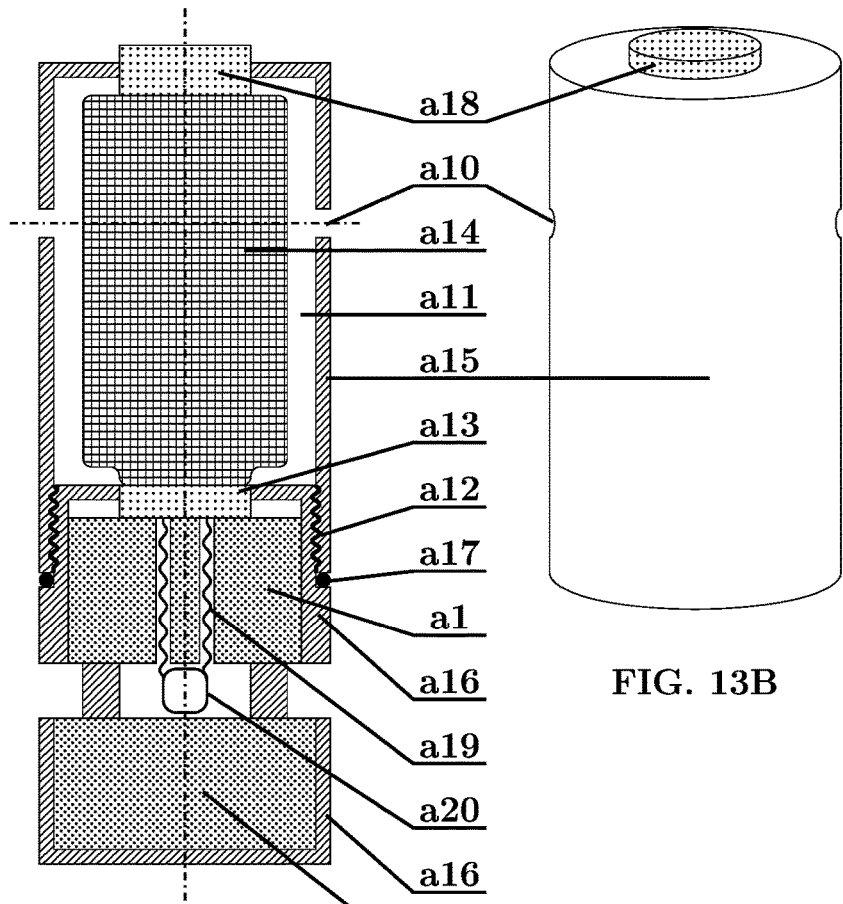
FIG. 13A
FIG. 13B
FIG. 13E
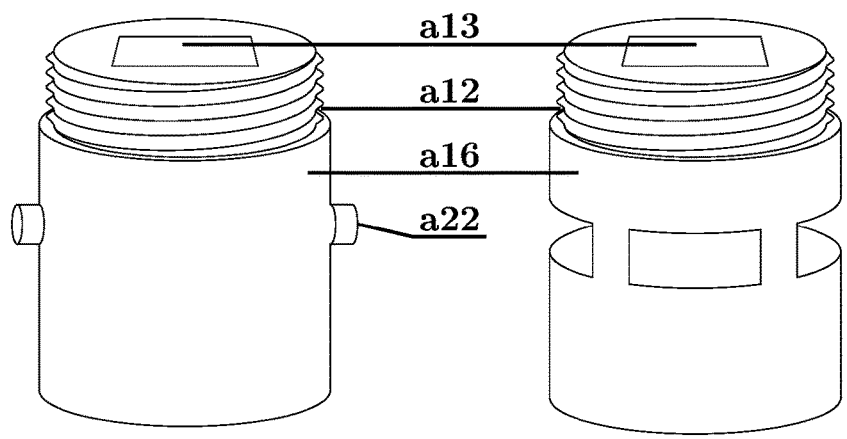
FIG. 13C
FIG. 13D

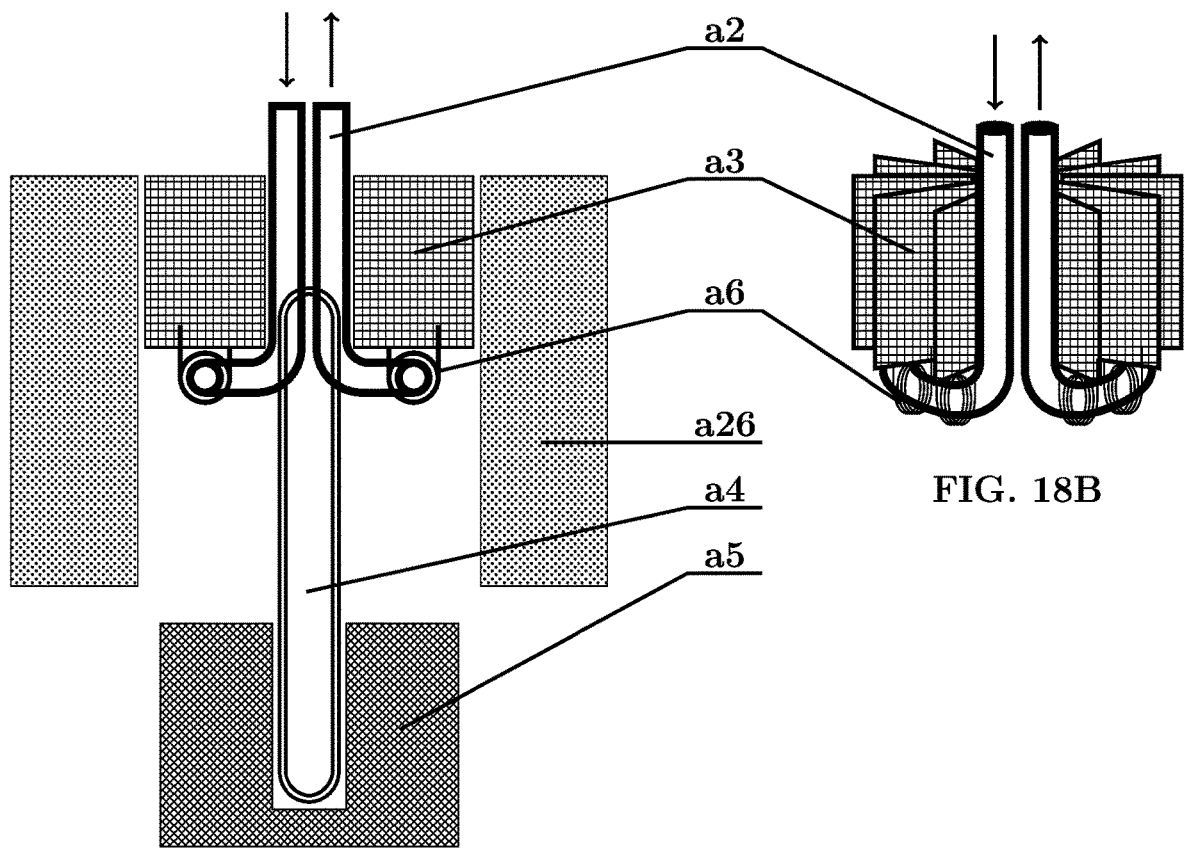
FIG. 18A
FIG. 18B
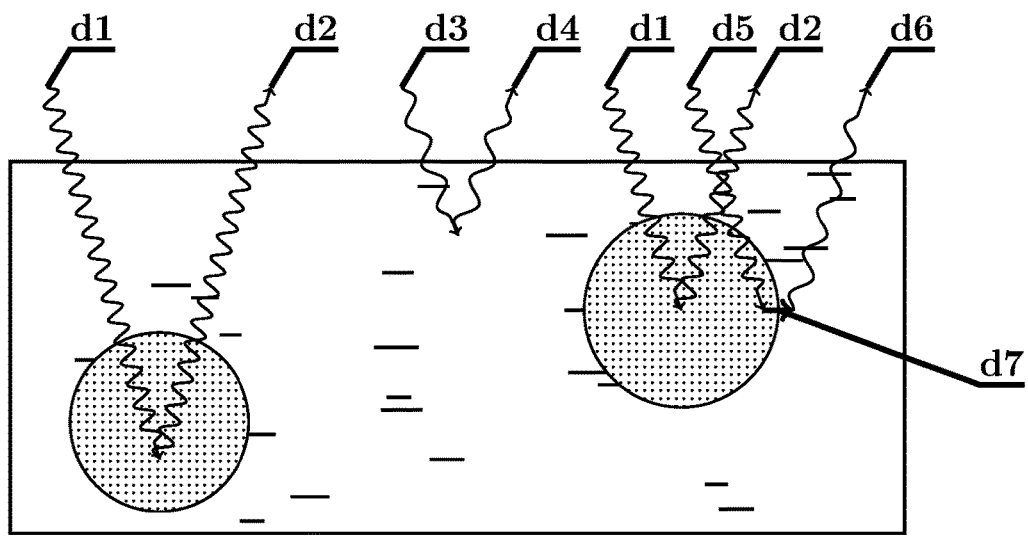
FIG. 19.

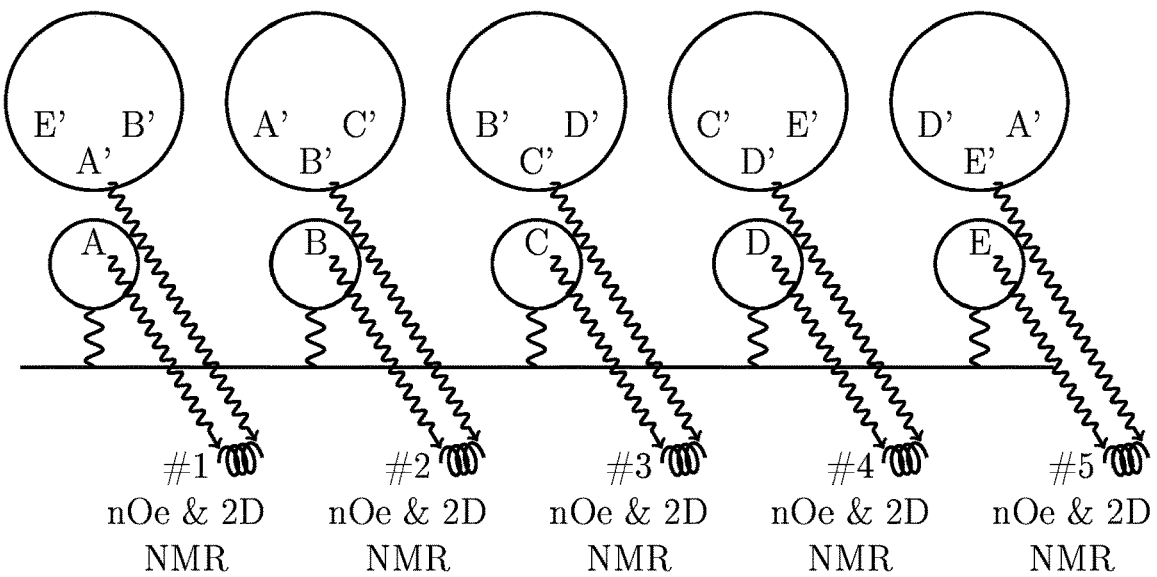
FIG. 32.
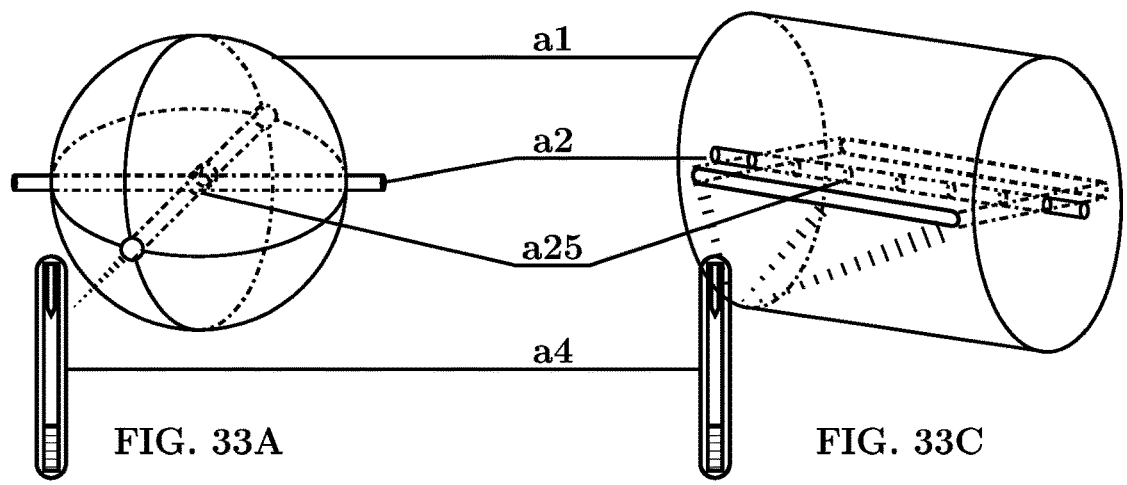
FIG. 33A
FIG. 33C
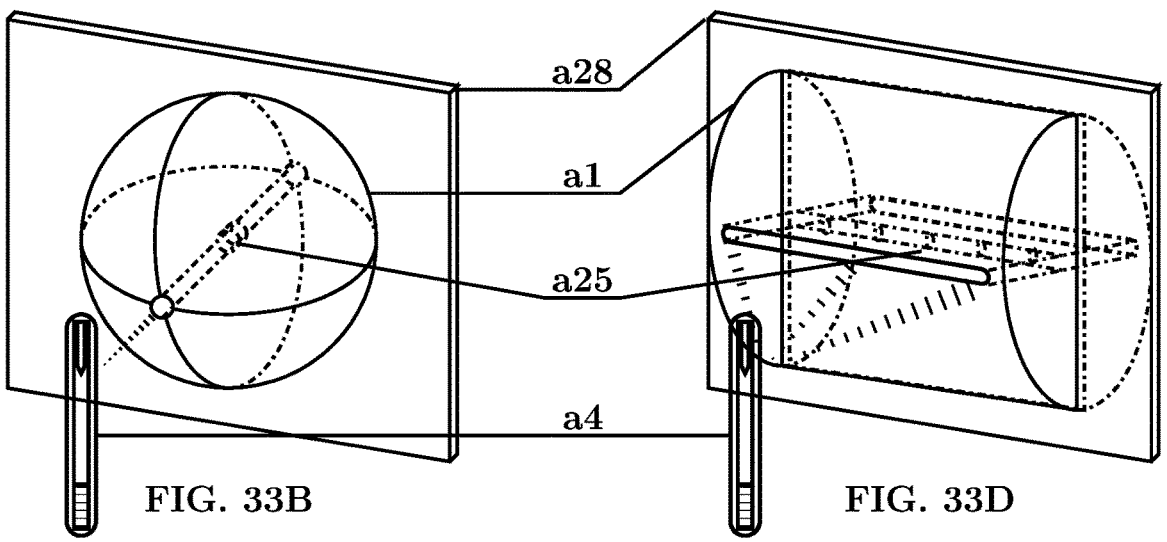
FIG. 33B
FIG. 33D

METHOD AND A DEVICE FOR DETECTING SUBSTANCES AND THEIR CONCENTRATIONS IN A MIXTURE USING MAGNETIC RESONANCE

CROSS-REFERENCE TO RELATED APPLICATIONS

This application claims the benefit under 35 U.S.C. § 119(e) of the priority of the following U.S. Provisional Applications: 62/772,003 filed on Nov. 27, 2018, and 62/939,647 filed on Nov. 24, 2019 by the present inventors.

TECHNICAL FIELD

This invention pertains to the field of nuclear magnetic resonance (NMR) spectroscopic and magnetic resonance imaging (MRI) techniques in real-time chemical analysis, imaging diagnostics, and the development of devices for non-invasive heating and ablation with real-time guidance and unsupervised and/or semi-supervised capabilities.

BACKGROUND OF THE INVENTION

The following list of some prior art that presently appears relevant:
U.S. Pat. Nos. 6,396,274 B1, 7,312,611 B1, 6,614,228 B2, 6,942,793 B2, 7,135,865 B2, 7,145,340 B2, 7,661,295 B2, 8,035,388 B2, 8,148,988 B2, 8,431,340 B2, 8,512,538 B2, 8,816,684 B2, 9,024,635 B2, 9,470,664 B2, 9,547,057 B2, 9,607,740 B2, U.S. Ser. No. 10/249,065 B2, U.S. Ser. No. 10/330,755 B2, U.S. Pat. Nos. 1,862,559 A, 2,442,762 A, 2,545,994 A, 2,993,638 A, 3,676,791 A, 4,075,042 A, 4,342,608 A, 4,415,959 A, 4,893,082 A, 5,247,935 A, 5,283,036 A, 5,847,564 A, 5,867,026 A, U.S. Ser. No. 12/153,349 A1, U.S. Ser. No. 13/164,495 A1, U.S. Ser. No. 13/397,273 A1, U.S. Ser. No. 14/394,976 A1, US 20150302579 A1, US 20160232175 A1, US 20070023639 A1, WO 2010112137 A1.

All chemical elements are composed of one or more isotopes. Every isotope is either a zero-spin isotope or a non-zero-spin isotope.

Nuclear magnetic resonance (NMR) is a physical phenomenon in which non-zero-spin isotopes absorb and re-emit electromagnetic radiation (energy) when placed in an external magnetic field.

NMR occurs at a specific resonance frequency; this frequency has a linear relationship with the strength of the permanent magnetic field and the magnetic properties of isotopes in the target field. Resonance occurs when the absorbed alternate magnetic field is transmitted orthogonally in the direction of the permanent magnetic field.

NMR spectrometers and magnetic resonance imaging (MRI) devices generally comprise one or more magnets that produce a strong magnetic field within a test region. These magnets are usually superconducting magnets, thus NMR applications are restricted to laboratory environments. Currently, anisotropic permanent magnets, i.e. having all parts magnetized in one direction, can achieve magnetic fields of only 1.5 T in strength compared to the 23 T of superconductor magnets. The NMR signal response grows quadratically with regard to the magnetic field strength used in the experiment, which highly constrains the sensitivity and informativity of spectra produced by NMR spectrometers and/or MRI devices that have permanent magnets. NMR devices with permanent magnets are often referred to as low-field NMR spectrometers.

When permanent magnets are combined with several other parts having appropriate magnetization, it is possible to build a focused magnetic field of greater strength than the maximal field achievable with the permanent magnet alone. One well-known combination is the Halbach structure, introduced by Klaus Halbach in 1980, which makes a 5 T magnetic field possible with permanent magnets. This structure is often used in NMR spectrometers; however, it requires joining an enormous number of magnetized pieces. Doing so may be commercially ineffective, or unreasonably sophisticated when using magnets of small size. The second problem characteristic of the Halbach structure is the high instability of the generated magnetic field in terms of both time and temperature if the same material is used throughout. U.S. Pat. No. 8,148,988 describes a Halbach system that compensates for this drawback through using several permanent magnets of different materials, albeit it only obtains almost half of the maximally achievable magnetic field strength.

Halbach structures may be roughly classified as follows: 1D—linear, 2D—cylindrical, and 3D-spherical. The maximal achievable magnetic field strength for 1D structures—is 2B, for 2D—is B $\log(R_o/R_i)$, and for 3D is $(4/3)B \log(R_o/R_i)$, where B is the maximum achievable magnetic field for an anisotropic structure and $R_o$ and $R_i$ are the outer and inner radiuses of cylinders and/or spheres. This shows that 3D structures deliver the highest possible magnetic field: they are superior to 2D by a factor of 4/3, which increases sensitivity by almost a factor of 2!

At the same time, 3D structures require joining an enormous number of magnetized pieces, compared to 2D and 1D structures. They may be almost impossible to build in the case of small-sized, portable magnets, or they may not achieve the desired magnetic field because the process of gluing and joining reduces magnetic field strength.

In addition, one of the biggest disadvantages of low-field NMR spectrometers is the high fluctuation of their magnetic fields. If the magnets are small (of a size appropriate to a portable device), the intensity and direction of the external magnetic field may be adversely affected. Even turning a 1.5 T NMR spectrometer to an angle about six degrees perpendicular to the Earth's magnetic force lines will ruin any measurements, and the device will have to be recalibrated. Even a slight movement of the table on which a spectrometer is placed may significantly disturb the spectra generated. Another related difficulty is that currently available spectrometers usually require high temperature stability (of the order of 0.01° C.), which is incompatible with chemical production equipment and in-situ measurements in chemical reactions.

There are two well-known and widely-used primary approaches that improve the sensitivity of NMR measurements: multi-nuclear and multi-dimensional spectra acquisition and dynamic nuclear polarization (DNP).

The acquisition of multi-nuclear spectra usually requires one receiver coil for each type of nucleus and/or calibration of each spectrum to internal standards; this requirement makes it impractical to fit currently available NMR spectrometers into smaller, portable devices.

The DNP method polarizes the spins of electrons in molecules. The normally random spins of the many electrons situated around the nuclei being investigated blur the nuclei's response. DNP forces all electron spins to point in the same direction, enhancing the NMR response from non-zero-spin isotopes. This well-known, widely-established method was first developed by Overhauser and Carver in 1953, but at that time, it had limited applicability for high-frequency, high-field NMR spectroscopy due to the lack of microwave (or gigahertz) signal generators. The requisite generators, called gyrotrons, are available today as turn-key instruments, and this has rendered DNP a valuable and indispensable method, especially in determining the structures of various molecules by high-resolution NMR spectroscopy. However, gyrotrons remain cost-prohibitive because they require expensive components, i.e. high-voltage generators, independent permanent magnetic field generators, and deep vacuum devices such as turbomolecular pumps.

Currently, chemical analysis, particularly portable and benchtop analysis, is usually associated with chromatography devices. Chromatography is a laboratory technique for the separation of a mixture. The mixture is dissolved in a fluid called the mobile phase, which carries it through a structure holding another material called the stationary phase. The various constituents of the mixture have different partition coefficients and thus travel at different speeds, causing them to separate. Separated components are then flowed past a detector that is usually based on either conductivity or optical (UV, IR) absorption measurements. In some very rare cases, NMR may be used as detector or in parallel with a standard optical detector, but this is very restricted in application due to high equipment costs.

Chromatography has better sensitivity than NMR, but is less informative as the response of a chromatograph comprises only a retention time; no additional information about chemical composition is available. If the substance(s) in the mixture are unknown and need to be characterized, one must perform many different measurements, most likely with different chromatography columns and mobile phases, to conclusively identify the components.

In contrast, if NMR analysis is performed on one unknown substance, then a multi-dimensional NMR spectrum usually is sufficient to get all the information necessary for its identification, including not only its atomic composition but also the real spatial distribution of atoms in the molecule.

The straightforward combination of chromatography for separation with currently available NMR spectrometers for characterization is hindered by the inherent flaws of both methods: separation on a chromatographic column usually takes long periods of time (hours), and there is almost no control over how components separate; furthermore, the separated components are then flowed over the detector, remaining situated in the detector for only a few seconds (or even milliseconds). The vast majority of the time, the detector is filled with a known substance—the mobile phase. NMR detection itself requires a long time, usually hours, so that said straightforward combination of chromatography for separation with currently available NMR spectrometers requires slowing down the flow speed by several orders. These measurements occur on a timescale of several days or even weeks that is unrealistic in regards to commercial applications.

Taken together, prospective inventors of a portable NMR spectrometer for industrial environments and/or MRI devices must overcome the following problems:

construct a signal acquisition scheme that is stable despite fluctuations of the permanent magnetic field and/or of the signal generator, or that can work without a signal generator;

use NMR to detect all (or most) visible, non-zero-spin isotopes that are present in the investigated area;

construct a new device as a DNP polarizer that does not require high voltage generators, expensive deep vacuum devices such as turbomolecular pumps with size constrains, that that preferably use the same permanent magnetic field as the NMR transmitters;

construct compact magnets with Halbach or Halbach-like structures that have better magnetic field strengths and are resistant to large temperature range;

find an appropriate solution for using chromatography in conjunction with NMR to leverage the advantages of both methods.

Usage of fully non-invasive methods in medical applications requires non-invasive methods for the detection of targeted regions (mainly tumors) and their precise positions within the broader area of detection (typically the patient's body).

There are several well-known and widely-used primary approaches that support surgeons in the detection of tumors and their precise positions within the body, i.e. biopsy, ultrasound monitoring, positron emission tomography (PET), X-ray computed tomography (CT), and MRI.

Each of these alternative ablation technologies has material disadvantages, so that prospective inventors of real-time visualization and surgical ablation methods must overcome the following problems:

construct a signal acquisition scheme that delivers real-time imaging;

construct an MRI system that allows the focusing of a magnetic field, AMF, or both at a predetermined region inside a body with real-time control of this position;

reduce equipment costs by constructing a new device as a DNP polarizer that does not require high voltage generators and expensive deep vacuum devices such as turbomolecular pumps;

construct compact magnets with Halbach structure to improve magnetic field strength.

SUMMARY

The invention is comprised of the following technological components:

1. Enhanced multi-nucLEar Generation, Acquisition, and Numerical Treatment of Nuclear Magnetic Resonance spectra (ELEGANT NMR) is a processing method for signal transformation that delivers real-time intermediate data, is stable to carrier frequency fluctuations, and in the particular case of NMR/MRI applications is also stable to magnetic field fluctuations.

2. Real-time method for processing signals from a repeating processing method.

3. Electron Larmor Microwave Amplifier THReaded On Nuclei (ELMATHRON) is an apparatus to generate an amplitude-modulated microwave beam.

4. A new method of constructing predetermined magnets from appropriate magnetic material that allows for focusing the magnetic field in a target region.

The above-mentioned technological components, alone or in combination, render the following devices and systems possible:

1. Compact and portable in-situ NMR spectrometers that can be dipped in the fluid to be measured and are easily maintained, with affordable coil constructions and/or with DNP enhancement, together with an apparatus to recover depleted magnets.

2. Chromatography detectors incorporated into a separation column (including but not limited to HPLC and uHPLC) and/or chemical flow detectors, real-time switches, and executive/actuator devices enabling but not limited to detection in tube.

3. Magnetic Resonance Non-Invasive Beam (MR. NIB) are real-time MRI methods with or without DNP enhancement.
4. Magnetic Resonance Non-Invasive Blade (MR. NIB) are real-time methods with real-time surgeon guidance and navigation, and which have fully automatic or semi-automatic options.
5. Permanent magnet assembly with focused permanent magnetic field that also has low field outside the focused region, securing against magnetic incidents during surgical operation and treatment.

In addition, applications for the use of MR. NIB include but are not limited to:

Therapy for the reduction in health/growth of sparse tumors or other undesired tissue populating one or more regions of the body.
Removal of blood clots.
Activation by controlled heating of blood vessel stents where the stent is covered by or constructed with materials responsive to NMR frequencies.
Acceleration of attraction and blood stream absorption of undesired chemical compounds (such as aluminum) from cells having heavy concentrations of said compounds.
Once in the bloodstream, their subsequent elimination from the body is achievable via natural liver function.
Acceleration of platinum-based chemotherapy.
Acceleration of cobalamin effects in the human body.

BRIEF DESCRIPTION OF THE DRAWINGS

FIG. 1: A processing method to convert.

FIG. 2: A processing method to generate.

FIG. 10: The Electron Larmor Microwave Amplifier THReaded On Nuclei (ELMATHRON).

FIG. 13: ELEGANT NMR spectrometer embodiment for in-situ measurements, where FIG. 13A refers to the complete assembly, FIG. 13B refers to the component containing the electronics, FIG. 13C refers to the sensor block for performing measurements in a fluid flow, FIG. 13D refers to the sensor block when dipped in fluid to be measured, and FIG. 13E demonstrates how the dipped sensor may be constructed to be suitable for standard ground glass joints (this embodiment can be constructed with or without the ELMATHRON and refers to FIGS. 13-14).

Figures 14A, 14B:
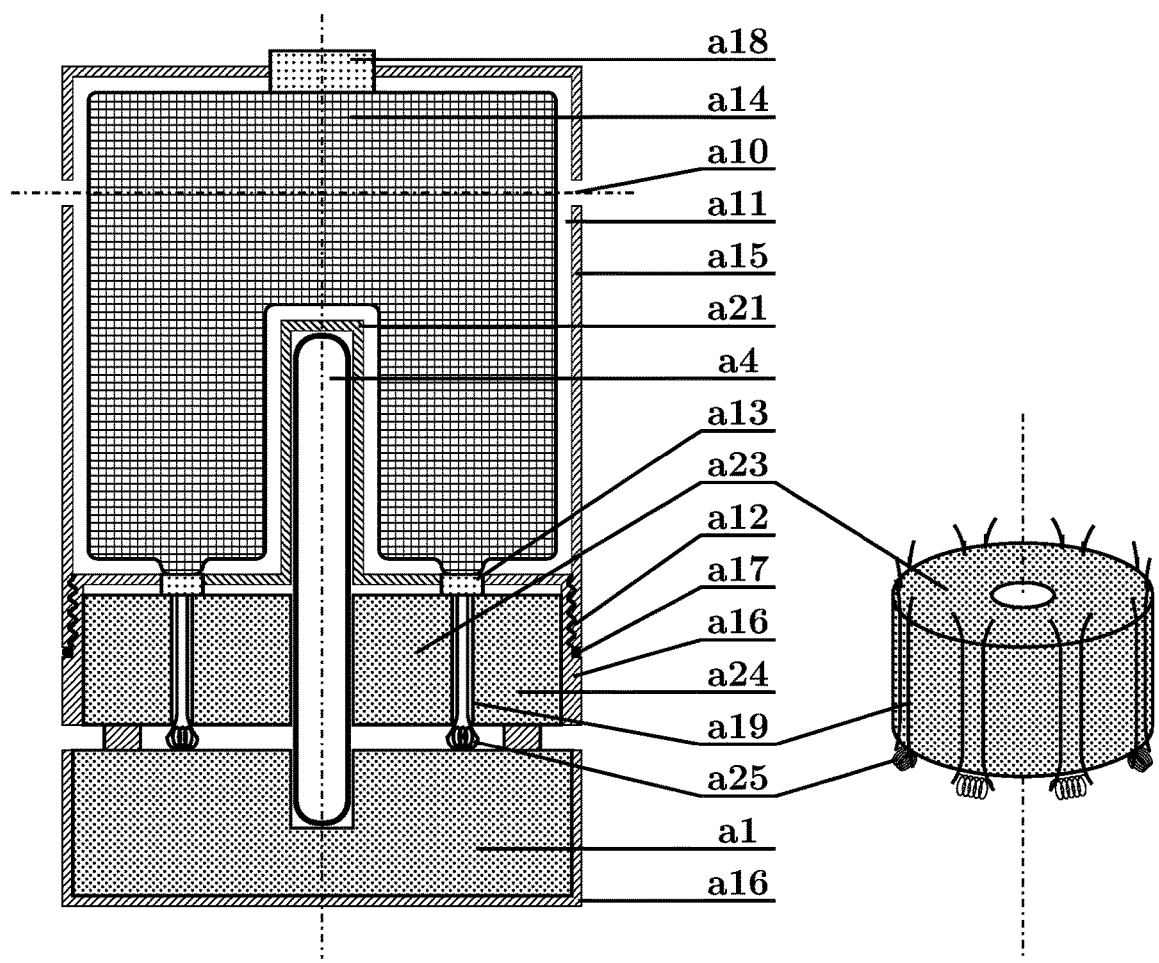
FIG. 14: ELEGANT NMR spectrometer embodiment for in-situ measurements enhanced by ELMATHRON a4, where FIG. 14A refers to the complete assembly, FIG. 14B demonstrates the connection of receiver coils a25 along magnets (a23 and a24), FIG. 14C refers to the sensor block for performing measurements in a fluid flow, and FIG. 14D refers to the sensor block when dipped in fluid to be measured.
Figures 14C, 14D:
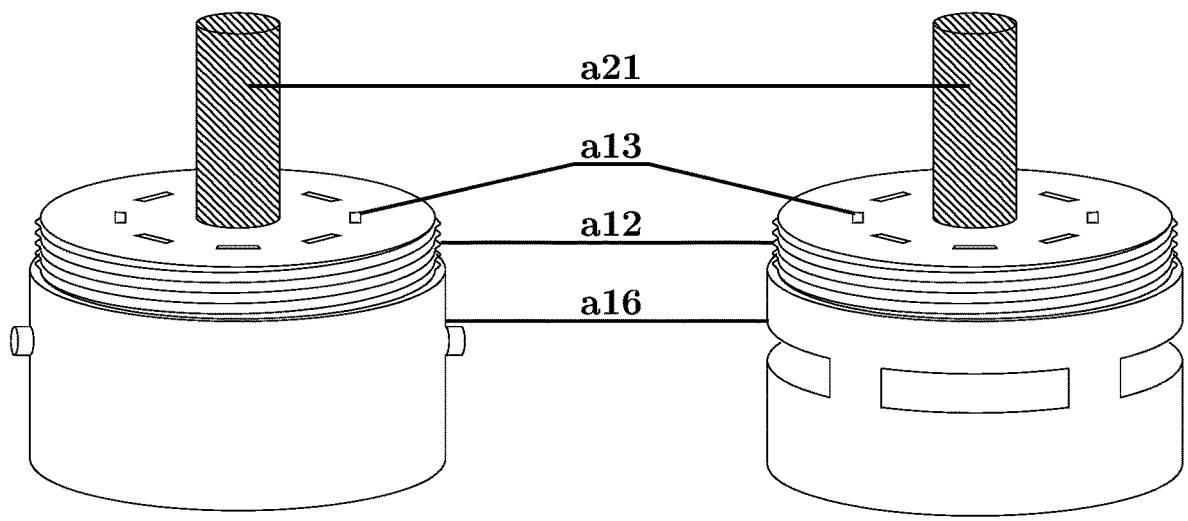
Figure 15A:
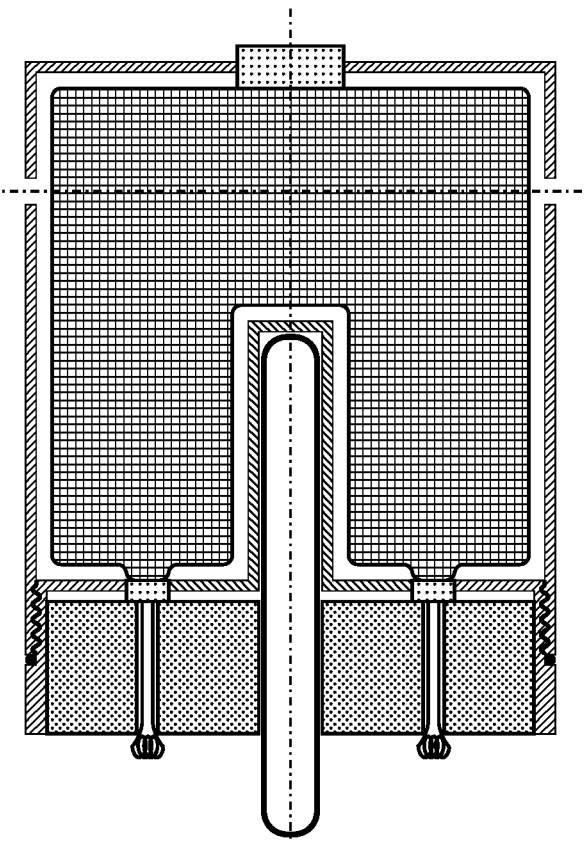
FIG. 15: Embodiments for ELEGANT NMR spectrometer for in-situ measurements with (FIGS. 15A-15B) and without (FIGS. 15C-15D) the ELMATHRON characterizing from the embodiments in FIGS. 13-14 in having a magnet structure with better access of the receiver coil(s) and/or NMR detector(s) to the measured fluids, albeit lower magnetic field strength.
FIG. 15E demonstrates how a dipped sensor may be constructed so as to be suitable for standard ground glass joints (this embodiment can be constructed with or without the ELMATHRON).
Figure 15C:
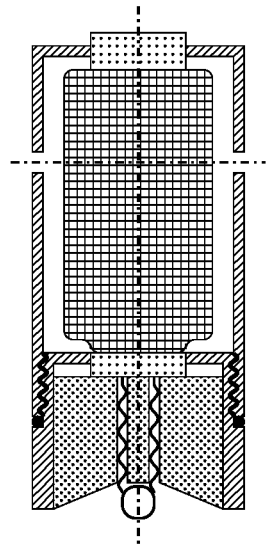
Figure 15E:
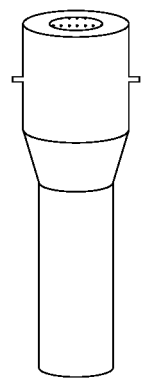
Figure 15B:
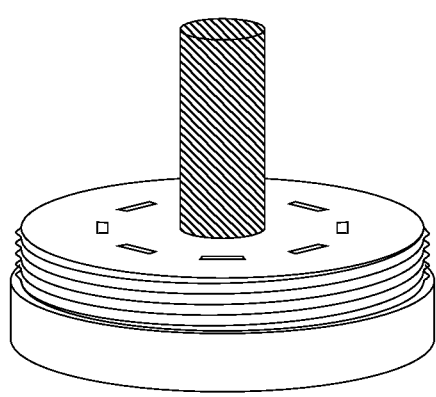
Figure 15D:
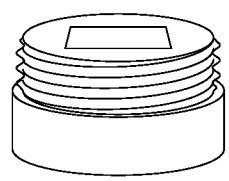

An important difference of these embodiments (FIG. 15) from that in FIGS. 13-14 is that the shape of magnet a1 may curve inward or have any other shape that improves total magnetic field strength and smoothness and is also appropriate for embodiments both with and without ELMATHRON.

Figure 16A:
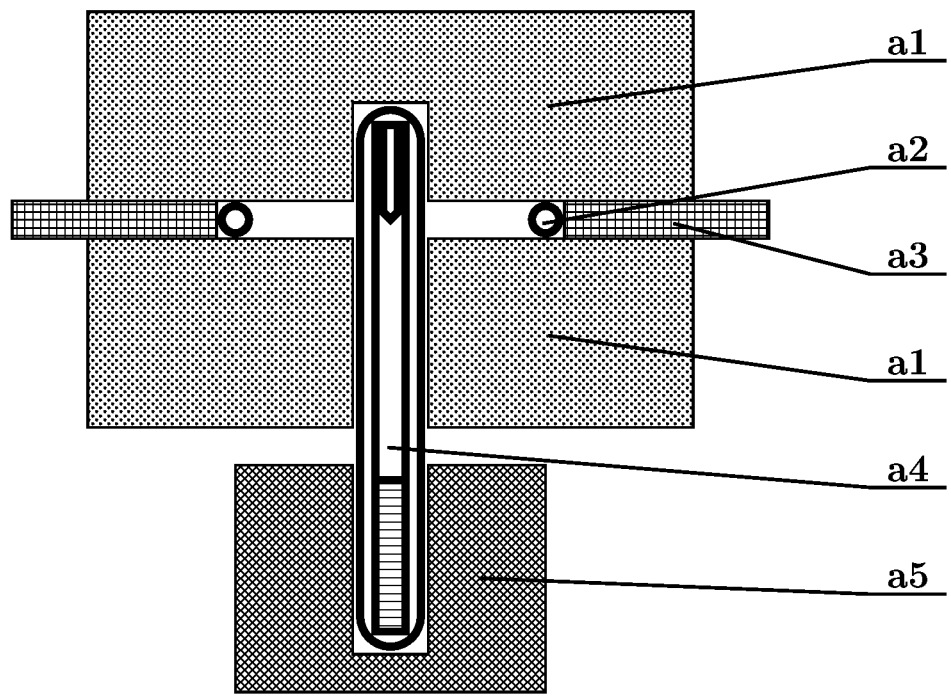
Figure 16B:
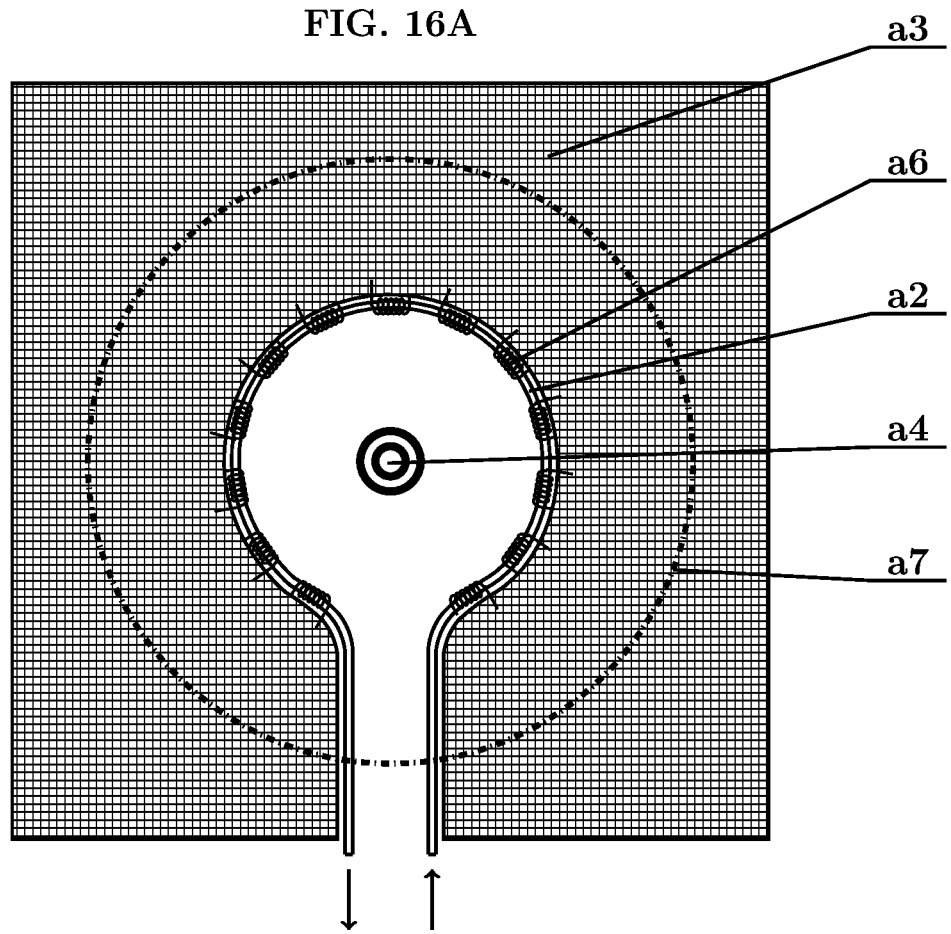

FIG. 16: ELEGANT NMR spectrometer embodiment with encapsulated permanent magnets a1 and one ELMATHRON a4 emitting diffracting waves over its diffraction grating e7. Fluid sample is supplied continuously through the tube or capillary or chromatography column a2. FIG. 16A shows a side view, and FIG. 16B shows top and bottom views.

Figure 17A:
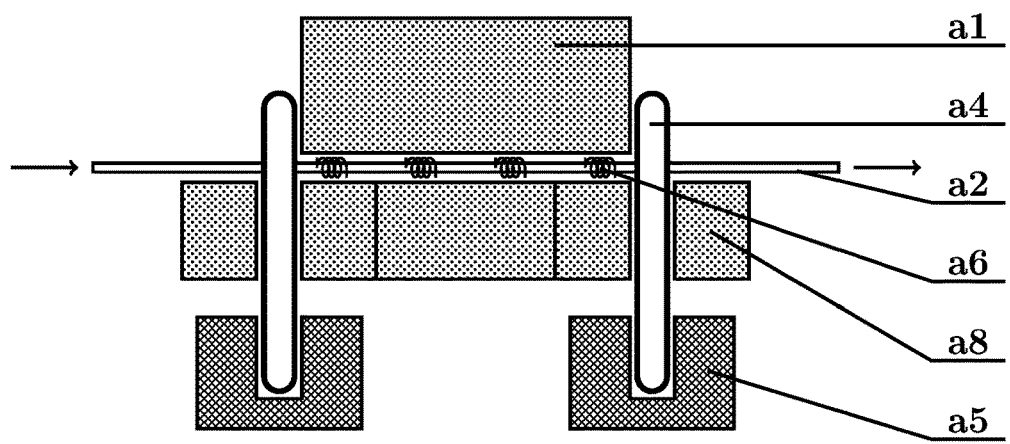
Figure 17B:
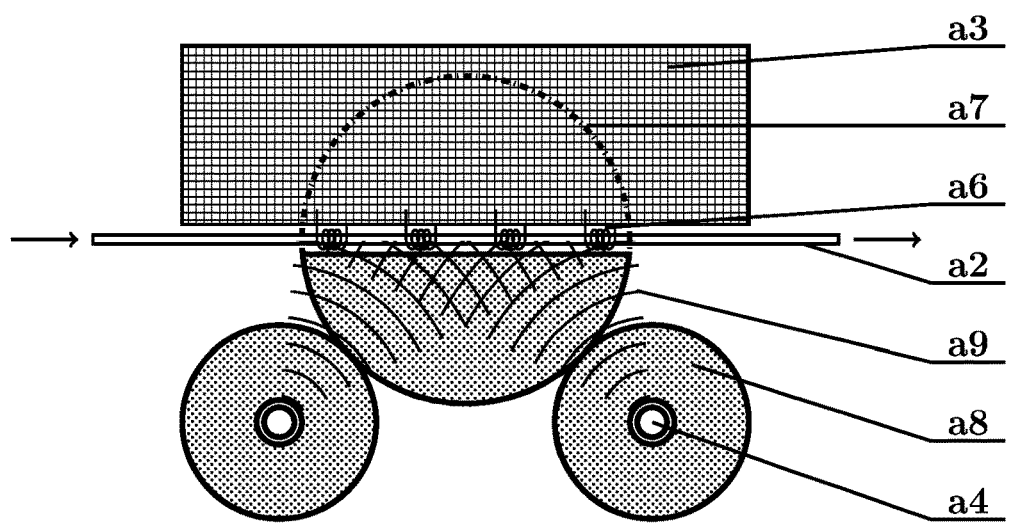
Figure 17C:
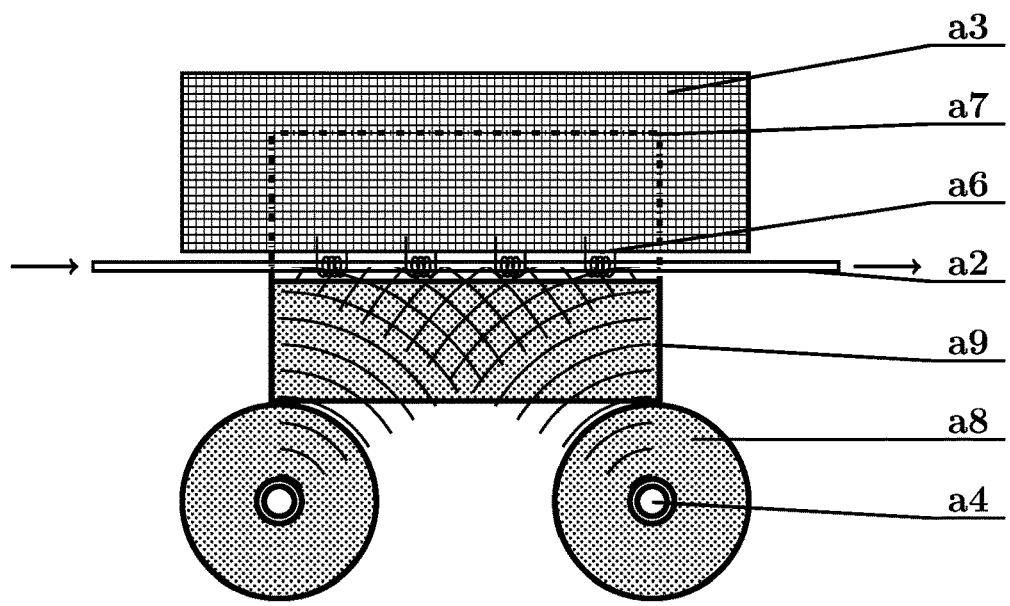

FIG. 17: ELEGANT NMR spectrometer embodiment with encapsulated permanent magnets a1 and two ELMA- THRONs a4 emitting diffracting waves a9. Fluid sample is supplied continuously through the capillary or chromatography column a2. FIG. 17A shows a side view, and FIGS. 17B-17C show top and bottom views. Several other embodiments can be considered: magnet a3 may take different shapes/forms (FIG. 17B with vertical cylinder and FIG. 17C with horizontal cylinder) such that its permanent magnetic field covers the large area where the capillary or chromatography column a2 is situated; a6 may be coils and/or optical NMR detectors; and instead of one or all ELMATHRONs, a transmitter coil situated in parallel with a6 may be used.

FIG. 18: ELEGANT NMR spectrometer embodiment with ELMATHRON a4 capable of working in an external magnetic field a26 (from permanent magnets or superconductor coil(s)). Fluid sample is supplied continuously through the capillary or tube or chromatography column a2. FIG. 18A shows a side view, and FIG. 18B is a detailed view of the capillary/tube/column a2, receiver coils a6, and receiver electronic PCBs a3.

FIG. 19: Droplet size distribution measurement of a sample with two phases. The same picture demonstrates how magnetization from the stationary phase is transferred to the mobile phase in the case where a chromatography column with incorporated NMR sensors is used.

Figure 20:
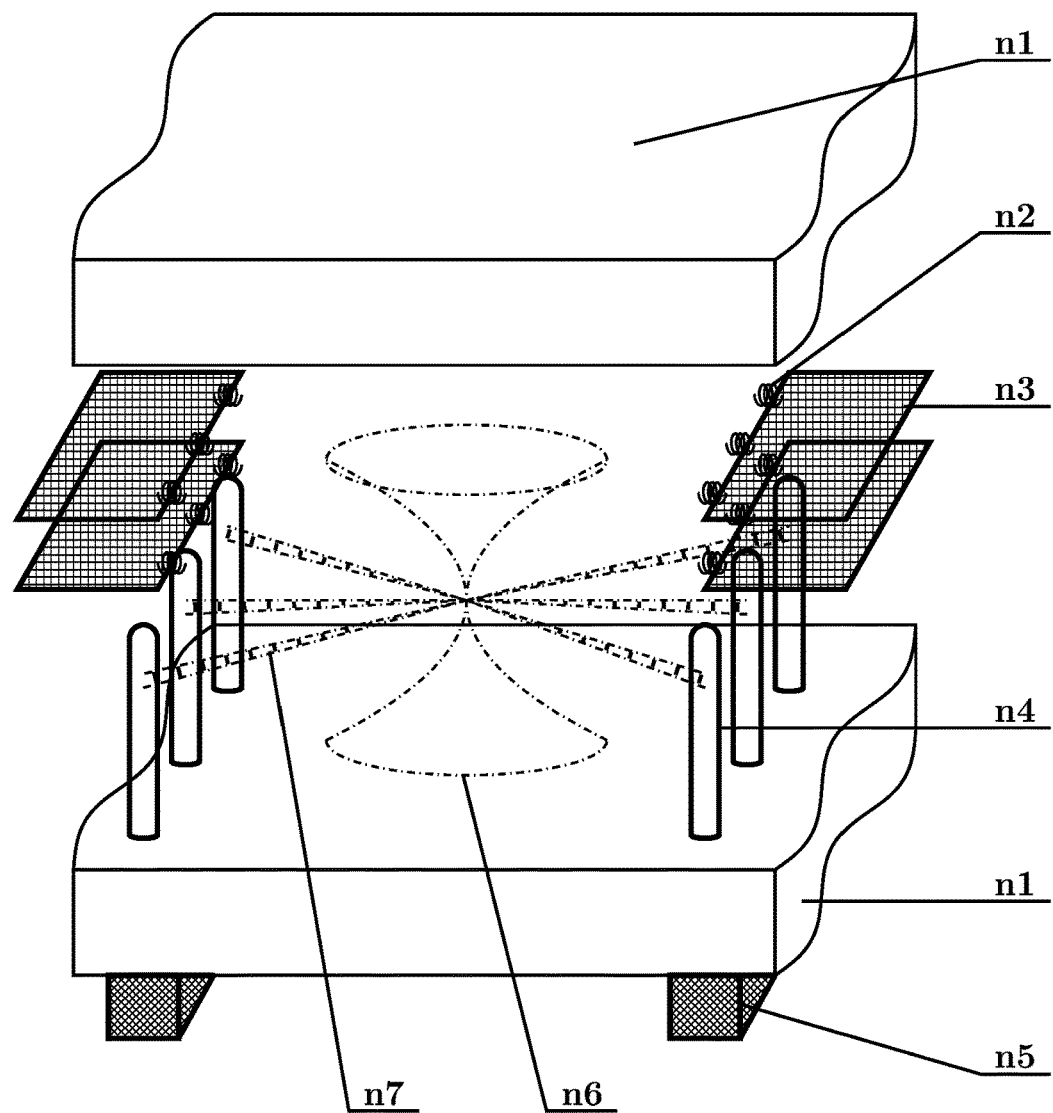

FIG. 20: Magnetic Resonance Non-Invasive Blade as well as Magnetic Resonance Non-Invasive Beam (MR. NIB) system for real-time MRI and/or real-time non-invasive surgical applications together with real-time guidance and optionally unmanned operation.

Figures 21A, 21B:
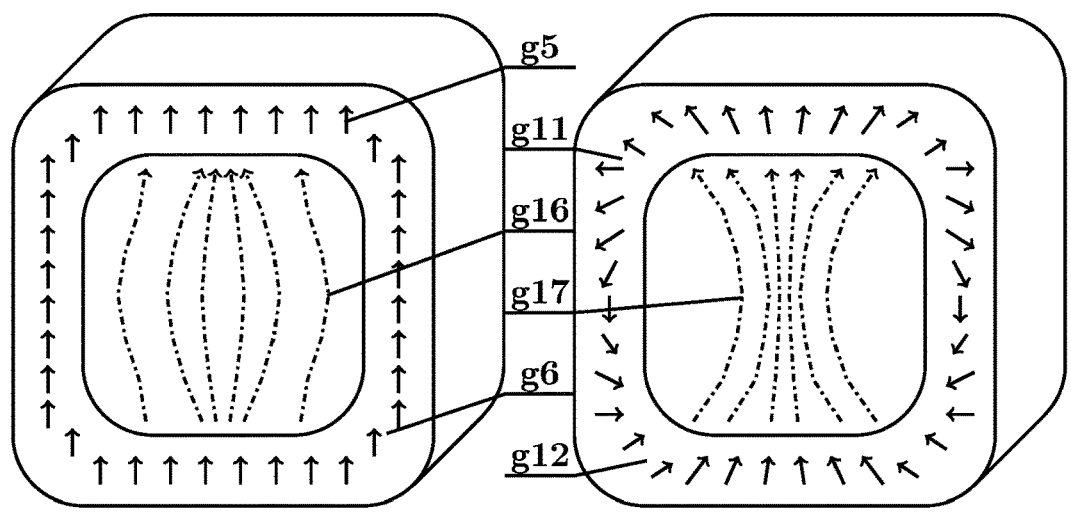

FIG. 21: A magnet assembly with linear anisotropic (FIG. 21A) and nearly-optimal (FIG. 21B) magnetic polarization and the corresponding contour-plot of magnetic field strength of an area between magnets.

Figure 22:
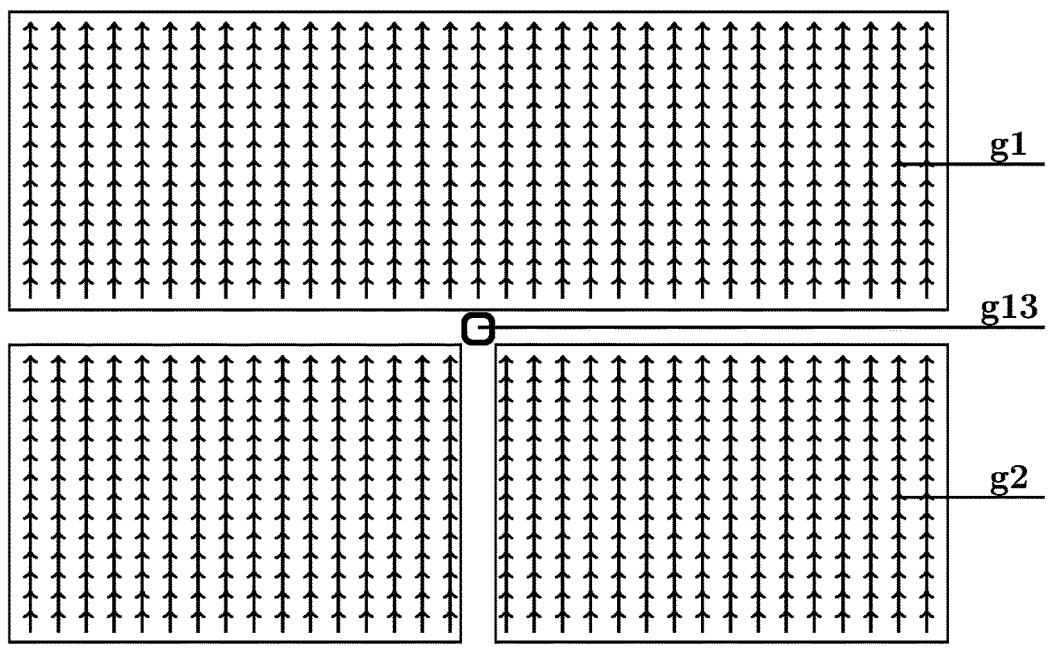

FIG. 22: A magnet assembly with linear anisotropic magnetic polarization for NMR spectrometers without ELMATHRON.

Figure 23:
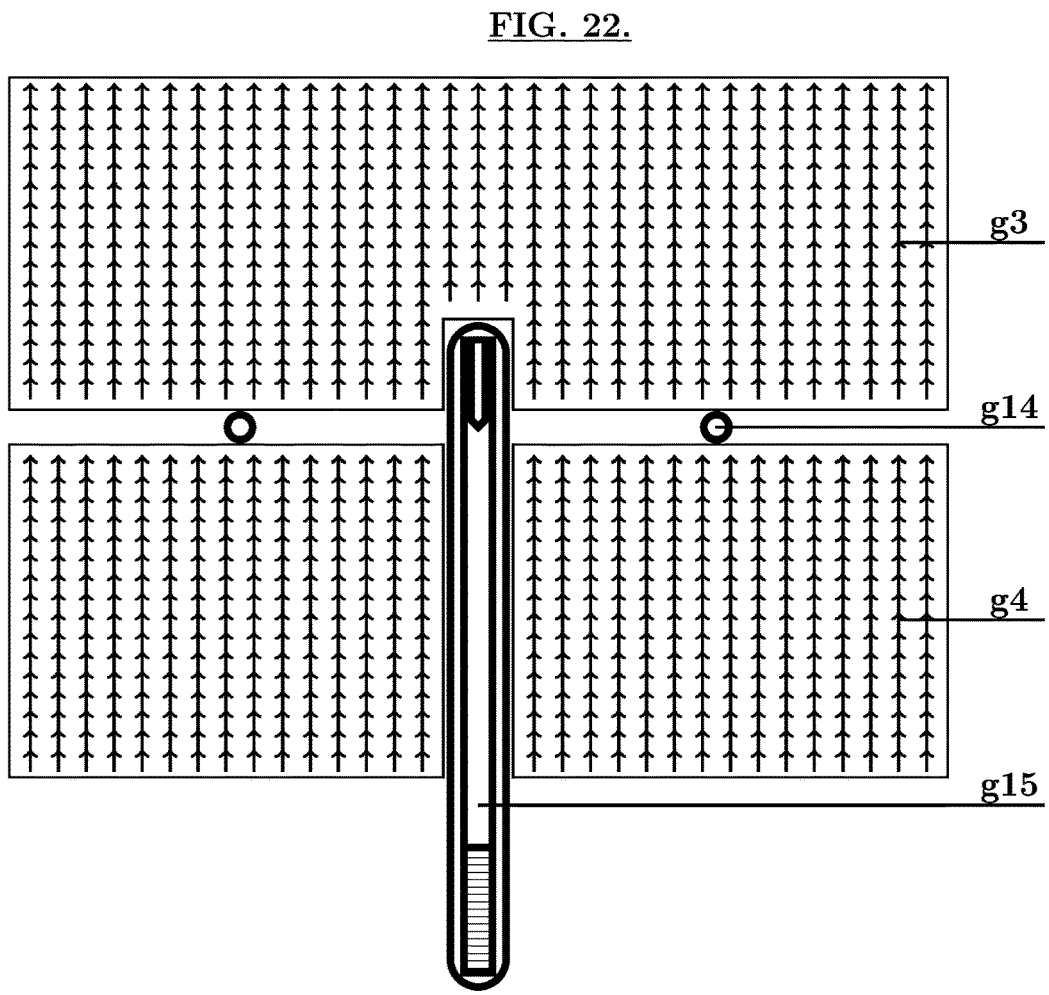

FIG. 23: A magnet assembly with linear anisotropic magnetic polarization for NMR spectrometers with ELMATHRON.

Figure 24:
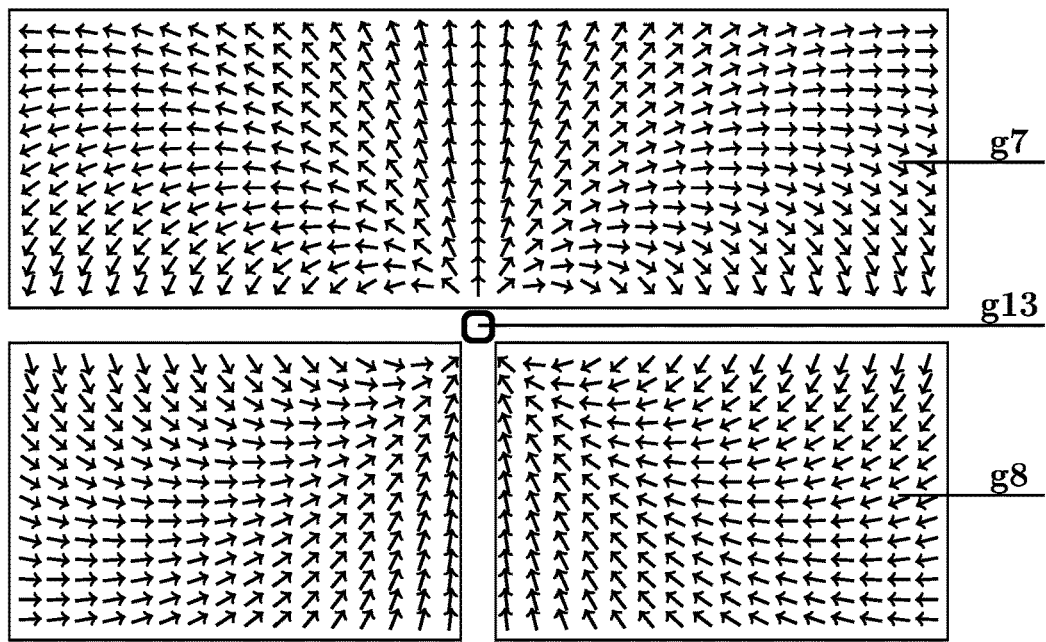

FIG. 24: A magnet assembly with nearly-optimal magnetic polarization for NMR spectrometers without ELMATHRON.

Figure 25:
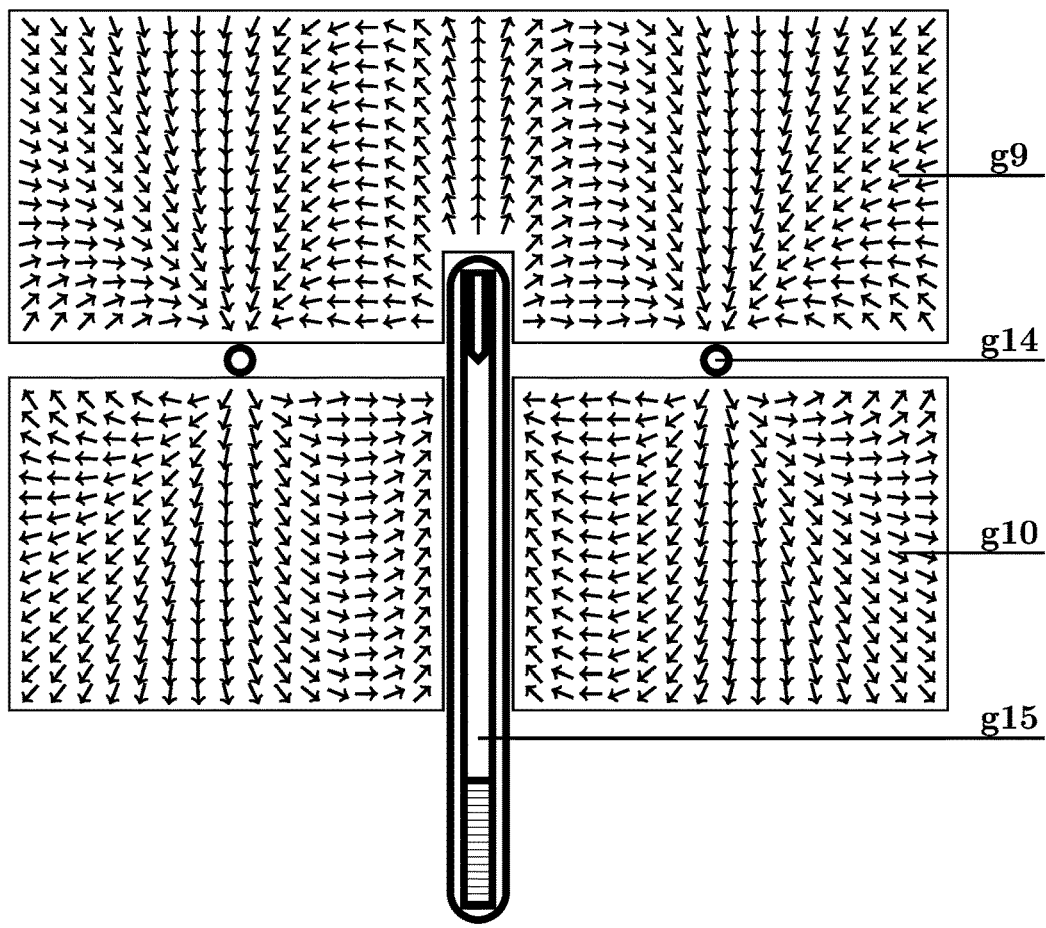

FIG. 25: A magnet assembly with nearly-optimal magnetic polarization for NMR spectrometers with ELMATHRON.

Figure 26:
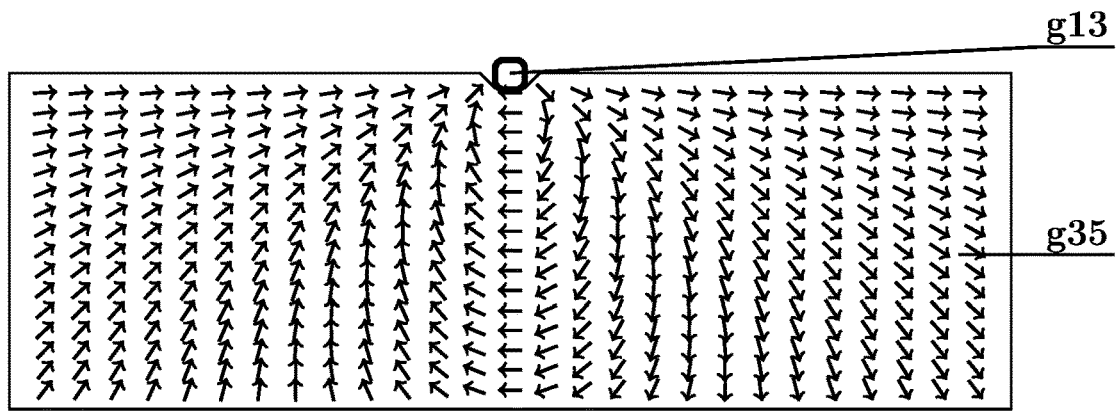

FIG. 26: A magnet assembly for a side-NMR embodiment with nearly-optimal magnetic polarization for NMR spectrometers without ELMATHRON.

Figure 27:
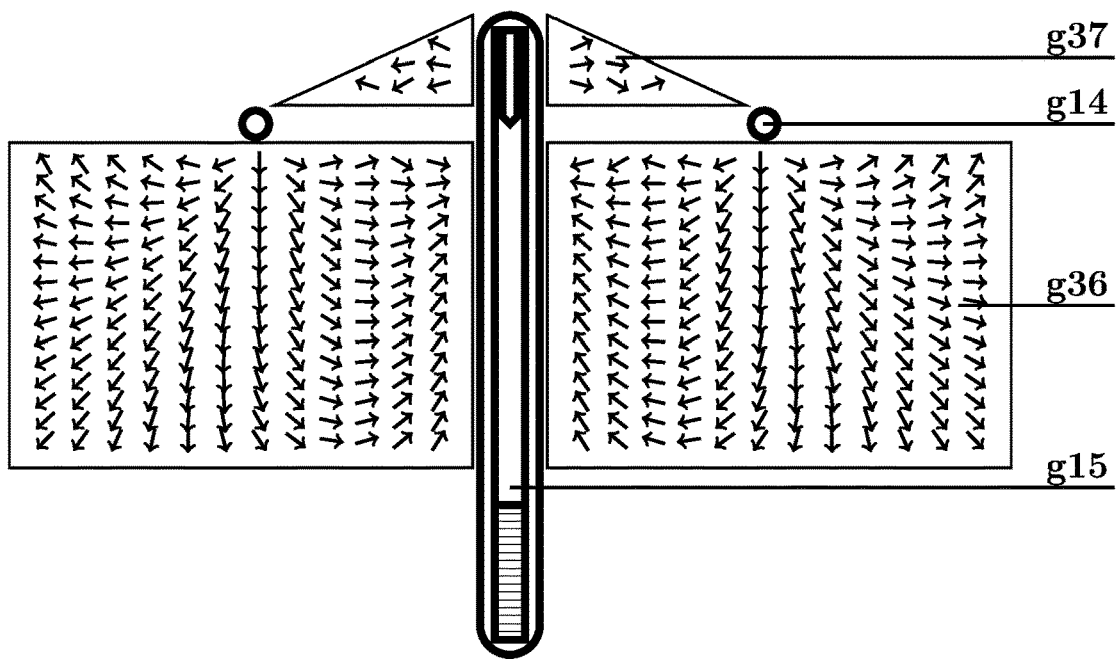

FIG. 27: A magnet assembly for a side-NMR embodiment with nearly-optimal magnetic polarization for NMR spectrometers with ELMATHRON.

Figure 28:
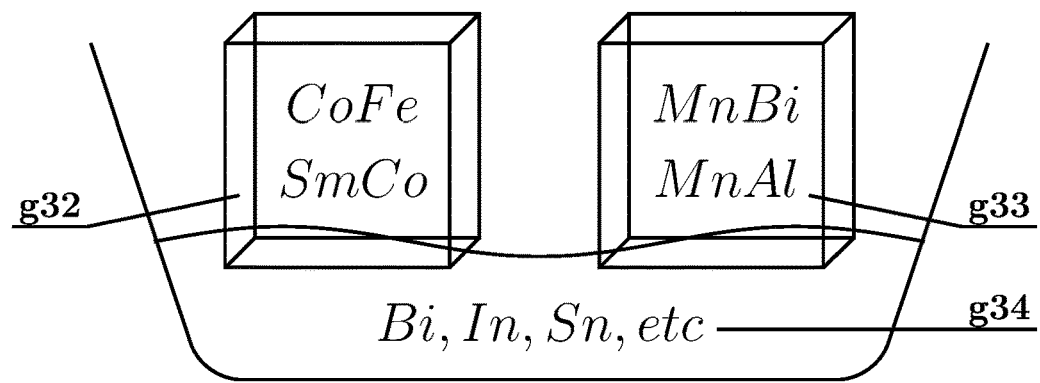

FIG. 28: A magnetic alloy, comprising:
(a) crystals of Co—Fe and/or Sm—Co magnetic alloys;
(b) crystals of Mn—Bi and/or Mn—Al and/or any other bismuth based magnetic alloys;
(c) low-melting metals that are able to make low-temperature liquids with (b),
wherein a material phase of the alloy is metallic.

Figure 29:
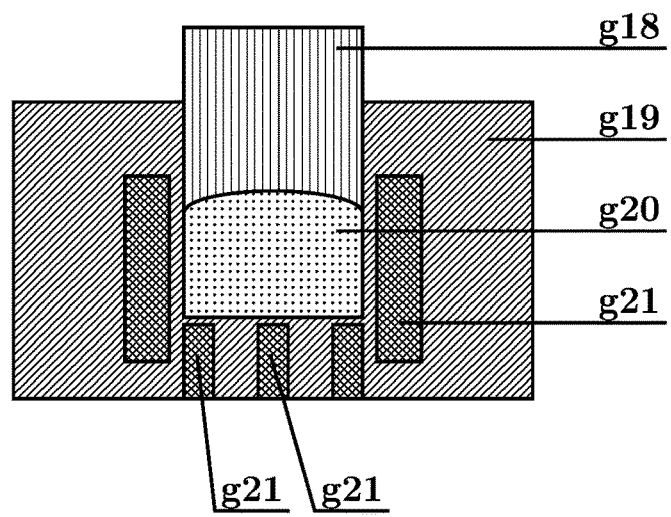

FIG. 29: A processing method and an apparatus for pressing anisotropic magnetic powder into permanent magnets with non-uniform magnetic polarization. This figure additionally demonstrates one example of magnetic structures with a magnetic area that forces particles of magnetic powder to remain oriented in the prescribed direction.

Figure 30:
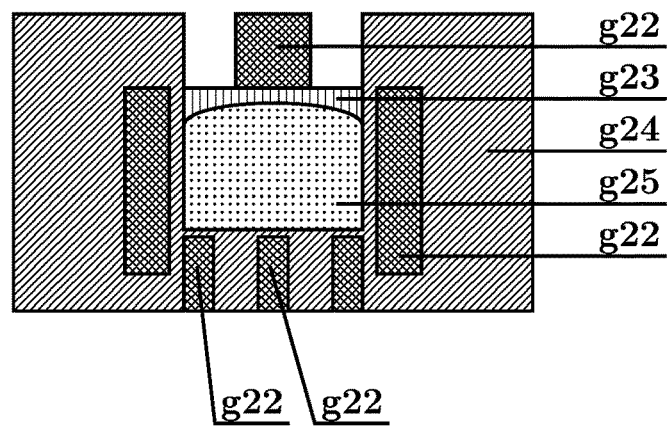

FIG. 30: A processing method and an apparatus for final magnetization.

Figure 31:
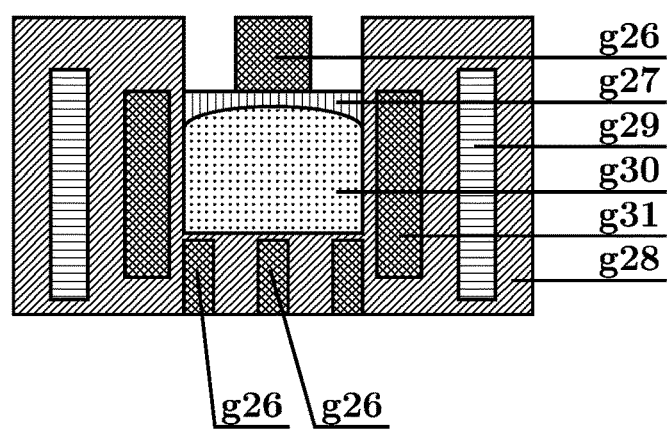

FIG. 31: A processing method and an apparatus for casting permanent magnets with non-uniform magnetic polarization. This apparatus may incorporate the capability to perform a final magnetization step.

FIG. 32: A system that demonstrates a method and an apparatus for chemical analysis which consists of an area filled with different markers, so-called stationary phases. Each marker contains one or several active parts, abbreviated as A, B, C, D, E, that each possess good affinity to different organic groups (A, B, C, D, E) presented in an investigated mixture. These markers cause different substances in the investigated mixture to rotate differently upon interaction and build the corresponding intermolecular iteration (A-A, B-B, C-C, D-D, E-E). For each region with a corresponding marker, we perform a different multidimensional NMR experiment, so that the magnetization transfer from each particular organic or element group in said marker mainly progresses to particular components or parts in the unknown mixture, and this transfer is measured over multidimensional NMR responses. Doing such an experiment does not require physical separation of the mixture; the NMR spectra separate in different regions and allow the detection of all components in the unknown mixture. This method for recognizing substances in an unknown mixture may be applied in all embodiments in FIG. 13-18, FIG. 33 by incorporation of said markers into the measured area and/or by impregnating them into the walls of the measured area.

FIG. 33: The apparatus for performing qualitative and quantitative evaluation of composition without need for complete separation of substances in the measured mixture using the method in FIG. 32 and with the measurement area comprising of a plate (FIGS. 33B and 33D) or a tube (FIGS. 33A and 33C) with different markers. The first and the second embodiments (FIGS. 33A and 33B) demonstrate versions with one or few NMR receiving coils but incorporating spherical Halbach magnets with higher magnetization. The third and the fourth embodiments (FIGS. 33C and 33D) demonstrate versions with a plurality of NMR receiving coils that are situated along a line; this version may only incorporate magnets with cylindrical Halbach structures, which have lower magnetization by a factor of 3/4.

Figure 1A:
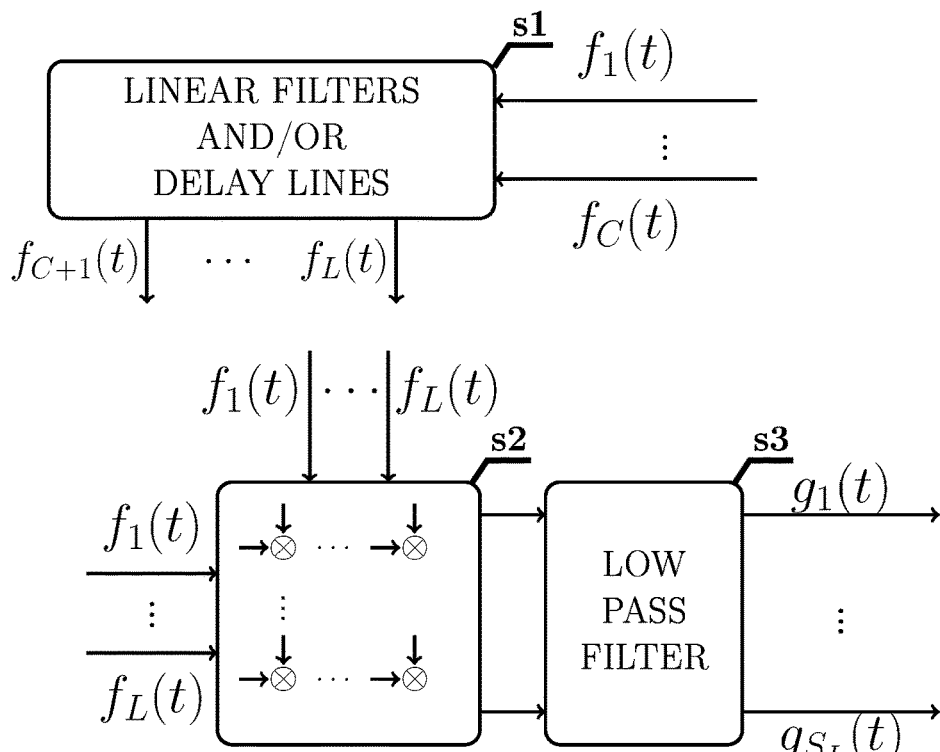
FIG. 1A wide-band signals $f_1(t), \ldots, f_C(t)$ having one or several carrier frequencies.

REFERENCE NUMERALS s1: Linear filters and/or delay lines. If one or several elements of this block are implemented with digital signals, a corresponding numerical approximation may be used.

s2: A set of mixers with each mixer receiving a pair of signals ($f_{l_1}(t)$, $f_{l_2}(t)$), $l_1$, $l_2=1, \ldots, S_L$ and delivering its product.

s3: Low-pass filter block that is used in parallel with all passed signals.

s4: Receiver coil or optical receiving detector.

s5: One or more sequentially-connected amplifiers.

s6: A processing block that converts $g_s(t)$, $s=1, \ldots, S_L$ to a table H, spectra responses $p_{nj}(t)$, $n=1, \ldots, N$, $j=1, \ldots, J$, and estimate of the total number of non-zero-spin isotopes N, solving minimization problem (f15).

s7: Mixer and summator block that performs operation (f10).

s8: Mixer and summator block that performs operation (f10) in the case where no long delay lines are used.

s9: A marker a substance/mixture containing at least one non-zero-spin isotope with a priori known spectra and concentration that is either:

situated in the measured substance, or incorporated as the reference unit inside coils s4, or incorporated in the walls of the measuring NMR camera.

s10: One or several frequency generators and their signals, delayed on 1/4 period. Each frequency generator has fixed ratio ($a_n/b_n$) to the main frequency generator.

s11: A set of mixer pairs with each mixer pair receiving a pair of signals ($f_l(t),Re(v_n(t))$) or ($f_l(t),Im(v_n(t))$) and delivering their products.

s12: A processing block that incorporates the method described in FIG. 3.

s13: A block that continuously supplies pipeline data $u_{lnj}(t)$, l=1, ..., L, n=1, ..., N, j=1, ..., J from s12 into local storage and delivers it to processing block s14.

s14: A processing block that solves minimization problem (f12).

s15: A processing block that incorporates the method described in FIG. 1 followed by the method from FIG. 2.

s16: A processing block that solves minimization problem (f16).

s17: A block that continuously supplies pipeline data $r_{nj}^2(t)$, n=1, ..., N, j=1, ..., J from s15 into local storage and delivers said data to processing block s16.

s18: A block that gathers data $r_{nj}^2(t)$, n=1, ..., N, j=1, ..., J from several blocks s15 and delivers said data to processing block s16.

s19: A processing block that incorporates the method described in FIG. 1.

s20: A processing block that simultaneously solves minimizations (f15) and (f17).

s21: A block that continuously supplies pipeline data $g_{sj}(t)$, s=1, ..., $S_L$ from s19 into local storage and delivers said data to processing block s20.

s22: A block that gathers data $g_{sj}(t)$, s=1, ..., $S_L$, j=1, ..., J from several blocks s19 and delivers said data to processing block s20.

s23: Real-time intermediate data generator and sensor.

s24: Non-real-time action generator.

s25: Non-real-time database updater.

s26: Real-time database searcher.

s27: Real-time action.

e1: A spring that ties tube e9 and plug e4 so that they remain at the same positions relative to the vessel of ELMATHRON e2.

e2: Hermetically-sealed glass and/or ceramic case/vessel of the ELMATHRON, preferably without any via/hole for power/energy supply and vacuum supply.

e3: The getter.

e4: A plug with a non-conductive wave reflector e8 at the bottom.

e5: Shielding situated/printed on the outer side of tube e9, which reduces undesirable electromagnetic emission.

e6: The anode constructed as a thick, monolithic layer on the inner side of tube e9.

e7: Diffraction grating.

e8: The wave reflector, constructed as a cone, a flat, or a focusing/collecting mirror, or other shape of mirror such that some part of the emitted waves may be reflected back to cathode e13 to accelerate the cathode's electron emission.

e9: Glass and/or ceramic tube situated inside the hermetically-sealed ELMATHRON's vessel e2; its outer diameter should be as close as possible to, but a little bit smaller than, the inner diameter of the vessel e2, preferably with printed traces on the inner and outer surfaces. The tube walls should be as small as possible, but only large enough to be resistant to the peak voltage that occurs at the secondary winding e16 during operation.

e10: An external system or device that provides the permanent magnetic field.

e11: Several parallel traces situated along the main axis of the ELMATHRON's vessel e2 and printed/placed on the tube e9. All of the traces on one side are smoothly connected to each other and to the secondary winding e16, while those on the opposite side are connected to the diffraction grating e7.

e12: Depending on the embodiments, this may be:

a feedback control to sustain the cathode e13 at a predetermined temperature, and/or an electromagnetic beam to heat the cathode e13, and/or an electromagnetic beam to accelerate electron emission from the cathode e13.

e13: The cathode, constructed of tungsten or any other high-melting metal or alloy; electrically, the cathode behaves as a shorted turn if heating of the cathode is performed by inductive and/or electromagnetic methods. It may be covered by a substance to accelerate electron emission.

e14: A primary winding of a cathode heater.

e15: The getter block, which serves as an ion pump.

e16: The secondary winding of the forward converter, with coils on the inner and outer sides of the tube e9. The sides may have windings with different numbers of turns, or one side (inner or outer) may have no windings with a straight conductive line or any other connection that does not act as a shorted turn.

e17: Several parallel primary windings of the forward converter. Preferably, each winding is printed on one PCB together with its powering electronics, and these PCBs are stacked atop each other.

e18: Power supply and control unit for e17.

e19: Power supply and control unit for e14, with feedback control (optical or infrared) to prevent overheating of the cathode e13.

a1: Permanent magnet(s). The magnets may have cylinder shapes with horizontal axes as shown in FIG. 17C, or any other shapes that permit better placement of the capillary/tube/column a2: while also supporting a magnetic field of sufficient strength covering where measurements occur and where the ELMATHRON vessels are situated.

a2: Capillary or tube or chromatographic column with investigated substance.

a3: PCB with receiver electronics.

a4: The ELMATHRON vessel.

a5: Power supply and control unit of the ELMATHRON.

a6: Receiver coils and/or optical NMR detectors situated on/in/over the capillary/tube/column a2.

a7: Permanent magnet boundaries; permanent magnets a1 are situated one over and one under the capillary/tube/column a2, PCB a3, and receiving coils a6.

a8: Permanent magnets of the ELMATHRON; these magnets may be incorporated in the main magnet assembly a1.

a9: Interference waves from ELMATHRONs.

a10: Thermostat connectors: cooling/heating fluid is dispersed over these connectors to control the temperature of the electronics inside the device.

a11: Area inside the ELEGANT NMR spectrometer with constant temperature controlled by fluid thermostatting.

a12: Screw threads to screw the block with magnets a16 to the block with electronics a15.

a13: Plugs that connect the coils (a20 or a25) to the electronics a14.

a14: PCB assembly with transmitter and receiver electronics. In the case of a thermostat connection being used, the PCBs should be coated with appropriate materials to prevent damage by fluid thermostatting.

a15: Main case of the device, housing the electronics a14.

a16: The case for the block with magnets.

a17: Gasket for hermetic connection.

a18: Data and power supply connector.

a19: Wires to connect plug(s) a13 with coil(s) a20 or a25.

a20: Receiver and transmitter coil assembly, one embodiment of the coils assembly described in FIG. 12.

a21: Hermetically-sealed non-conductive case that is connected and incorporated into the magnetic block a16 and that allows electromagnetic waves to penetrate and generate inductive and/or electromagnetic coupling from a14 to a4.

a22: Flow connectors. One can connect tubes to perform measurements in flow. In the case of the solid-state and NMR tube detector embodiment being used, said connectors should allow an external tube to be placed inside the measurement area and associated coils. In the case of the embodiment with ELMATHRON being used, said connectors may be asymmetrical in order to fulfill conditions on the placement of the external tube.

a23: Permanent magnet in the form of a cylinder with an inner diameter slightly larger than the outer diameter of the ELMATHRON vessel a4. Between the ELMATHRON vessel and this magnet, a special gasket may be installed to keep this connection hermetic and to ensure that the glass/ceramic case of the ELMATHRON is not broken through mechanical vibrations and/or temperature expansion from the magnet cylinder.

a24: A permanent magnet in the form of a cylinder with an inner diameter slightly larger than the outer diameter of the magnet a23. Wires a19 are situated between said magnet cylinders a23 and a24. The magnets a23 and a24 may be hermetically coupled, in which case a special gasket should be installed between a23 and a24.

a25: Receiver coils and/or optical NMR detectors.

a26: External magnetic field generated by permanent magnets or superconductor magnets.

a27: Ground glass joint.

a28: Thin plate comprising the measured area for the method described in FIG. 32. Inlets and outlets for mobile phase as well as the mechanical movement system for this plate are attached to said plate at its sides, but are not drawn for reason of figure simplicity.

d1: A transmitting wave is absorbed by droplet or stationary phase material.

d2: Droplet or stationary phase material emitting the same frequency wave or carrier frequency wave spectrum as absorbed in d1.

d3: A transmitting wave is absorbed by solution or mobile phase material.

d4: Solution or mobile phase material emitting the same frequency wave or carrier frequency wave spectrum as absorbed in d3.

d5: A transmitting wave is adsorbed by material situated on the surface of a droplet or a stationary phase.

d6: Solution material previously excited by magnetization transfer as in d7 emits a different frequency wave than was adsorbed in d5.

d7: Excited material on the surface of a droplet or a stationary phase transfers its magnetization to solution or mobile phase materials situated near the surface of the droplet.

n1: A plurality of permanent magnets with the potential for changing the direction and intensity of the magnetic field by mechanical movements (coarse tune) and by electromagnetic coils (fine tune).

n2: Receiver coils.

n3: PCBs with receiver electronics.

n4: ELMATHRON vessel(s).

n5: Power supply and control units of ELMATHRON(s) (controlled in parallel with receivers) with additional potential for changing the orientation and position of ELMATHRON(s) to change the directions of their beam(s).

n6: Non-uniform magnetic field formed by n1.

n7: Electromagnetic beam(s) from the ELMATHRON(s).

g1, g2: Permanent magnets with linear anisotropic magnetization for NMR spectrometers without ELMATHRON.

g3, g4: Permanent magnets with linear anisotropic magnetization for NMR spectrometers with ELMATHRON.

g5, g6: Permanent magnets with linear anisotropic magnetization for MR. NIB technology.

g7, g8: Permanent magnets with nearly-optimal magnetic polarization for NMR spectrometers without ELMATHRON. Top and bottom boundaries may be flat or some other shape to fit better into the mechanical assembly and/or for better access of the receiver coil(s) and/or NMR detector(s) to the measured fluids.

g9, g10: Permanent magnets with nearly-optimal magnetic polarization for NMR spectrometers with ELMATHRON. Top and bottom boundaries may be flat or some other shape to fit better into the mechanical assembly and/or for better access of the receiver coil(s) and/or NMR detector(s) to the measured fluids.

g11, g12: Permanent magnets with nearly-optimal magnetic polarization for MR. NIB technology. Top and bottom boundaries of both g11 and g12 magnets may be flat or some other shape to fit better into the mechanical assembly.

g13: Receiver and transmitter coils assembly, one embodiment of the coils assembly described in FIG. 12.

g14: Receiver coils or optical NMR detectors.

g15: The ELMATHRON vessel.

g16: Contour plot of a vertical magnetic field strength projection using permanent magnets with linear anisotropic magnetization in MR. NIB technology.

g17: Contour plot of a vertical magnetic field strength projection using permanent magnets with nearly-optimal magnetization in MR. NIB technology.

g18: Molding tool.

g19: Molding matrix.

g20: Magnetic powder with anisotropy.

g21: A set of one or several:
permanent magnets, and/or
ferromagnetic materials, and/or
permanent electromagnets, and/or
superconductor electromagnets, and/or
any other non-magnetic materials, and/or
permanent magnet(s) previously manufactured with the same technology.

g22: One or several coils for the generation of a permanent magnetic field, consisting of a foil of good-conducting metal. The total amount of winding in these coils should be sufficient to generate a permanent magnetic field of at least the same strength as the magnetic field delivered by nearly-optimal anisotropically manufactured (sintered, casted, pressed, etc.) magnets.

Construction of said coils may be accomplished with one coil or several sections of coils, including coils with different and/or opposite directions.

These coils should be connected over an electronic or mechanical switch to one or several capacitors, and/or super-capacitors, and/or batteries, and/or power supply units connected in parallel, which should be capable of delivering enough current so that the coils are able to generate a permanent magnetic field of at least the same strength as the magnetic field delivered by anisotropic magnets.

g23: Upper side of a device that prevents the magnetic material g25 from migrating up during final magnetization. It may comprise additional joints (not shown in the figure) that are strong enough to withstand the force between manufactured magnet g25 and coil(s) g22.

g24: The case of a device that prevents the magnetic material g25 and coils from migrating during final magnetization.

g25: Manufactured magnetic material prepared for final magnetization.

g26: One or several coils for the generation of a permanent magnetic field and/or heat, consisting of a foil of good-conducting metal. The melting point of said metal or parts of said coils situated close to g25 should be above the casting temperature.

Construction of said coils may be accomplished with one coil or several sections of coils, including coils with different and/or opposite directions.

These coils should be connected over an electronic or mechanical switch to one or several capacitors, and/or super-capacitors, and/or batteries, and/or power supply units connected in parallel, which should be capable of delivering enough current so that the coils are able to generate a permanent magnetic field of at least the strength produced by magnetic material casted anisotropically.

g27, g28: Upper side and case of a device that holds casted magnets and coils and may contain one or several temperature sensors.

g29: Additional fluid cooling that may be necessary to regulate temperature during casting and to ensure appropriate magnetic field strength.

g30: Casting magnetic material.

g31: The same coils as g26, which additionally may have the potential to generate inductive heating for g30 on the stage in order to increase the temperature and melting of material in g30.

g32: Crystals of Co—Fe and/or Sm—Co magnetic alloys.

g33: Crystals of Mn—Bi and/or Mn—Al and/or any other bismuth based magnetic alloys.

g34: Low-melting metals (In, Bi, Sn, Ga, Tl, Cd, Zn, Pb, Te and others) that are able to make low-temperature liquids with g33.

g35: Alternative embodiment (to g8) for permanent magnets with nearly-optimal magnetic polarization for NMR spectrometers without ELMATHRON.

g36: Alternative embodiment (to g10) for permanent magnets with nearly-optimal magnetic polarization for NMR spectrometers with ELMATHRON.

g37: Additional magnet for FIGS. 15A-15B embodiments that improve magnetic field strength.

DETAILED DESCRIPTION

Elegant NMR

The Enhanced multi-nucLEar Generation, Acquisition, and Numerical Treatment of Nuclear Magnetic Resonance spectra (ELEGANT NMR) is a processing method constructed according to the following scheme.

Figure 1B:
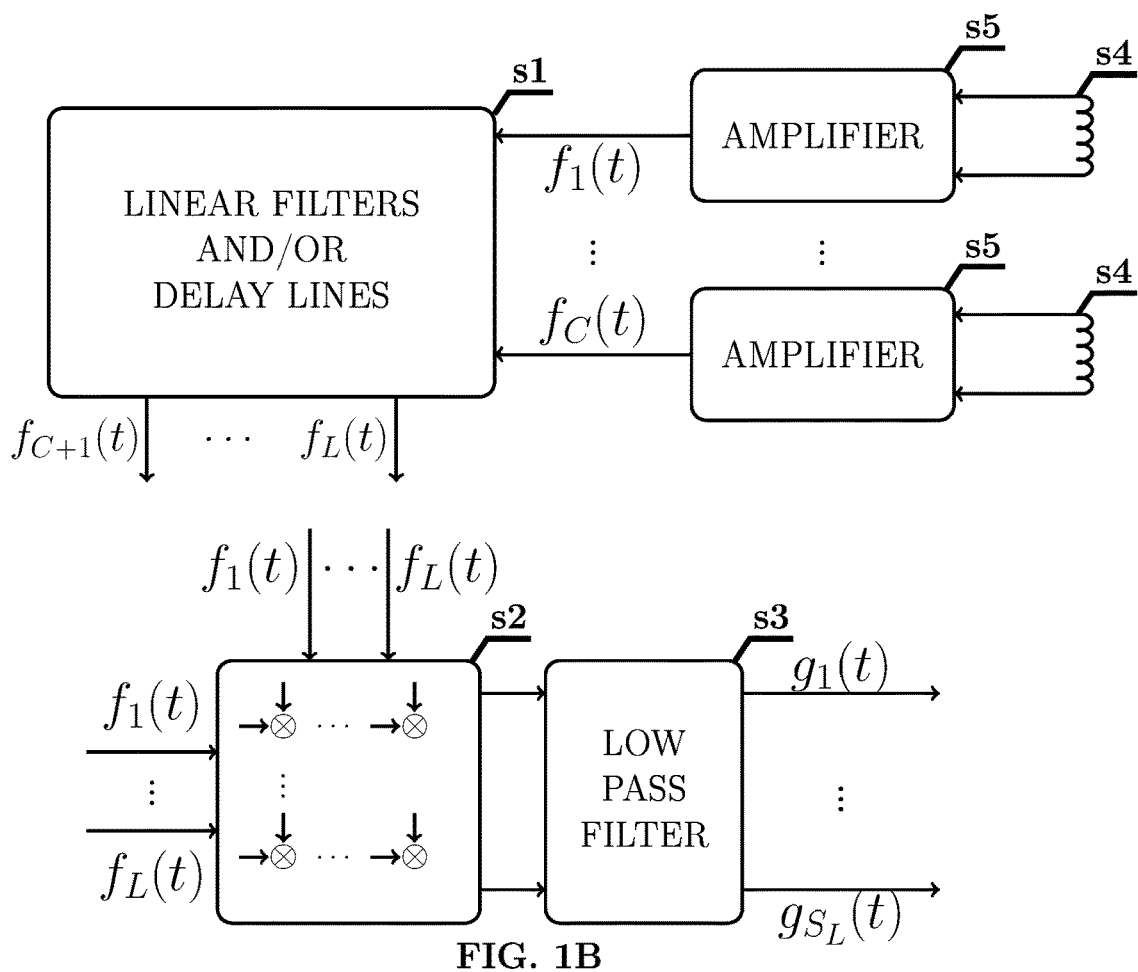
FIG. 1B wide-band NMR signals s4.

Consider FIG. 1B: One or several wide-band coils and/or optical detectors s4 receive very weak signals that are usually amplified by one or more sequential amplifiers s5. The signals are abbreviated as $f_l(t)$, $l=1, \ldots, C$, where C is the total count of input signals and t is the time domain variable of the measurements. These signals are forwarded to a block s1 of several linear filters and/or delay lines. These linear filters and delay lines may be comprised of passive components or operational and/or differential amplifiers and/or other analog circuits, or may be completely implemented digitally. The resulting signals are abbreviated as $f_l(t)$, $l=C+1, \ldots, L$. Each linear filter or delay line has one input and one output, acts on only one input signal, and delivers one output signal. All input signals may participate in the generation of signals after block s1 and, for practical reasons, L should be as small as possible without compromising the quality of the results upon a priori conditions, which will be discussed later. The case where C=L (no linear filters and no delay lines) is also possible.

All $f_l(t)$, $l=1, \ldots, L$ signals are forwarded pairwise to the mixer block s2. The same pairs of signals may be used, but are not counted hereafter. A subset of all possible pairs may be used. The total number of different mixers is denoted as $S_L$ and it is, by definition, $$S_L \leq \frac{L(L+1)}{2}.$$

The resulting signals from each mixer are forwarded over a low-pass filter s3 and abbreviated as $g_s(t)$, where $s=1, \ldots, S_L$ is the index of the mixer. An input pair of each s-th mixer refers to $$(f_{\xi_s^{(1)}}(t), f_{\xi_s^{(2)}}(t)),$$

where $\xi_s^{(1)}, \xi_s^{(2)} = 1, \ldots, L$. The resulting signals $g_s(t)$, by construction, are sufficient for reconstructing the pure spectra of all non-zero-spin isotopes (one input/coil setup in FIG. 1) and the spatial distribution of these spectra (multi-input/multi-coil setup in FIG. 1, for example, for MRI).

Assume a pure spectrum of each n-th non-zero spin isotope ($n=1, \ldots, N$) of the investigated substance is written as:

$$p_n(t) = \sum_{m=1}^{M_n} A_{nm} e^{i\omega_{nm}t + ib_{nm}} \in \mathbb{C}, A_{nm}, b_{nm} \in \mathbb{R}, \omega_{nm} \in \mathbb{C}, \quad \text{(f1)}$$

$$p_n(t) = r_n(t) e^{i\theta_n(t)}, r_n(t) = |p_n(t)|, r_n(t)\theta_n(t) \in \mathbb{R},$$

where $A_{nm}$ are amplitudes, $b_{nm}$ are phases, and $\omega_{nm}$ are resonance responses in the n-th non-zero-spin isotope spectrum. Additionally, assume that in a given magnetic field, the carrier frequency (Larmor frequency) of the n-th non-zero-spin isotope is $W_n$. The signal collected by the wide-band receiver coil/optical detector is then written as:

$$\sum_{n=1}^{N} \text{Re}(e^{iW_n t} p_n(t)), \quad \text{(f2)}$$

where Re(x) and Im(x) are the real and imaginary components of the complex number x. Taking into account that $W_n \gg \omega_{nm}$, linear filters and/or delay lines transform the signal (f2) to:

$$f_l(t) = \sum_{n=1}^{N} Q_{ln} \text{Re}(e^{iW_n t} e^{i\beta_{ln}} p_n(t+\delta_l)) = \qquad (f3)$$

$$\sum_{n=1}^{N} r_n(t+\delta_l) Q_{ln} \text{Re}(e^{iW_n t + i\beta_{ln} + i\theta_n(t+\delta_l)}),$$

where
$Q_{ln} \in \mathbb{R}$ and $\beta_{ln} \in \mathbb{R}$ are filter parameters in the case of linear filters being applied ($\delta_l = 0$),
$\delta_l$ is a delay in the delay line ($Q_{ln} = 1$ and $\beta_{ln} = W_n \delta_l$).
Blocks with arbitrary $\delta_l$, $Q_{ln}$, and $\beta_{ln}$ can be also considered.

It is also evident that if two delay lines with delays $\delta_1$ and $\delta_2$ are used in the mixer block s2, this is equivalent to forwarding the original signal from the block s4 and the signal with delay $|\delta_1 - \delta_2|$ to said mixer, and thus this scenario is not further considered.

Hereafter, the short delay line refers to delays much less than one period of any $\omega_{nm}$, and the long delay line refers to all other delays. In the case of a linear filter or short delay line being used, formula (f3) may be considered as $$f_l(t) = \sum_{n=1}^{N} Q_{ln} \text{Re}(e^{iW_n t} e^{i\beta_{ln}} p_n(t)) = \sum_{n=1}^{N} r_n(t) Q_{ln} \text{Re}(e^{iW_n t + i\beta_{ln} + i\theta_n(t)}), \qquad (f4)$$

because $p_n(t) \simeq p_n(t+\delta_l)$ if $\delta_l$ is much less than any $\omega_{nm}$. Each pair $$(f_{\xi_s^{(1)}}(t), f_{\xi_s^{(2)}}(t)),$$

of these signals (f3), forwarded over a mixer and then over a low-pass filter, is described as:

$$g_s(t) = \sum_{n=1}^{N} Q_{\xi_s^{(1)}n} Q_{\xi_s^{(2)}n} r_n(t+\delta_{\xi_s^{(1)}}) r_n(t+\delta_{\xi_s^{(2)}}) \qquad (f5)$$
$$\{\cos(\beta_{\xi_s^{(1)}n} - \beta_{\xi_s^{(2)}n}) \cos(\theta_n(t+\delta_{\xi_s^{(1)}}) - \theta_n(t+\delta_{\xi_s^{(2)}})) -$$
$$\sin(\beta_{\xi_s^{(1)}n} - \beta_{\xi_s^{(2)}n}) \sin(\theta_n(t+\delta_{\xi_s^{(1)}}) - \theta_n(t+\delta_{\xi_s^{(2)}}))\}.$$

Now consider $$r_n(t+\delta_{\xi_s^{(1)}}) r_n(t+\delta_{\xi_s^{(2)}}) \cos(\theta_n(t+\delta_{\xi_s^{(1)}}) - \theta_n(t+\delta_{\xi_s^{(2)}})), \text{ and} \qquad (f6)$$

$$r_n(t+\delta_{\xi_s^{(1)}}) r_n(t+\delta_{\xi_s^{(2)}}) \sin(\theta_n(t+\delta_{\xi_s^{(1)}}) - \theta_n(t+\delta_{\xi_s^{(2)}})). \qquad (f7)$$

Some terms in (f6) and (f7) may be equal to each other, for example in the case where a small $\delta$ is used, and in other above-mentioned cases. These terms may be enumerated by the index $k=1, \ldots, K$ and assumed as $\lambda_k(t)$, so that equation (f5) transforms to $$g_s(t) = \sum_{k=1}^{K} \hat{h}_{sk} \lambda_k(t), s = 1, \ldots, S_L, \qquad (f8)$$

where $\hat{h}_{sk}$ is constructed as the corresponding terms $$Q_{\xi_s^{(1)}n} Q_{\xi_s^{(2)}n} \cos(\beta_{\xi_s^{(1)}n} - \beta_{\xi_s^{(2)}n}), Q_{\xi_s^{(1)}n} Q_{\xi_s^{(2)}n} \sin(\beta_{\xi_s^{(1)}n} - \beta_{\xi_s^{(2)}n}) \qquad (f9)$$

according to said enumeration of $\lambda_k(t)$.

Taking into account that only $S_L$ pairs of $$(f_{\xi_s^{(1)}}(t), f_{\xi_s^{(2)}}(t))$$

are available, the matrix $\hat{H} = \{\hat{h}_{sk}\} \in \mathbb{R}^{S_L \times K}$ is constructed, with $H = \{h_{ks}\} \in \mathbb{R}^{K \times S_L}$ built as a pseudo-inverse matrix of $\hat{H}$, i.e. $H\hat{H} = I$, where $I \in \mathbb{R}^{K \times K}$ is an identity matrix. The computation of H can be performed on any appliance unit using well-known algorithms based on a singular value decomposition (SVD).

Hence, the set of $g_s(t)$, $s=1, \ldots, S_L$ may be transformed to the set of $\lambda_k(t)$ using just one real-time matrix-by-matrix multiplication block s7 (FIG. 2B):

$$\lambda_k(t) = \sum_{s=1}^{S_L} h_{ks} g_s(t), \forall k = 1, \ldots, K \qquad (f10)$$

and this block may be implemented with digital and/or analog signals.

Figure 2A:
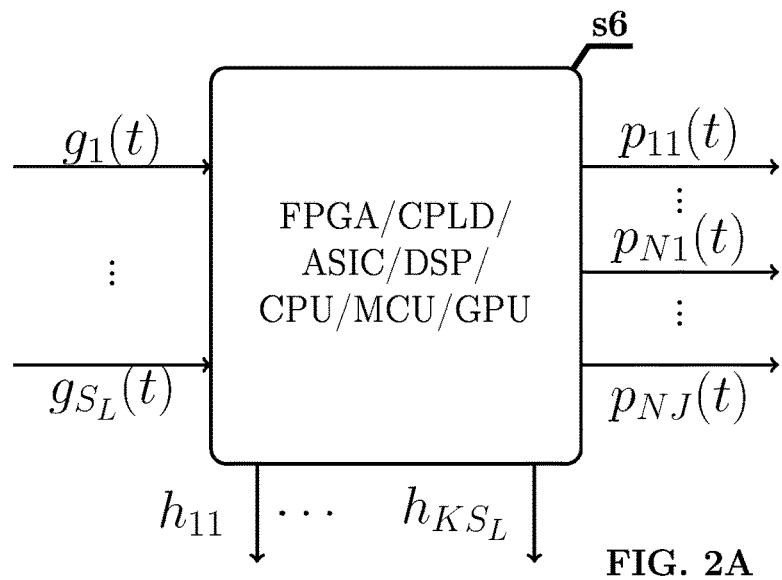
FIG. 2A table $H = \{h_{ks}\}_{k,s=1}^{KS_L}$, spectra responses $p_{nj}(t)$, $n=1, \ldots, N$, $j=1, \ldots, J$, and an estimate of the total number of non-zero-spin isotopes N.
Figure 2B:
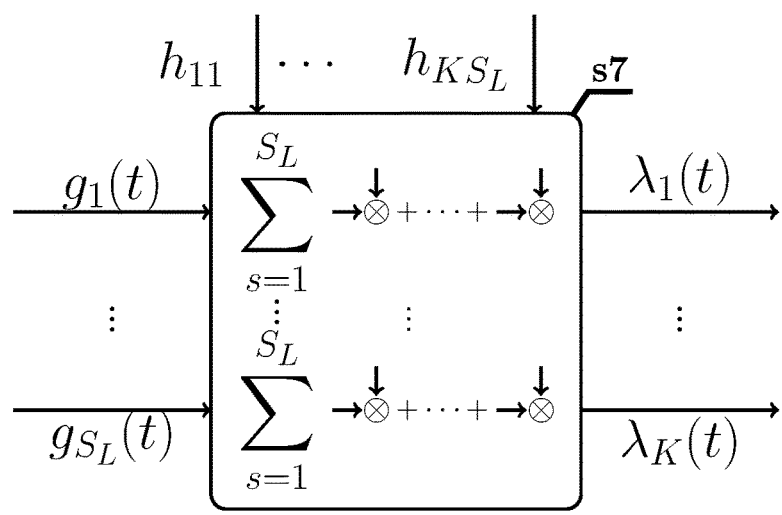
FIG. 2B intermediate data $\lambda_k(t)$, $k=1, \ldots, K$ for further spectrum generation from all non-zero-spin isotopes with reference table H.
Figure 2C:
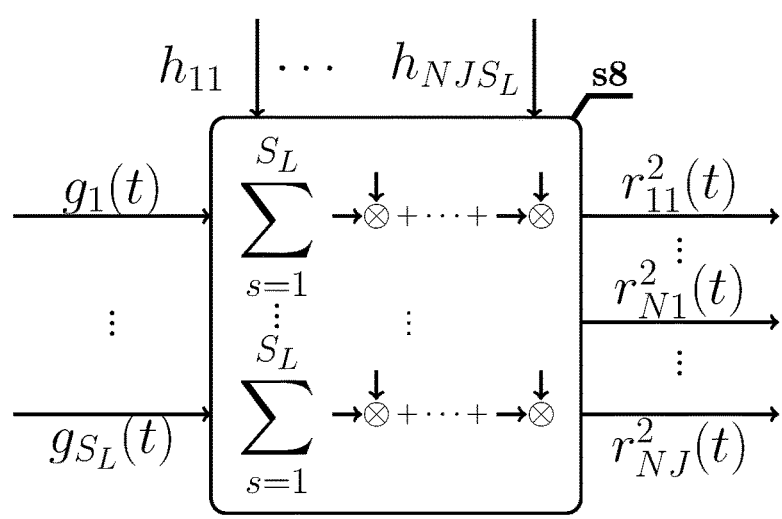
FIG. 2C intermediate data $r_{nj}^2(t)$, $n=1, \ldots, N$, $j=1, \ldots, J$ for further spectrum generation from all non-zero-spin isotopes with reference table H.

In the case where $\lambda_k(t)$ refers to the appropriate term of (f6) on which the s-th pair of (f5) has no long delay lines, $\lambda_k(t)$ refers to $r_n^2(t)$ with corresponding index n and the term (f7) is always equal to zero, so the set of $g_s(t)$, $s=1, \ldots, S_L$ is transformed to the set of $r_{nj}^2(t)$ by one real-time matrix-by-matrix multiplication block s8 as is demonstrated in FIG. 2C.

Hence, by this construction, $r_n(t)$
is weakly dependent on fluctuations in the permanent magnetic field,
is generated with several microsecond delays after the initial signal appears,
already contains enough information for MRI and can be transformed to pure NMR spectra,
$r_n(t)$ does not require long delay lines and precise oscillators for its generation, and
contains several orders less data than the initial signal in digital form.

Now consider that all $r_n(t)$, $n=1, \ldots, N$ are generated from a subset of $\lambda_k(t)$. Then, the remaining subset of $\lambda_k(t)$, according to definitions in (f6) and (f7), has only the unknown terms $$\cos(\theta_n(t+\delta_{\xi_s^{(1)}}) - \theta_n(t+\delta_{\xi_s^{(2)}})) \text{ and} \qquad (f11)$$
$$\sin(\theta_n(t+\delta_{\xi_s^{(1)}}) - \theta_n(t+\delta_{\xi_s^{(2)}})),$$

of which $\theta_n(t)$ may be computed by several arithmetic operations involving arcsin and arccos, and/or approximated by well-known least-squares or total least-squares minimization methods.

The generation of $\theta_n(t)$ (but not $r_n(t)$) is dependent on the magnetic field fluctuation and requires long delay lines that usually necessitate crystal oscillators.

When at least two different non-zero-spin isotopes and at least two receiving coils are available in the investigation area and both isotope responses affect the input signal, the magnetic field fluctuation is computed so that all pure isotope spectra are resistant to magnetic field fluctuations.

To do this, consider that $\tilde{O}_{inj}(t)$ is computed for all non-zero-spin isotopes (n=1, ..., N), all receiving coils (j=1, ..., J), and for several repetitions (i=1, ..., I). The repetitions are collected for the same mixture from all receiving coils, but over different time durations.

Consider that the NMR receiving coils are made of different non-zero-spin isotopes; the NMR spectra of these coils are measured. This measurement may be done once upon calibration of the device, without any substance/mixture for measurement.

Consider that these spectra are computed and stored at $$\hat{p}_{nj}(t) = r_{nj}(t) e^{i\hat{\theta}_{nj}(t)}. \tag{f11}$$

Since the fluctuation of the magnetic field during measurement is random, but the fluctuation of the magnetic field of each isotope spectrum is the same, if collected simultaneously the following minimization may be considered:

$$\min_{\psi_n(t),\varepsilon_i(t)} \int \sum_{i,n,j} \|\tilde{\psi}_{inj}(t) - (\hat{\psi}_{nj} + \psi_n(t))\varepsilon_i(t)\|_2^2 dt \tag{f12}$$

$$\psi_n(t) = e^{i\theta_n(t)}, \tilde{\psi}_{inj}(t) = e^{i\tilde{\theta}_{inj}(t)}, \hat{\psi}_{nj}(t) = e^{i\hat{\theta}_{nj}(t)}, \varepsilon_i(t) = e^{i\epsilon_i(t)},$$

where $\theta_n(t)$ is the pure phase without fluctuation and $\epsilon_i(t)$ is the fluctuation of the magnetic field in the i-th measurement. An algorithm to compute $\theta_n(t)$ according to the minimization of (f12) is described in Appendix 1.

Hence, this approach provides a robust method for obtaining pure spectra including phase with good accuracy for any substance or mixture, even if the measured material contains only one non-zero-spin isotope.

A power series of large delay lines, based on $\delta, 2\delta, 4\delta \ldots$ with dozen of entries, and $$\delta \simeq \frac{1}{100} \min_{nm} \omega_{nm}^{-1} \tag{f13}$$

is suggested as a good working example, but any other series of large delay lines with a similar range and distribution of $\delta$ may also provide appropriate results.

Alternatively, one or several periods of input signals of length (f13) may be stored and used several additional times to generate stored signal in digital and/or analog form for different $\delta$ upon the arrival of an input signal.

Consider that $\delta^{-1}$ is roughly equal to the cutoff frequency of the low-pass filter s3, and during $\delta$ time the signal can be stored. Then several (not more than 20) storing blocks numbered sb=1, ... are allocated, and each period of time of length $\delta$ is counted with the counter cnt=0, .... Then, if the condition cnt&((1<<sb)-1)==0, written according to C-language notation, is true, the current signal is stored into the sb-th block. Each time, all stored blocks are used as $f_i(t)$ signals in the input of s2 (FIG. 1). This drastically saves component counts and allows the implementation of a robust and stable scheme for the computation of $\theta_n(t)$.

Many other techniques for generating $\delta$ may be used to provide a good balance between hardware resources and the total number of different $\delta$ values, which are determined by each particular implementation case.

To improve numerical stability during the computation of $\theta_n(t)$, the total least squares method or the following least squares method are suggested:

$$\min_{\theta_{n_k}(t)} \int \sum_k \begin{array}{l} \|\lambda_k(t) - r_{n_k}(t+\zeta_k^{(1)}) r_{n_k}(t+\zeta_k^{(2)}) \\ \{\eta_k^{(1)} \cos(\theta_{n_k}(t+\zeta_k^{(1)}) - \theta_{n_k}(t+\zeta_k^{(2)})) + \\ \eta_k^{(2)} \sin(\theta_{n_k}(t+\zeta_k^{(1)}) - \theta_{n_k}(t+\zeta_k^{(2)}))\}\|_v^v \end{array} dt \tag{f14}$$

in any v-norm $\|.\|_v$, with $1 \leq v \leq \infty$, where $\eta_k^{(1)}=1$ and $\eta_k^{(2)}=0$ if the cos term of (f6) is used, $\eta_k^{(1)}=0$ and $\eta_k^{(2)}=1$ if the sin term of (f7) is used, $\zeta_k^{(1)}$ and $\zeta_k^{(2)}$ are corresponding delays in long delay lines in (f6) and (f7), and $n_k$ is the corresponding index of the n-th isotope in the $\lambda_k(t)$ term in (f6) and (f7).

There are many possible methods for choosing linear filters or delay lines, and for how the sequences of said linear filters and delay lines are forwarded to the mixers. The best implementation depends on hardware availability and properties. Larger numbers of linear filters or mixers may provide better signal stability. During the construction of blocks s1 and s2, the parameters of these blocks should provide entries for matrices H and $\hat{H}$ in such a way that the full numerical rank of H (and $\hat{H}$) must be greater than or equal to the total amount of different non-zero-spin isotopes situated in the investigated/measurement area. The matrix $\hat{H}$ (and H) should be as close as possible to the identity matrix to save hardware resources during the implementation of blocks s1 and s2, and to provide numerical stability and accuracy.

Every signal in f, g, r, $\lambda$ and h in the described method may be analog or digital. At any point in the process between blocks s1, s2, s3, s4, s5, s6, s7, s8, one or several analog to digital converters (ADCs) and/or one or several digital to analog converters (DACs) can be incorporated to convert between signal types. Any of the blocks s1, s2, s3, s5, s7 and s8 can be implemented through analog and/or digital means. In each particular case, the use of digital, analog, or a mix of digital and analog signals is dependent upon component counts, costs, accuracy, average signal frequency, and many other factors.

Additional attention should be given to the use of digital signals in blocks s1 and s3. Linear filters of digital signals may be implemented with finite difference, weighted sum methods, or linear subspace methods applied to the signals that are discretized in a time domain, including numerical approximation and numerical rounding-off. In this patent application, this type of approximation, i.e. finite difference, weighted sum methods, linear subspace methods, and other similar methods are considered in parallel to the linear filters and delay lines and deliver the results in a manner that is approximately equal to results achieved by linear filters and delay lines.

One additional feature of the ELEGANT NMR method stems from the generation of the table $H=\{h_{ks}\}$ during measurements, as is proposed in FIG. 2A at block s6 according to the solution of the minimization problem:

$$\min_{N, Q_{\xi s}^{(1)}{}_{n_k}, Q_{\xi s}^{(2)}{}_{n_k}, \beta_{\xi s}^{(1)}{}_{n_k}, \beta_{\xi s}^{(2)}{}_{n_k}, r_{n_k}(t), \theta_{n_k}(t)} \quad \text{(f15)}$$

$$\int \sum_{s=1}^{S_L} \left\| g_s(t) - \sum_{k=1}^{K} \hat{h}_{sk} \lambda_k(t) \right\|_v^v +$$

$$\sum_{k=1}^{K} \left\| \lambda_k(t) - r_{n_k}(t+\zeta_k^{(1)}) r_{n_k}(t+\zeta_k^{(2)}) \{\eta_k^{(1)} \cos(\theta_{n_k}(t+\zeta_k^{(1)}) - \theta_{n_k}(t+\zeta_k^{(2)})) + \eta_k^{(2)} \sin(\theta_{n_k}(t+\zeta_k^{(1)}) - \theta_{n_k}(t+\zeta_k^{(2)})) \} \right\|_v^v dt$$

in any v-norm $\|.\|_v$, with $1 \leq v \leq \infty$ taking into account (f9). This particular type of minimization is unknown in general, but many similar algorithms based on the multidimensional decomposition proposed by Harshman in 1970 are known. A scientific theory for the unique solution of this decomposition was introduced by Kruskal in 1977, and many similar applications including NMR have already been discussed in the work of Sidiropolis (2001), Ibragimov (2002), Tugarinov (2005), and Hiller (2009). Thus, together with analytical gradient generation methods proposed by the authors in 2017, the problem (f10) may be solved. The theory of a solution based on alternating least-squares (ALS) iterations is clearly described in the chapter "sparse three-way decomposition" of Ibragimov (2002).

The method (f15) may be used in the following cases:
if only a few mixers are available in s2, and/or
if a set of isotopes in the measurement area is changed, and/or
to improve the accuracy of generated data.

The ELEGANT NMR may be additionally used for any single- and multi-band signals in applications other than NMR and MRI.

NMR Signal Processing with Many Input Coils

A method comprising long delay lines and/or resonators provides a very robust and simple solution for obtaining pure spectra from all non-zero-spin isotopes, but long delay lines and resonators often require more complicated and expensive hardware. In addition, the spectra appear only with certain time delays, caused by processing the long delay line. Hereafter, systems without long delay lines are preferably considered, while taking into account that long delay lines and/or the method described in FIGS. 3-4 will improve results if their usage is possible with available hardware.

The embodiments discussed above are applicable for one or several input signals; however, up to now, mainly the cases with exactly one input signal have been discussed. Two primary situations where several input signals are available are as follows:
one or more receivers perform measurements of a continuous process, and during this process, the relative response spectrum may change, so that the j-th entry refers to the j-th measurement in time (FIGS. 5 and 7); and
each j-th receiving coil generates its own data $r_{nj}(t)$ or $g_{sj}(t)$ with different response spectra (FIGS. 6 and 8).

Different response spectra may occur in the following cases:
a continuous chemical process (chemical synthesis) is measured, and the relative concentrations of substances may change over time;
measurements occur in a detector for liquid chromatography, HPLC, or uHPLC;
measurements occur through multi-dimensional NMR experiments, such as NOESY and multidimensional NMR spectrometry;
an array of detectors is used for MRI, where each detector is situated in its particular place and receives a linear combination of responses from the excited area.

Hence, all embodiments mentioned above deliver several sets of $r_{nj}(t)$ or $g_{sj}(t)$, and each of these sets has similar spectra with variations in amplitudes $A_{nm}$ and phases $b_{nm}$, and these sets are obtained from s15 or s19 sequentially or simultaneously in time.

Assume an index $j=1, \ldots, J$ refers to the number of sets in these experiments (FIGS. 5-8).

Figure 5:
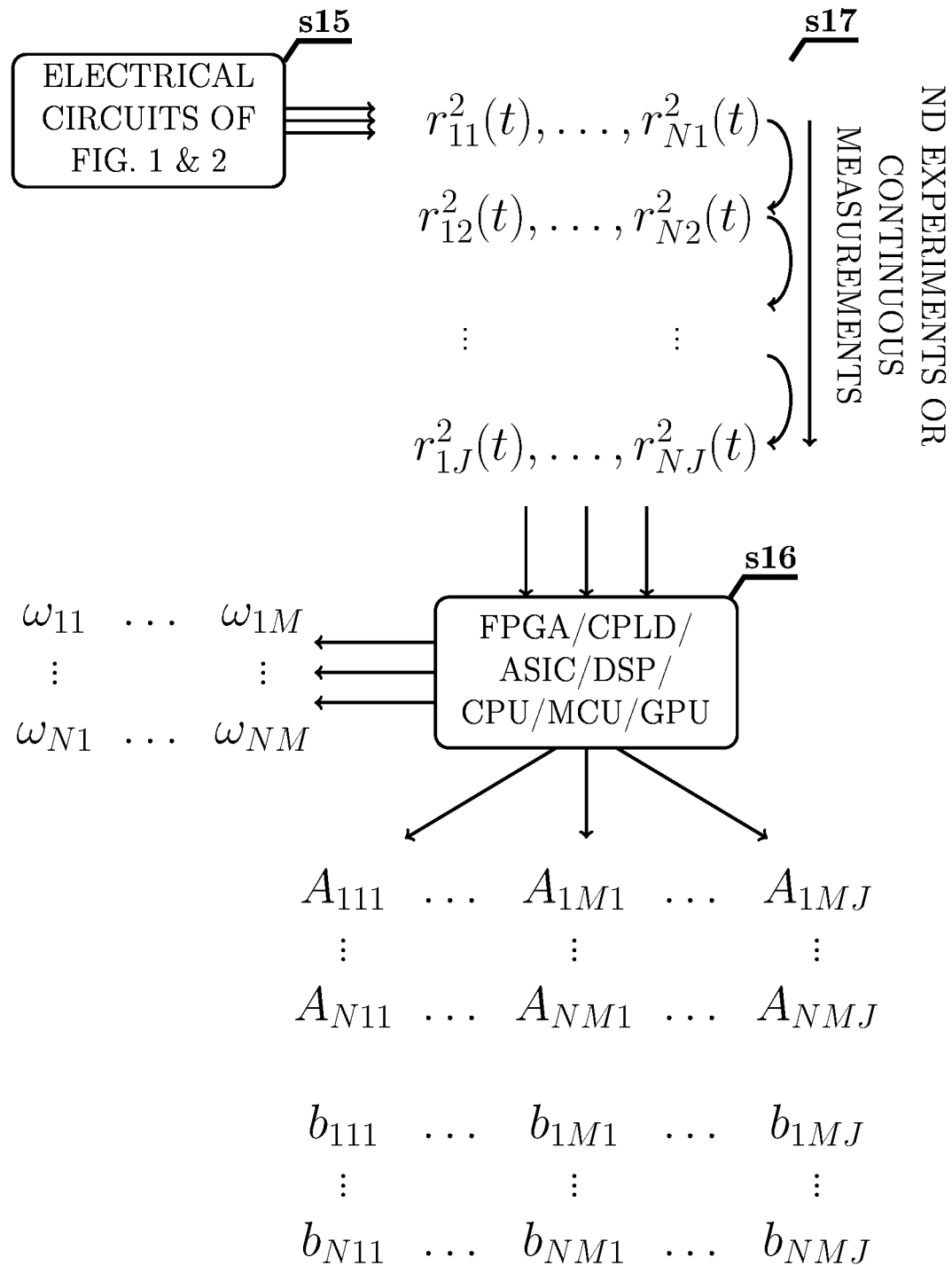
FIG. 5: A processing method to convert a set of continuously measured experiments delivering $r_{nj}^2(t)$, $n=1, \ldots, N$, $j=1, \ldots, J$ from one (or one set of) NMR receiver(s) by collecting several measurements and solving a minimization (f16) using computational unit s16.
Figure 6:
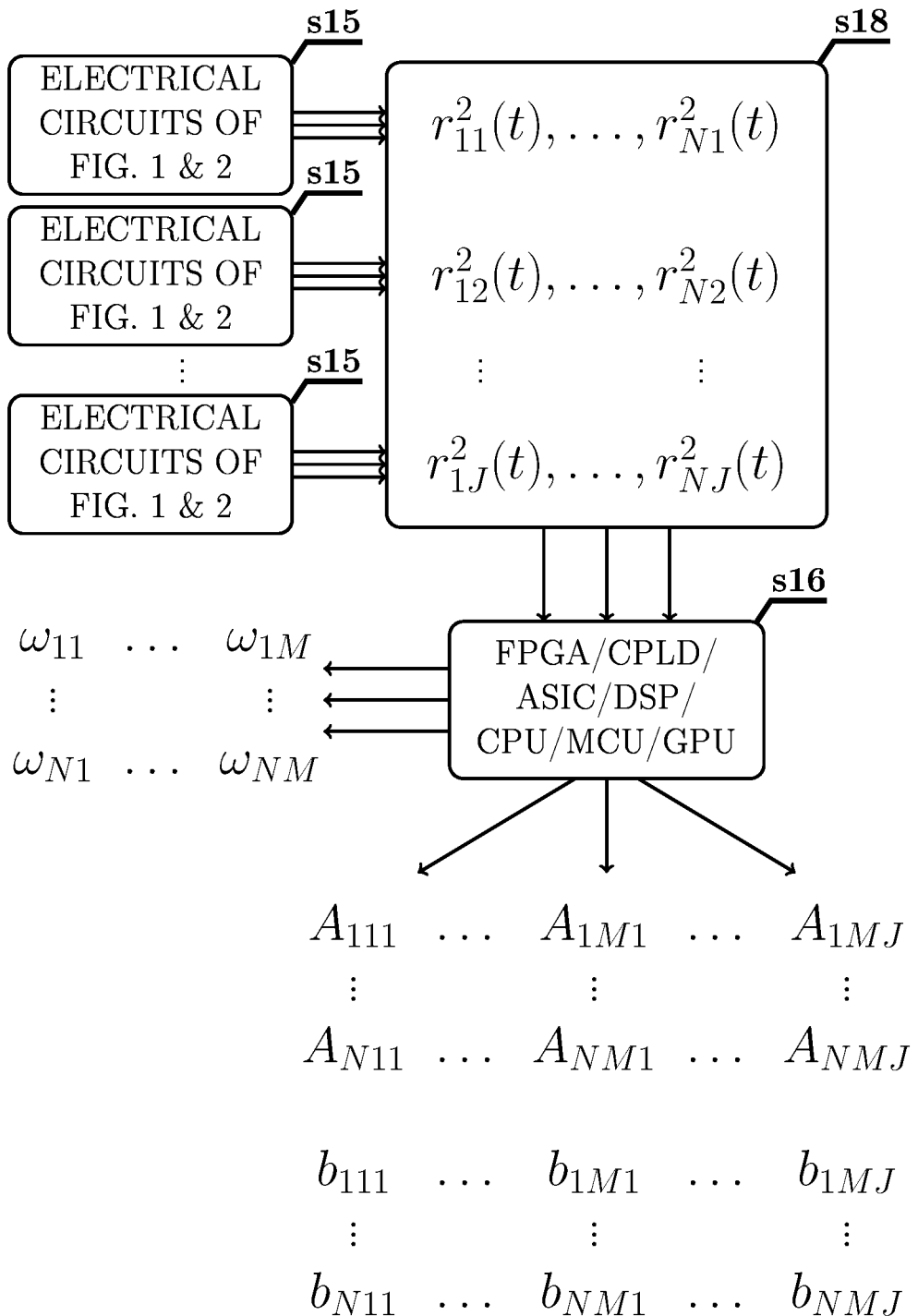
FIG. 6: A processing method to convert a set of simultaneously measured experiments delivering $r_{nj}^2(t)$, $n=1, \ldots, N$, $j=1, \ldots, J$ and solving a minimization (f16) using computational unit s16.

Joint usage of several stored signals $r_{nj}(t)$ by the computational block s16 generates pure resonance frequencies $\omega_{nm}$, amplitudes $A_{nm}$, and phases $b_{nm}$, as well as $A_{jnm}$, $b_{jnm}$ variations along the j-th direction. This solution may be obtained by:

$$\min_{A,b,\omega} \sum_n \sum_j \int_{-\infty}^{+\infty} \left\| r_{jn}(t) - \sum_{m=1}^{M_n} A_{nmj} e^{ib_{nmj}} e^{i\omega_{nm}t} \right\|_v^v dt \quad \text{(f16)}$$

in any v-norm $\|.\|_v$, with $1 \leq v \leq \infty$ as is demonstrated in FIGS. 5 and 6.

Figure 7:
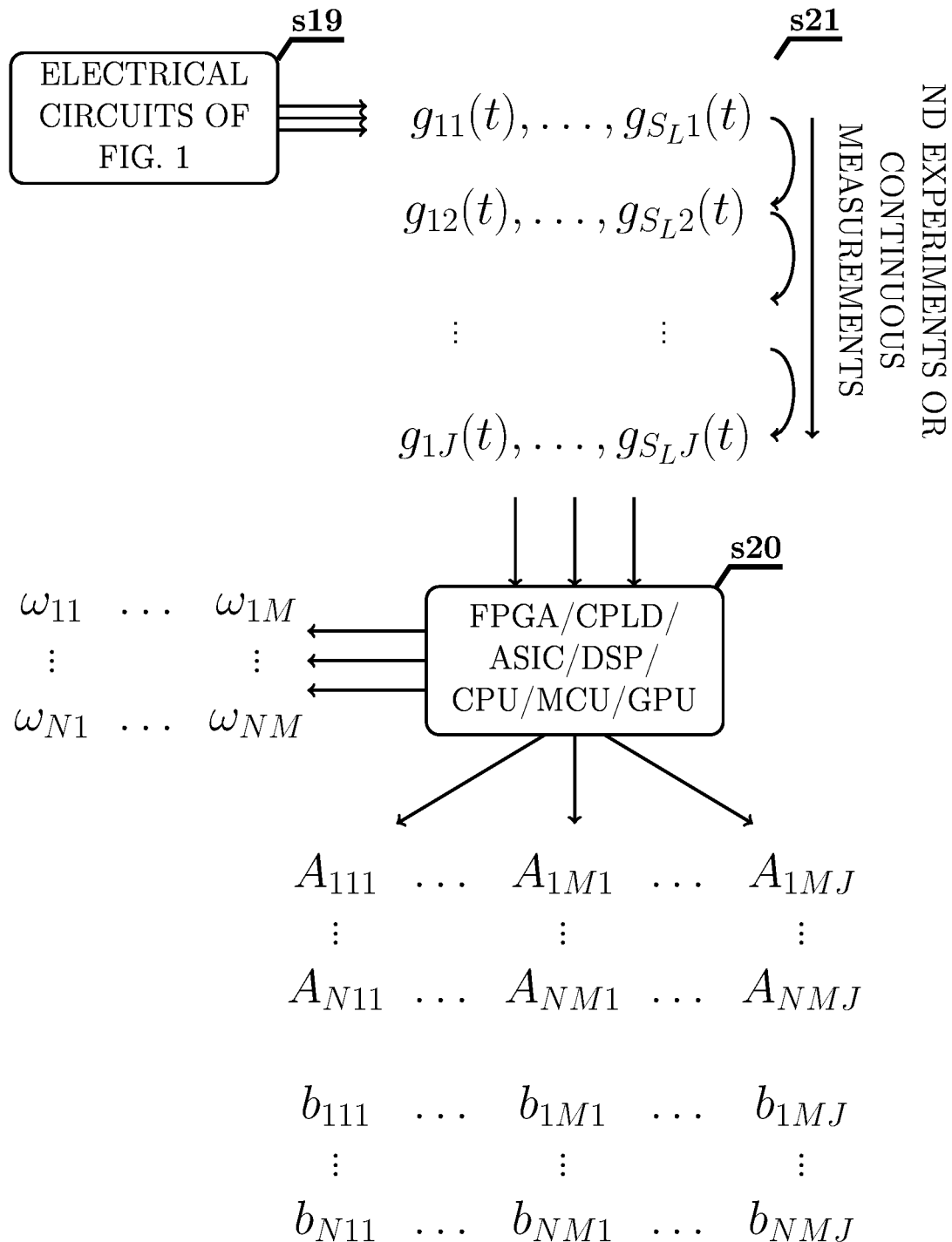
FIG. 7: A processing method to convert a set of continuously measured experiments delivering $g_{sj}(t)$, $s=1, \ldots, S_L$, $j=1, \ldots, J$ from one (or one set) of NMR receiver(s) by collecting several measurements and simultaneously solving minimizations (f15) and (f17) using computational unit s20.
Figure 8:
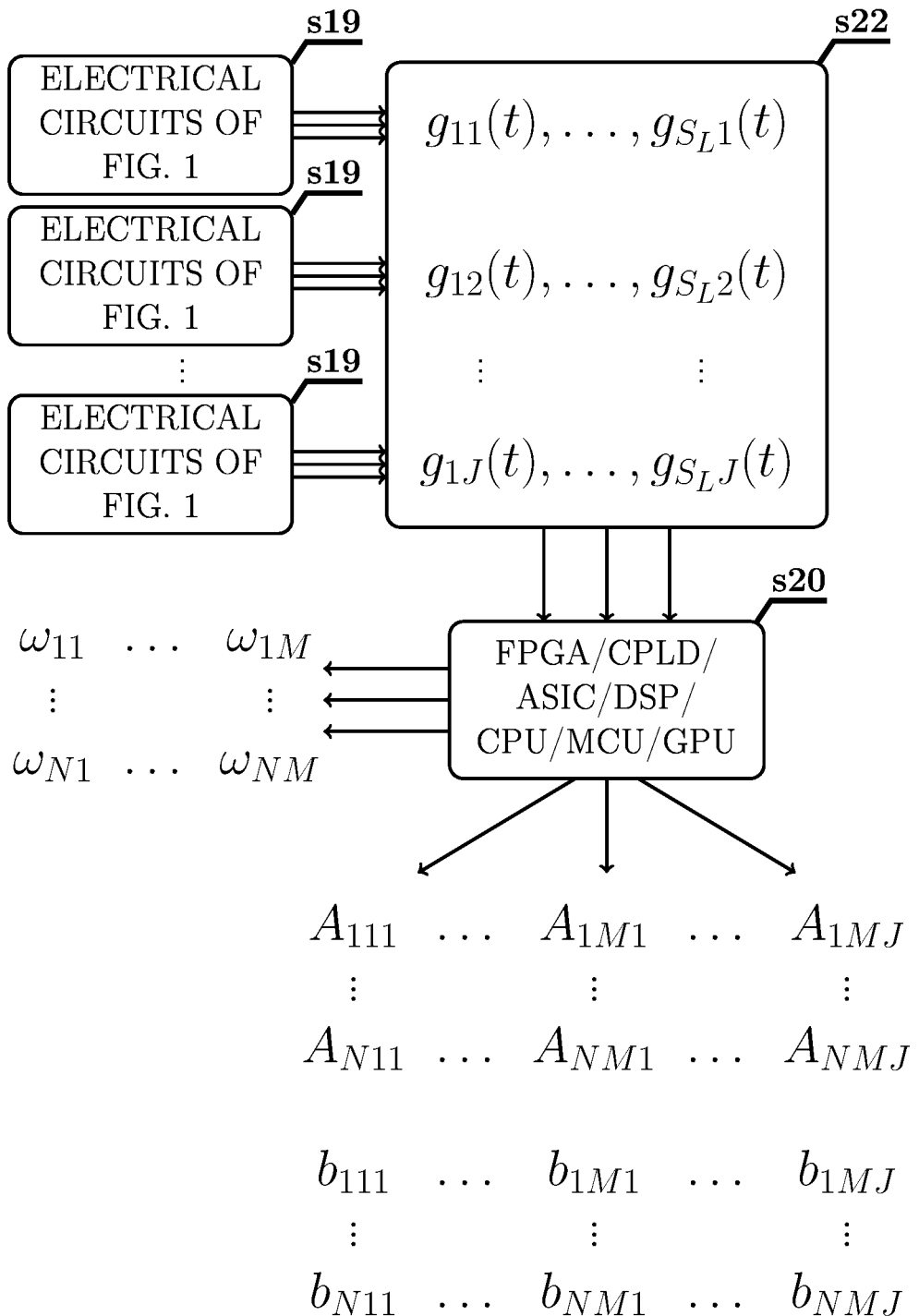
FIG. 8: A processing method to convert a set of simultaneously measured experiments delivering $g_{sj}(t)$, $s=1, \ldots, S_L$, $j=1, \ldots, J$ and simultaneously solving minimizations (f15) and (f17) using computational unit s20.

Joint usage of several stored signals $g_{nj}(t)$ by the computational block s20 generates pure resonance frequencies $\omega_{nm}$, amplitudes $A_{nm}$, and phases $b_{nm}$, as well as $A_{jnm}$, $b_{jnm}$ variations along the j-th direction. This solution may be obtained by:

$$\min_{A,b,\omega} \sum_n \sum_j \int_{-\infty}^{+\infty} \left\| r_{jn}(t) e^{i\theta_{jn}(t)} - \sum_{m=1}^{M_n} A_{nmj} e^{ib_{nmj}} e^{i\omega_{nm}t} \right\|_v^v dt \quad \text{(f17)}$$

in any v-norm $\|.\|_v$, with $1 \leq v \leq \infty$ by joint minimization with (f15), as is demonstrated in FIGS. 7 and 8.

These minimization problems are solved by standard and robust least-squares minimization methods that nowadays available in many textbooks (for example, "Numerical Optimization" by Nocedal, Springer, USA, 2006, 664p), preferably with the accelerations discussed in the authors' work of 2017. Its general theory and data flow chart were discussed in the 2002 paper by Ibragimov.

The methods described above generate $g_s(t)$ and $\lambda_n(t)$ in real time with deterministic delays of only a few microseconds between s4 and s7 or s8. However, the generation of pure resonance frequencies $\omega_{nm}$, amplitudes $A_{nm}$, and phases $b_{nm}$ requires some unpredictable delays, because either
the numerical iterative approach is used in s16 or s20, where (f16) or (f17) is solved, or,
one must wait until the necessary data are collected for s17 or s21.

Real-Time MRI

To overcome the problem of unpredictable delays in a spatially non-homogeneous case (for example, MRI), the following processing method is suggested. Suppose all receivers are situated at their particular places. Then, each coil s4 receives a linear combination of many electromagnetic responses from excited mixtures with shifted phases and attenuation related to the distance that the electromagnetic waves travel before being absorbed by the receiver coil. In this circumstance, signals in s1 remain linear combinations with the same coefficients, $g_s(t)$ are linear combinations of the original signals, and an enhanced matrix $H=\{h_{kjs}\}$ can be constructed so that $$\lambda_{kj}(t) = \sum_{s=1}^{S_L} h_{kjs} g_s(t). \tag{f18}$$

Thus, the real-time generation of $\lambda_{kj}(t)$ in s7 delivers pure NMR spectra from each electromagnetic source, i.e. the 3D magnetic resonance image of the investigated object.

The key advantage of this approach is in the low count of linear filters, delay lines, and mixers to be used, in comparison to the total amount of said components needed to implement all independent schemes (10) for each receiving coil and then perform a standard MRI reconstruction algorithm.

To get the best possible configuration of linear filters, delay lines, and mixers and then determine appropriate coefficients of the matrix H, the following algorithm may be used.

Algorithm Nr. 1:
1. A finite element grid for discretization of the measurement area $FEM1, \ldots, FEM_{NFEM}$ is constructed.
2. The three-dimensional positions of receiving coils are stored in $Coil_1, \ldots, Coil_{NCoil} \in \mathbb{R}^3$
3. A target set of non-zero-spin isotopes for investigations is chosen, for example, $I_n=1, \ldots, NI$: 1H, 13C, 14N, 15N and 31P.
4. A magnetic strength and the corresponding Larmor frequencies for each target isotope and for each finite element are computed according to the permanent magnet composition and magnetization.
5. A coefficient of decay of electromagnetic radiation from each finite element position $FEM_i$ to each receiver coil position $Coil_j$ is computed and stored in $DC_{ij}$.
6. An initial combination of linear filters, delay lines, and mixer connections for all available coils is guessed and stored in a structure S.
7. For each $FEM_i$, $i=1, \ldots, NFEM$ and each particular isotope $I_n$: Assume that only the $FEM_i$ source of electromagnetic radiation is available and has unit value; then the corresponding $g_s(t)$ is computed according to formulas (f1)-(f5) and $DC_{ij}$. The computed function $g_s(t)$ should be transformed to the spectral domain by Fourier transformation into a vector $g_{sx}$, $x=1, \ldots, X$, where x is the discretized index of the spectral domain. The resulting data are stored in $h_{I_n, i, s, x}$ along the x index.
8. Pairs of indexes $I_n$ and i, as well as s and x in the four-dimensional array $h_{I_n, i, s, x}$, should be joined so that the two-dimensional array HH of size (NI*NFEM)× $(S_L*NX)$ is constructed.
9. The condition number of the matrix HH should be computed.
10. Said condition number should be minimized by any standard minimization algorithm according to the variation of the S set.
11. When said optimization converges, the pseudo-inverse of this matrix should be computed, then remapped back to the four-dimensional array. Its x index refers to the appropriate Larmor frequency of the corresponding finite element; the corresponding value should be stored in the three-dimensional array H and used in (f18).

Even through the described algorithm is computationally complex and may require a supercomputer to complete the job, it should need to be performed only one time before the equipment starts operation; the resulting data may be stored for further usage.

Hence, from just one real-time measurement (several milliseconds), the complete MRI image can be reconstructed in only a few milliseconds. This fact opens new possibilities for real-time MRI visualization and guiding.

Real-Time Method for Obtaining Signals from Repeating Processing Method

To illustrate this method, consider one practical example where it may be used. Suppose a surgical operation is intended. However, instead of a real human surgeon, a surgical robot will perform this operation.

The patient and the patient's organs may react to the pain in about 0.1 s, so the surgical scalpel should be accurate and situated with feedback control requiring much less than this 0.1 s period. Sensors that measure the scalpel and patient body configurations should report their data much faster, with the delay being no more than several milliseconds.

The mechanical system of the surgical robot is fast, and can move its tools (i.e. the scalpel) quickly enough that any arbitrary configuration is achievable in several milliseconds.

However, the numerical computation of mechanical movements according to the responses of these sensors and information about the operation are so complex that a state-of-the-art appliance unit requires several seconds to complete the computation, ruining any possibility of performing this operation in real time.

Said appliance unit is affordable and compact in size, so thousands of appliance units may be installed in a hospital. However, their computations cannot be parallelized in such a way that the computations will always complete in several milliseconds. Therefore, it is dangerous to apply this straightforward solution in a real environment.

The proposed method provides a real-time and deterministic response, so that the surgical robot can determine its next action in real time or can promptly stop a harmful action if the surgical robot does not have enough information on what it should do next.

Hence, this example will demonstrate how to construct a processing method that may react in real time based on information obtained from one or several sensors.

Figure 9:
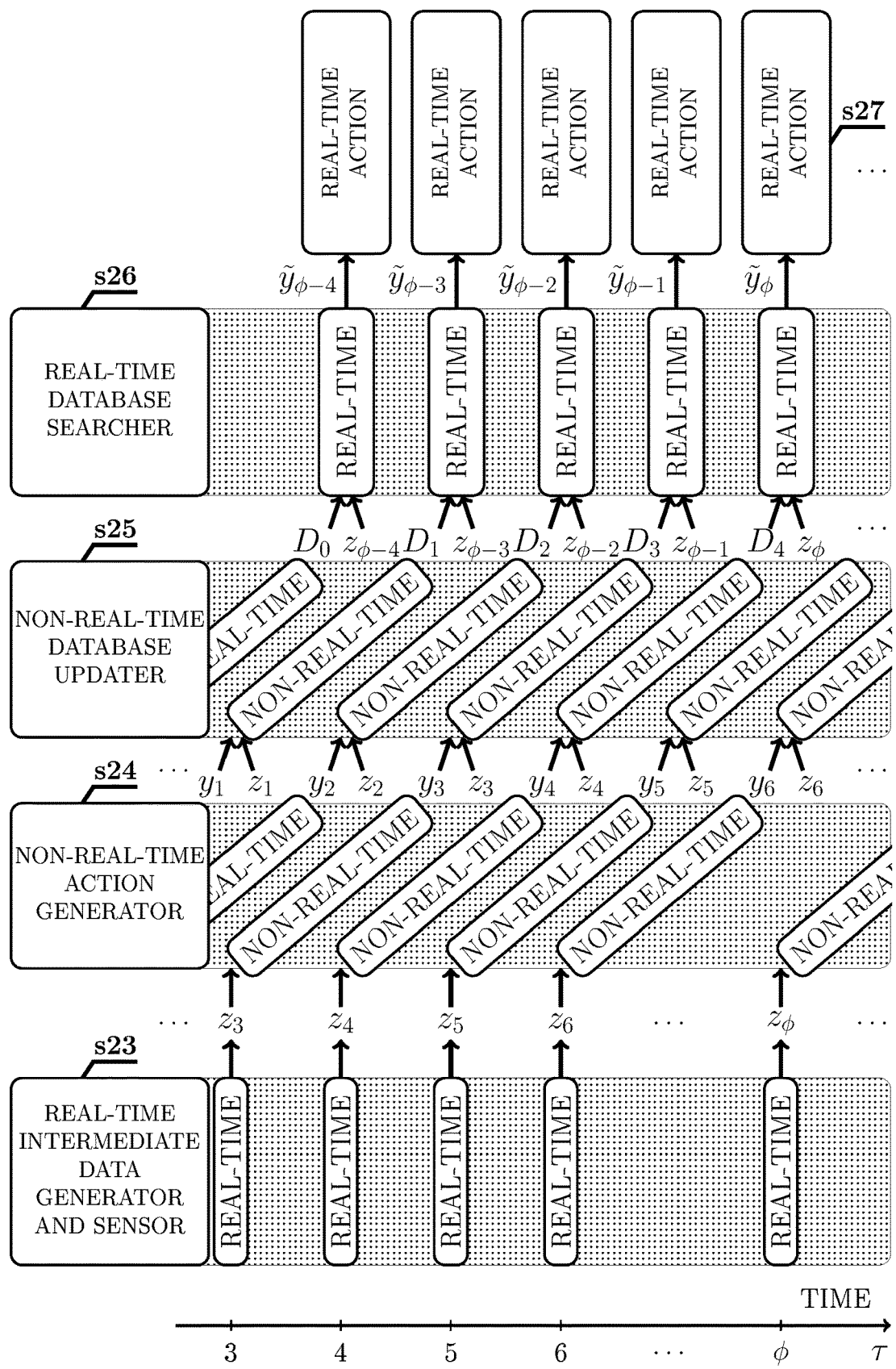
FIG. 9: A real-time database method.

A brief scheme of this real-time method is described in FIG. 9. All involved processes operate in time slots, hence each is marked with its so-called 5-th time step.

The method (ALGORITHM Nr. 2) is comprised of the following four parts:

Component 1. A Real-Time Intermediate Data Generator and Sensor s23.

This may be any chemical or other sensor that measures some physical and/or chemical properties. The sensor should deliver measurement data in real time, i.e. with deterministic delay such that the length of this delay is below the acting time of the total system. At each time step, this block delivers said intermediate data set $z_\varphi$. This data set is usually digital and is represented as an array of digits.

Component 2. Non-Real-Time Action Generator s24.

This block receives data $z_\varphi$ upon its availability and performs a computation. The result of this computation is a special data set $y_\varphi$ that can be used in block s27 to perform a real-time action, or a parametric data set that may be used in block s27 to generate and perform a real-time action. Computational time for this step is unpredictable. The computation may be interrupted if it takes too much time. To be able to complete computations for most of the input data that arrives at each time step, one or several computational units can work in parallel. When new data ($z_{\phi+1}$) arrives, it is assigned to the first free appliance unit. If no free units are available, either the next-arriving data is skipped or the oldest ongoing computation over all appliance units is discarded and this free unit is allocated to the new data set $z_{\phi+1}$.

In the example above, the surgical robot generates how it should behave, i.e. how to set its motors and actuators for the current patient configuration, for example, breathing. These computed results may be reused later when the patient re-enters the same predictable configuration.

Component 3. Non-Real-Time Database Updater s25.

This block receives a pair of data sets, $z_\phi$ and $y_\phi$, when both are ready and incorporates them into a database D. The database containing already-incorporated data sets from time steps 1, . . . , $\phi$ is abbreviated as $D_\phi$.

This database may be organized by many different methods. Most importantly, the database should possess the property of searching its entries in real time, within a deterministic amount of time.

Similar to the step for the non-real-time action generator, the computational time for this step may be unpredictable. The computation may be interrupted and this data set discarded if the computation takes too much time. To be able to complete computations for most of the input data that arrives at each time step, one or several computational units working in parallel may be constructed and perform the same way as in component 2.

In the example above, the surgical robot collects data from sensors for all possible configurations of patient's body during the patient's breathing and moving periods and stores these configurations in the database, i.e. "learning" patient behavior and "learning" how to perform the surgical operation.

Component 4. Real-Time Database Searcher s26.

This block receives the actual intermediate data $z_\phi$ from the real-time intermediate data generator and sensor, and searches and matches this data against the actually available database. Normally, the database that is available for this moment contains only entries that are far behind in time, i.e. the database $D_{\phi-k}$, with k>>1. In the case where matching of $z_\phi$ occurs, the corresponding vector ỹ is delivered. When no match is found, then no answer is delivered. By construction, if the database is trained on appropriate data in the previous steps, this matching delivers a real-time response and bypasses the intensive calculations which have unpredictable computational times.

Hence, most deep learning algorithms, and/or support vector machine algorithms, and/or low rank approximation and linear subspace methods may be used for the construction of this database, with the restriction that searching and matching in the database is always a deterministic process.

Matching of test data against an established database may be performed by
  exact match,
  approximate match in least-squares or any other suitable norm,
  match to a linear combination of two or several datasets, so that the resulting vector y is the linear combination of appropriate y vectors to z vectors.

In the example above, in the case of the surgical robot being sufficiently trained, it performs real-time actions without any help from a human surgeon and can be much more precise and accurate.

As the real time action, we propose to perform crossection In addition, the physical position of the cross-section point is determined by a distribution of medicaments/pharmaceuticals with predetermined non-zero-spin nuclei that are injected and/or ingested by the patient and then physically distributed through tissues.

Thus, execution of real-time actions according to arbitrary real-time responses from sensors is demonstrated, with a wide range of potential chemical compositions and spatial configurations detectable by those sensors in time-critical applications. Many other useful applications of these results may be easily outlined, and are discussed in the following subsections.

Real-Time Chemical Switch

Consider that measurements are performed on a production line, where one or several concentrations of substances play an important role, and some devices/valves should be switched if the concentration of one or several substances goes outside of predetermined boundaries. Usage of the suggested method solves this problem: if measurement and database construction are performed, one can monitor desired substances and/or mixtures in real time. If matching by s26 occurs, the switch takes place.

NMR Signal Processing with Correlated Resonators

In the case of a resonator or internal clock being used with the NMR processing method, the following approach is suggested.

Figure 3:
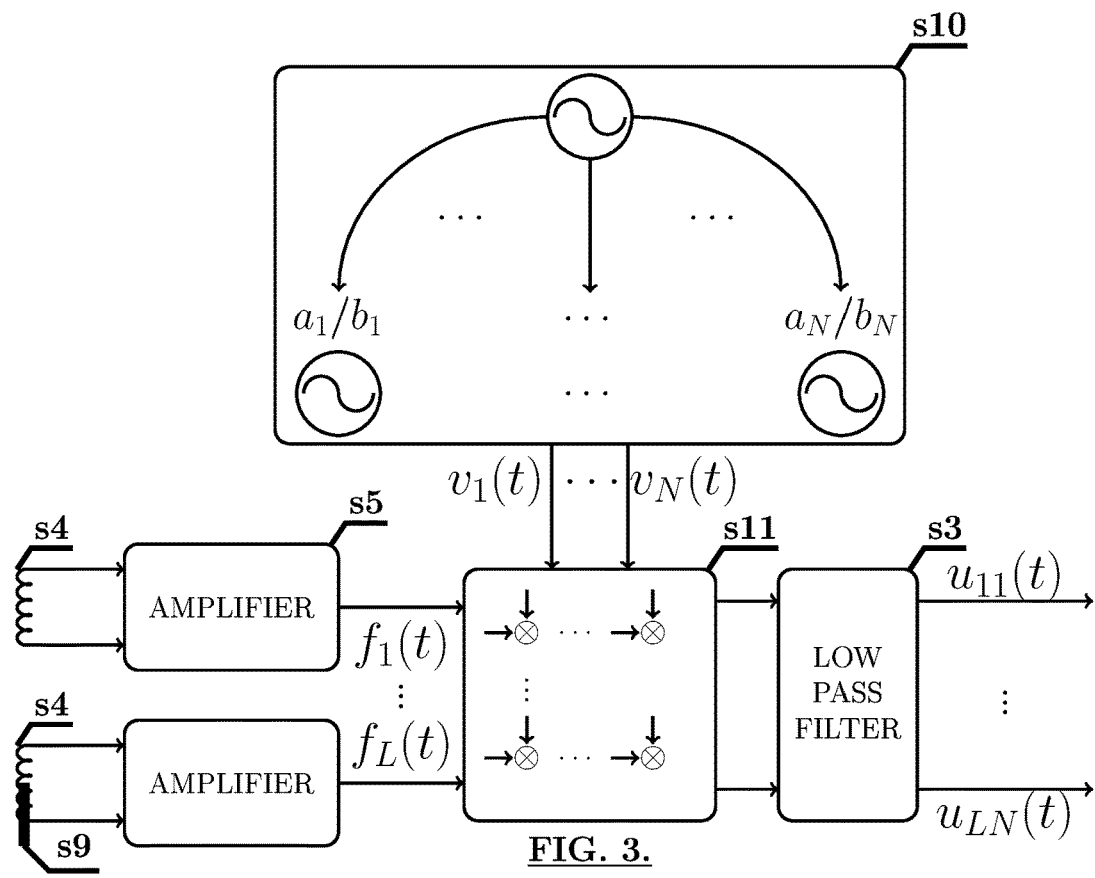
FIG. 3: A processing method to convert wide-band NMR signals s4 with correlated oscillators s10.

Consider FIG. 3: One or several wide-band coils and/or optical detectors s4 receive very weak signals that are usually amplified by one or more sequential amplifiers s5. The signals are abbreviated as $f_l(t)$, l=1, . . . , L, where L is the total count of input signals and t is the time domain variable of the measurements. Based on a priori information about the magnets and non-zero-spin isotopes in use, one or several frequency generators s10 and their signals, delayed by 1/4 period, are used. Signals from said frequency generators are abbreviated as $v_n(t)$, n=1, . . . , N, so that $v_n(t)$ is a complex function whose real part refers to the signal and whose imaginary part refers to the delayed signal from the same generator.

All $f_l(t)$, l=1, . . . , L signals are forwarded pairwise with $v_n$=1, . . . , N to the mixer block s1, so that each pair is comprised of one f and one s signal. The resulting signals from each mixer are forwarded over a low-pass filter s3 and abbreviated as $u_{ln}(t)$, where l is the index of the input NMR coil and n is the index of the frequency generator.

This method is nowadays well-known and used in many NMR devices; however, the following key differences to prior-art methods are suggested:

Statement 1: All generators $v_n(t)$, n=1, . . . , N are fully correlated to each other, i.e. at any time the frequencies of all generated signals have fixed ratios with one another.

Here, it is sufficient to consider only one input signal s4 (FIG. 3), so that L=1, and only one experiment, so that J=1. Therefore, the l and j indexes are dropped from $u_{lnj}(t)$ and it becomes represented as $u_n(t)$, n=1, . . . , N.

Consider that the input NMR signal is disturbed because an unstable magnetic field and unstable oscillator are used. In this case, this signal can be written as the following form:

$$f(t) = \sum_{n=1}^{N} \mathrm{Re}\big(e^{iW_n t + iW_n \sigma(t) + i\tilde{\sigma}(t)} p_n(t)\big),$$

where σ(t) refers to the function of the unstable magnetic field, and σ̃(t)—refers to the function of the unstable oscillator. In this case $u_n(t)$ reads as:

$$u_n(t) = r_n(t) e^{i\Theta_n(t) + iW_n \sigma(t) + i\tilde{\sigma}(t)}$$

so that $r_n(t)$ can be easily computed as $r_n(t) = |u_n(t)|$.

Some important considerations should be taken into account:
- affordable unstable oscillators do have local stability and are stable for a short period of time (several microseconds and less); however, they may be unstable over longer periods (several milliseconds and more);
- in normal laboratory or industrial conditions, a magnetic field does not fluctuate with high deltas, which only occur in an exceptional cases like close proximity to electromotors, electromagnets, high current switchers, etc; said magnetic field can be stable for a short period of time (several microseconds and less), but it may be unstable over longer periods (several milliseconds and more).

Hence, σ(t) and $\tilde{\sigma}$(t) are considered as either piece-wise constant or piece-wise linear functions that cover said short-period time stabilities of oscillators and magnetic field.

Let us divide $u_n(t)$ and $r_n(t)$, defined on t=[0, T], into several pieces τ=1, ..., Ψ equal in time as:

$$\tilde{u}_{n\tau}(t) = -i\ln\frac{u_n\left(t+\frac{T}{\Psi}(\tau-1)\right)}{u_n\left(t+\frac{T}{\Psi}(\tau-1)\right)}, t \in \left[0, \frac{T}{\Psi}\right], \tau = 1, \ldots, \Psi,$$

$$n = 1, \ldots, N.$$

According to the assumptions of the piece-wise constants σ(t) and $\tilde{\sigma}$(t), it is sufficient to approximate $\tilde{u}_{n\tau}(t)$ as $\theta_{n\tau}(t)$+$W_n\sigma_\tau$+$\tilde{\sigma}_\tau$. Usually the signal $\theta_{n\tau}(t)$ itself is overdetermined and can be adequately approximated by the method of model order reduction as is, for example, described in Jaravine and Ibragimov 2006.

Hence, $\theta_{n\tau}(t)$ is a three-dimensional object formed from n, τ, and t dimensions that may be represented as:

$$\theta_{n\tau}(t) = \sum_{r=1}^{R} \theta_{nr}^{(1)}\theta_{\tau r}^{(2)}\theta_{r}^{(3)}(t), t \in \left[0, \frac{T}{\Psi}\right], \quad (f19)$$

$$\tau = 1, \ldots, \Psi, n = 1, \ldots, N$$

with low rank r compared to N and/or Ψ, and which can be found by solution of one of the following minimization problems, either:

$$\min_{R,\theta_{nr}^{(1)}\theta_{\tau r}^{(2)}\theta_{r}^{(3)}(t),\sigma_\tau,\tilde{\sigma}_\tau} \sum_{n=1}^{N}\sum_{\tau=1}^{\Psi}\int_{0}^{T/\Psi} \left\| \tilde{u}_{n\tau}(t) - \sum_{r=1}^{R}\theta_{nr}^{(1)}\theta_{\tau r}^{(2)}\theta_{r}^{(3)}(t) - W_n\sigma_\tau - \tilde{\sigma}_\tau \right\|_2^2 dt,$$

or $\theta_{n\tau}(t) = \tilde{u}_{n\tau}(t) - W_n\sigma_\tau + \tilde{\sigma}_\tau$, where $$\min_{\sigma_\tau,\tilde{\sigma}_\tau}\int_0^{T/\Psi}\|\tilde{u}_{n\tau}(t) - W_n\sigma_\tau - \tilde{\sigma}_\tau\|_2^2 dt.$$

Both minimization problems can be solved by any method that will find the tensor decomposition of a multidimensional (≥3) object.

A similar method can be applied in the event of using a piece-wise linear approximation instead of the piece-wise constants for σ(t) and $\tilde{\sigma}$(t). This approximation leads to $$\min_{R,\theta_{nr}^{(1)}\theta_{\tau r}^{(2)}\theta_{r}^{(3)}(t),\sigma_\tau,\tilde{\sigma}_\tau} \sum_{n=1}^{N}\sum_{\tau=1}^{\Psi}\int_{0}^{T/\Psi} \left\| \begin{array}{c} \tilde{u}_{n\tau}(t) - \sum_{r=1}^{R}\theta_{nr}^{(1)}\theta_{\tau r}^{(2)}\theta_{r}^{(3)}(t) - \\ W_n\sigma_\tau Y_\tau(t) - \tilde{\sigma}_\tau Y_\tau(t) \end{array} \right\|_2^2 dt, \quad (f20)$$

or $\theta_{n\tau}(t) = \tilde{u}_{n\tau}(t) - W_n\sigma_\tau Y_\tau(t) + \tilde{\sigma}_\tau Y_\tau(t)$, where $$\min_{\sigma_\tau,\tilde{\sigma}_\tau}\int_0^{T/\Psi}\|\tilde{u}_{n\tau}(t) - W_n\sigma_\tau Y_\tau(t) - \tilde{\sigma}_\tau Y_\tau(t)\|_2^2 dt,$$

where $$Y_\tau(t) = \begin{cases} t \in \left[(\tau-1)\frac{T}{\Psi}, \tau\frac{T}{\Psi}\right]: & 1 + t\frac{\Psi}{T} - \tau, \\ t \in \left[\tau\frac{T}{\Psi}, (\tau+1)\frac{T}{\Psi}\right]: & 1 - t\frac{\Psi}{T} + \tau, \\ t \notin \left[(\tau-1)\frac{T}{\Psi}, (\tau+1)\frac{T}{\Psi}\right]: & 0. \end{cases}$$

Hence, we have demonstrated how to stabilize NMR data acquisition and obtain pure spectra that are not disturbed by an unstable magnetic field and/or unstable oscillator.

This condition (statement 1) is sufficient for performing NMR signal processing in a fluctuating magnetic field and/or fluctuating oscillator; however, several additional conditions may improve results and/or be useful for particular cases.

Said conditions may be one of the following: either

Statement 2: at least two repetitions of data acquisition should be performed, or Statement 3: two or more magnetic fields with different strengths should be situated close to one another and cover the measuring unit together with several transmitter and receiver coils, or Statement 4: at least one non-zero-spin isotope with a priori known spectra should be either:
- situated in the measured substance, or
- incorporated as the reference unit inside one or several input coils, or
- incorporated in the walls of the measuring NMR camera.

Consider the first condition (statement 2): at least two repetitions of data acquisition should be performed.

Figure 4:
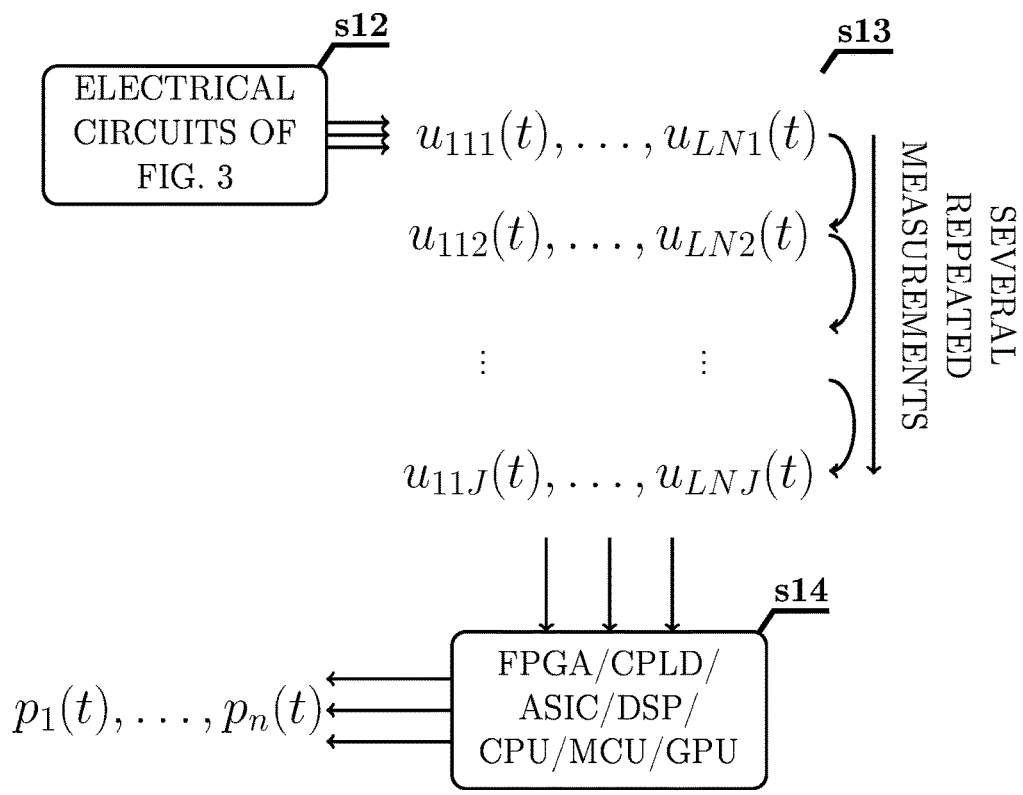
FIG. 4: A processing method to convert a set of continuously measured experiments delivering $u_{lnj}(t)$, $l=1, \ldots, L$, $n=1, \ldots, N$, $j=1, \ldots, J$ from one set of NMR receivers by collecting several measurements, performing (f10) and (f11) transformations, and solving a minimization (f12) using computational unit s14.

Here, the j-th index in $u_{lnj}(t)$, j=1, ..., J refers to the number of experiments that are collected in different time-slots, as is demonstrated in FIG. 4. The total number of input coils working simultaneously may be one or more, so we drop the index 1 from $u_{nj}(t)$, j=1, ..., J, n=1, ..., N. This gives the construction, $$u_{nj}(t) = r_{nj}(t)e^{i\Theta_n(t)+iW_n\sigma_j(t)+i\tilde{\sigma}_j(t)},$$

where $\sigma_j(t)$ refers to functions of the unstable magnetic field and $\tilde{\sigma}_j(t)$ to functions of the unstable oscillator for every particular j-th experiment.

As above, $r_{nj}(t)=|u_{nj}(t)|$. Assuming $$\tilde{u}_{nj}(t) = -i\ln\frac{u_{nj}(t)}{r_{nj}(t)},$$

then $\theta_n(t)$, n=1, ..., N are computed according to the minimization of:

$$\min_{\sigma_j(t),\tilde{\sigma}_j(t),\theta_n(t)}\sum_{n=1}^{N}\sum_{j=1}^{J}\|\tilde{u}_{nj}(t) - \theta_n(t) - W_n\sigma_j(t) - \tilde{\sigma}_j(t)\|_2^2,$$

-continued so that $$\theta_n(t) = \frac{1}{J}\sum_{j=1}^{J}\tilde{u}_{nj}(t) - \frac{\mathcal{H}_0(t)(\mathcal{H}_2 W_n - \mathcal{H}_3) + \mathcal{H}_1(t)(\mathcal{H}_2 - NW_n)}{\mathcal{H}_2^2 - \mathcal{H}_3 N},$$

where $$\mathcal{H}_0(t) = \frac{1}{J}\sum_{j=1}^{J}\sum_{n=1}^{N}\tilde{u}_{nj}(t),\ \mathcal{H}_1(t) = \frac{1}{J}\sum_{j=1}^{J}\sum_{n=1}^{N}\tilde{u}_{nj}(t)W_n,$$

$$\mathcal{H}_2 = \sum_{n=1}^{N}W_n,\ \mathcal{H}_3 = \sum_{n=1}^{N}W_n^2.$$

If instabilities in the magnetic field and/or oscillator are large enough in magnitude, $\sigma_j(t)$ and $\tilde{\sigma}_j(t)$ may run over $2\pi$. In this event, the minimization in the Frobenius norm should be substituted with any similar norm that accounts for the fact that $2\pi c$ is equal to 0 for arbitrary integer c. We suggest substituting (square norm) with the $\sin^2(x/2)$ norm, upon which all above formulas read similarly.

Hence, we demonstrate that if
all generators $v_n(t)$, $n=1, \ldots, N$ are fully correlated, i.e. at any time the frequencies of all generated signals have fixed ratios to one another, and
at least two repetitions of data acquisition are performed, there is a straightforward method for obtaining pure spectra that are not disturbed by the unstable magnetic field and/or unstable oscillator.

Consider the second condition (statement 3). In the event a focused magnetic field is constructed (like in FIGS. 14-18, 24-25) it is easy to perform an experiment where two or more volumes with the substance to be measured are situated in magnetic fields of different strengths. Using two or more transmitter and receiver coils, or appropriately focusing the transmitting energy using the ELMATHRON beam, one can collect two or more spectra of the same isotope (for example H) of the same substance at two or more different magnetic field strengths. Doing so leads to two or more different carrier frequencies being simultaneously measured, and fluctuations in time of the magnetic field and oscillator remain the same ratio for all these simultaneous measurements.

There are two cases possible with this scenario.

Statement 5: If the magnetic field strength differs in order by no more than several percent, then spectra (if excited similarly) can be scaled by the frequency and will be identical. Two such spectra can be used to subtract out oscillator instability.

Statement 6: If the magnetic field strength differs considerably, or if the spectra are generated by different excitation sequences, then they cannot be considered identical; however, if one collects more than two such spectra, they may be approximated with a low rank approximation because the main parts remain similar (dependent on chemical shifts) and what differs is dependent on J-coupling.

The first case (statement 5) has a unique solution if either at least one reference isotope is available or at least two measurements are performed. To find this solution, one needs to outline a minimization problem similar to (f20) and use similar solution methods.

The second case (statement 6) can also be solved with a very similar approach. Let $u_{kn}(t)$, where $k=1, \ldots, K\geq 2$ refers to the index of different magnetic field strengths and/or an excitation pulse sequence experiment. Since spectra for different excitations differ only in the J-coupling part, it is clear that these spectra build a low rank object and, together with the n variable (isotope number), build a three-dimensional object similar to (f19) with minimization problem similar to (f20) and for which similar solution methods can be used.

Now consider the third condition (statement 4): the situation with reference isotope(s). In this case, just one measurement should suffice, so we drop the index j from $u_{ljn}(t)$.

Here the following minimization problem should be solved:

$$\min_{\sigma(t),\tilde{\sigma}(t),p(t)}\left\|u_{ln}(t) - e^{iW_n\sigma(t) + i\tilde{\sigma}(t)}(p_n(t) + q_{ln}(t))\right\|_\nu^\nu,$$

in any $\nu$-norm $\|.\|_\nu$, with $1\leq\nu\leq\infty$, and where $p_{ln}(t)$ are the reference spectra.

This minimization problem has unique solutions in the following cases:

L=1, $p_1(t)$=0, $q_{11}(t)\neq 0$, either $\sigma(t)$=0 or $\tilde{\sigma}(t)$=0 we need to perform one measurement on one coil, need only one reference isotope, and need no such isotope in the measured substance in case either oscillator or magnetic field is unstable; the solutions are:

$$\tilde{\sigma}(t) = 0:\ \forall n = 2, \ldots, N:\ p_n(t) = \left(\frac{q_{11}(t)}{u_{11}(t)}\right)^{W_n/W_1} u_{1n}(t)$$

$$\sigma(t) = 0:\ \forall n = 2, \ldots, N:\ p_n(t) = \left(\frac{q_{11}(t)}{u_{11}(t)}\right)u_{1n}(t)$$

L=1, $p_1(t)$=0, $q_{11}(t)\neq 0$, $p_2(t)$=0, $q_{12}(t)\neq 0$—we need to perform only one measurement on one coil, need only two reference isotopes, and need no such isotopes in the measured substance; the solution reads as:

$$\forall n = 3, \ldots, N:\ p_n(t) = u_n(t)\left(\frac{u_1(t)}{q_1(t)}\right)^k \left(\frac{u_2(t)}{q_2(t)}\right)^{1-k},\ k = \frac{W_n - W_2}{W_1 - W_2},$$

$$L > 1:\ p_n(t) = \frac{q_{l_1n}(t)u_{l_2n}(t) - q_{l_2n}(t)u_{l_1n}(t)}{u_{l_1n}(t) - u_{l_2n}(t)},\ l_1 \neq l_2.$$

Every signal in f, v, and u in the described method may be analog or digital. At any point between blocks s3, s4, s5, s10, s11, s12, s13, and s14, one or several analog to digital converters (ADCs) and/or one or several digital to analog converters (DACs) can be incorporated to convert between signal types. Any of the blocks s3, s10, s11, s12, and s13 can be implemented through analog and/or digital means. In each particular case, the use of digital, analog, or a mix of digital and analog signals is dependent upon component counts, costs, desired accuracy, average signal frequency, and many other factors.

In the output of s3 at FIG. 3, $|u_{ln}(t)|$ refers to $r_{ln}(t)$ and is weakly dependent on fluctuations in the permanent magnetic field and oscillator. It is generated with several microsecond delays after the initial signal appears, so all real-time methods that require only r may be used.

Usage of internal marker(s) for one isotope or a spectrum that may be matched by internal database, together with correlated oscillators, gives a straightforward way to get absolute spectra for all other measured non-zero-spin isotopes without the usage of standard substances like tetramethylsilane for 1H, 13C, or 29Si. Indeed, if we know or compute a spectrum for one non-zero-spin nuclei type so that it is scaled to known standard (i.e. we have absolute spectra), and we know the exact relation between NMR isotopes and use this relation on the correlated oscillators, all other spectra are already absolute spectra. This is a very important feature for inorganic or element-organic chemistry, since most non-zero-spin isotopes have few response lines in their spectra and cannot be matched without usage of chemical standards.

Hence, we demonstrated that correlated oscillators allow the removal of instability in the magnetic field and/or oscillators. This capability opens a new horizon for the use of small and affordable magnets, magnets with Halbach-like focusing of the magnetic field, and affordable oscillators.

General Method for Processing Signals that Represents a Product of at Least Two Signals Hence, we are suggesting the following method. A method of processing at least one input signal $u_m(t)$, $m=1, \ldots, M$, determined with its weight coefficients $0 \leq w_m(t) \leq 1$, that represents a product of at least two signals $q_n(t)$ in order to determine at least one unknown signal among the signals $q_n(t)$, $n=1, \ldots, N$, so that $p_n(t)$ refers to a phase component of $q_n(t)$ and $t \in [0, T]$, the method comprising: extracting phase information $s_m(t)$ from the input signals; defining model parameters $a_{nm}$, $n=1, \ldots, N$, $m=1, \ldots, M$, so that at least one model parameter is known and equal to one; defining the residual function $$f_m(t) = s_m(t) - \sum_{n=1}^{N} a_{nm} p_n(t);$$

mapping $f_m(t)$ into $[-\pi,\pi]$ so that if the value of $f_m(t)$ is situated outside of $[-\pi,\pi]$, then one or several $2\pi$ are added or subtracted from $f_m(t)$ such that the result is situated in $[-\pi,\pi]$; defining the phase residual function $g_m(t)$ as a product of the mapped $f_m(t)$ and the weight coefficients $w_m(t)$; minimizing deviation of $g_m(t)$ from zero in $t \in [0, T]$, $m=1, \ldots, M$, over unknown parameters $p_n(t)$ and unknown parameters $a_{nm}$ and saving the values of $p_n(t)$ that refers to the point where minimal deviation is achieved; and computing the unknown $q_n(t) = \exp(ip_n(t))$ using the saved $p_n(t)$.

The minimization of deviation of $g_m(t)$ from zero in $t \in [0,T]$, $m=1, \ldots, M$ can be performed in an Euclidean norm by minimizing $$\int_0^T \sum_{m=1}^{M} g_m^2(t) dt,$$

or in an infinity norm by minimizing $$\int_0^T \sum_{m=1}^{M} |g_m(t)| dt,$$

or by minimizing $$\int_0^T \sum_{m=1}^{M} w_m^2(t) \sin^2(g_m(t)) dt.$$

The minimization $$\int_0^T \sum_{m=1}^{M} w_m^2(t) \sin^2(g_m(t)) dt$$

can be performed as one initial step followed by a series of steps. The initial step consists of initializing unknown $p_n(t)$ and $a_{nm}$ as zero. Each odd step then computes the $f_m(t)$ that minimizes $$\int_0^T \sum_{m=1}^{M} w_m^2(t) \sin^2(f_m(t)) dt + \gamma \int_0^T \sum_{m=1}^{M} w_m^2 \left\| s_m(t) - f_m(t) - \sum_{n=1}^{N} a_{nm} p_n \right\|_2^2 dt,$$

and each even step fixes $f_m(t)$ from the previous step and minimizes $$\int_0^T \sum_{m=1}^{M} w_m^2 \left\| s_m(t) - f_m(t) - \sum_{n=1}^{N} a_{nm} p_n \right\|_2^2 dt$$

over unknown $p_n(t)$ and $a_{nm}$, where $\gamma > 1/2$.

The minimization $$\int_0^T \sum_{m=1}^{M} \omega_m^2(t) \sin^2(fm(t)) dt + \gamma \int_0^T \sum_{m=1}^{M} \omega_m^2 \left\| s_m(t) - f_m(t) - \sum_{n=1}^{N} a_{nm} p_n \right\|_2^2 dt$$

over $f_m(t)$ can be performed through the following steps: computing $$z_m(t) = s_m(t) - f_m(t) - \sum_{n=1}^{N} a_{nm} p_n,$$

and then computing $f_m(t)$ as a root of $\sin(2f_m(t)) + 4\gamma f_m(t) = 4\gamma z_m(t)$.

In the case where $\gamma \geq 2/3$, the root of $\sin(2f_m(t)) + 4\gamma f_m(t) = 4\gamma z_m(t)$ can be computed by the Newton method, comprising the steps: taking the initial approximation $f_m(t) = z_m(t)$, computing a new approximation of $f_m(t)$ as $$f_m(t) - \frac{\sin(2f_m(t)) + 4\gamma(f_m(t) - z_m(t))}{2\cos(2f_m(t)) + 4\gamma},$$

and repeating the previous step until a deviation of $\sin(2f_m(t)) + 4\gamma f_m(t) - 4\gamma z_m(t)$ from zero is within a predetermined accuracy.

In the general case $\gamma > 1/2$, the root of $\sin(2f_m(t)) + 4\gamma f_m(t) = 4\gamma z_m(t)$ is computed by the bisection method, starting with the upper and lower bounds of $f_m(t)$ for the bisection segment as $[z_m(t) - \pi, z_m(t) + \pi]$.

The Elmathron

Figure 11:
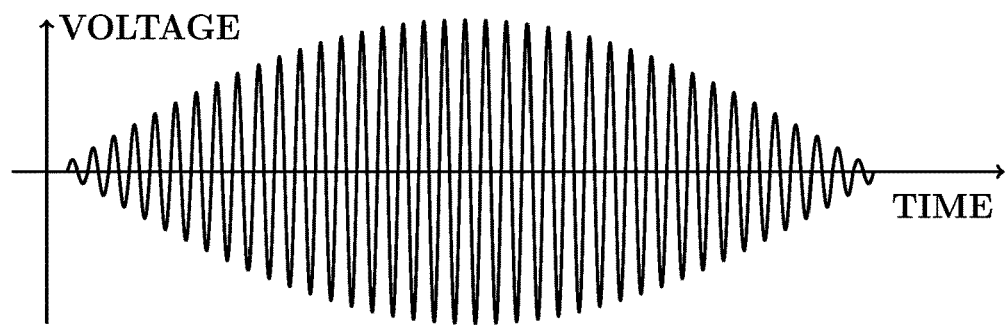
FIG. 11: A waveform with amplitude modulation produced by ELMATHRON. This is a representative schematic, as the actual total number of waves inside a pulse is usually larger than shown in the picture and depends on nuclei and pulse type.

The Electron Larmor Microwave Amplifier THReaded On Nuclei (ELMATHRON) is an apparatus to deliver electron Larmor frequency waves whose amplitude is modulated by a nuclear Larmor frequency pulse. An example of the waveform is found in FIG. 11, where a highly oscillated signal (ca. 40 GHz at 1.5 T) that refers to the Larmor frequency of electrons is amplitude modulated by the low oscillated signal or pulse referring to the Larmor frequency of nuclei (ca. 60 MHz for 1H at 1.5 T).

Figures 10A, 10B, 10C:
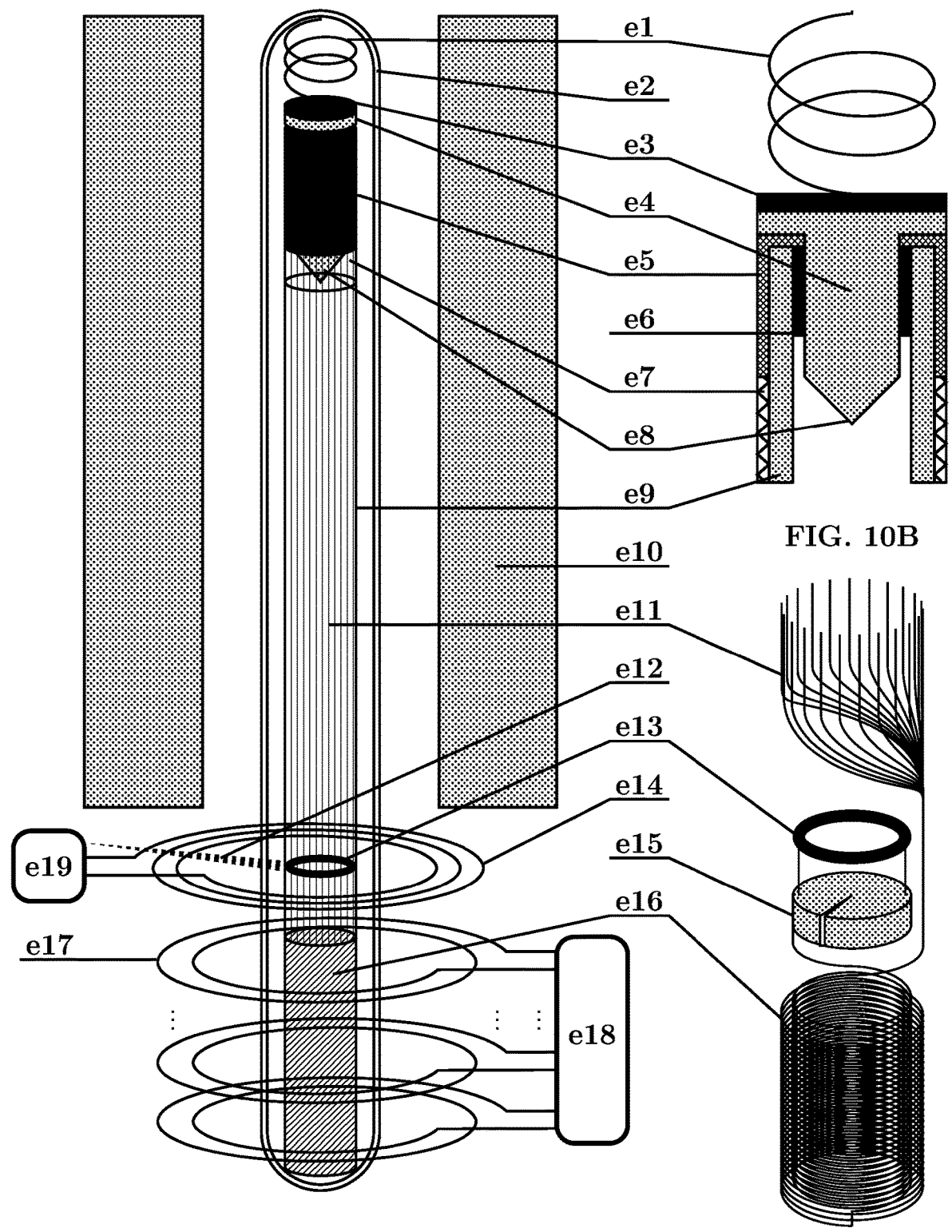
FIG. 10A refers to the main assembly.
FIG. 10B shows in detail the top portion.
FIG. 10C shows in detail the printed lines on tube e9 on the bottom of the ELMATHRON.

The ELMATHRON (FIG. 10) consists of a hermetically-sealed, deep vacuum-compatible glass or ceramic vessel e2. All energy transmissions into the ELMATHRON occur by inductive and/or electromagnetic methods.

A glass, ceramic, or any high voltage-resistant tube e9 is situated inside the vessel e2 and may have a printed metallic or conductive design (e5, e6, e7, e11, e16) on its inner and outer surfaces.

The bottom of the tube e9 contains the secondary winding e16 of a forward converter. The primary winding e17 of the forward converter is situated outside of the hermetically-sealed vessel e2 and is organized by many parallel windings. Each has a few turns that are operated at low voltage (5-100 V) so that the voltage/turn ratio is about 2-100 V. In contrast, the secondary winding e16 has a large number of turns. If the secondary winding contains printed coils in the inner and outer sides of the tube e9, the total number of turns may be around 10,000, and the total voltage in the second winding of the forward converter may easily reach 100 KV.

The ELMATHRON is designed to sustain a deep vacuum for a long period of time. For this reason, the following components are used:
- glass or ceramics parts e2, suitable for deep vacuum,
- printed traces of copper, silver, aluminum, or other vacuum-friendly metals and alloys in e5, e6, e7, e11, e16,
- tungsten and high-melting metals in e1, e13, and
- appropriate getters e3 and/or e15.

The printed coil e16 is connected on one side over the getter block e15 to the cathode e13 of the ELMATHRON, and on the second side over traces e11, diffraction grating e7, and shielding screen e5 to the anode e6. Smooth turns in each trace on the conductive components, such as traces between e11 and e16, will prevent unnecessary electromagnetic interference.

The anode e6 of the ELMATHRON is preferably printed/deposited on the inner side of the tube e9 with an additional metal e5 as a shield to prevent unnecessary electromagnetic interference. The electron beam flows from the cathode e13 to the anode e6. The permanent magnetic field, created by external magnets e10, causes electrons to move helically in tight circles around the magnetic field lines as they travel lengthwise through the tube. At the position in the tube at which the magnetic field reaches its maximum value, the electrons radiate electromagnetic waves in a transverse direction (perpendicular to the axis of the tube) at their Larmor (cyclotron) resonance frequency. The radiation forms standing waves in the tube, which acts as an open-ended resonant cavity, and is formed into a beam that radiates through the diffraction grating e7.

A reflector e8 may be constructed as a cone, a flat mirror, a focusing/collecting mirror, or any of many other possible shapes such that some part of the emitted waves may be reflected back to the cathode e13 to accelerate the cathode's electron emission.

The cathode is preferably constructed as the shorted turn e13. It is important that the cathode be made of high-melting metals and remains in a high-temperature state during operation. Preferably, the cathode is made in the form of a circle/ring that is as large as possible while also not touching the walls of e9.

The getter block e15 may be omitted, so that the cathode e13 is directly connected to the printed coil e16.

In the case of a getter block e15 being present, it may have arbitrary shape, with the following restrictions: the top face and its surface (that looks to the anode) should be as large as possible, and no shorted turns, which may result from inductive transformations from e14 and/or e17, are permitted.

Said getter e15 can be made as a metal foam block that completely fills this tube and has notches so that this foam does not build shorted turns; it can also be made as a flat spring or as any other form with maximal possible surface area and no shorted turns.

It is important to make the connection from the cathode e13 with thin conductive metal wire(s) so that heat from the cathode is not transferred to said getter e15; the getter should remain cold so that it can function in collecting unnecessary ions and improving the vacuum inside the ELMATHRON.

The embodiment including said getter e15 improves the lifespan of the device. In this case, the ELMATHRON works as a sputter ion pump maintaining ultra-high vacuum for a long period of time. Ions situated inside the ELMATHRON flow in the direction of the cathode and are captured by the cold getter e15.

The getter e15 can be made of titanium, a titanium-rich alloy, a Ti—Zr—V alloy, or any other conductive wire or foam of appropriate alloy.

Making the getter e15 massive or using massive foam (several millimeters in height) improves cooling of its upper face, resulting in improved ion absorption.

The external inductive heater e14, with its optical feedback e12 and control unit e19, sustains the high-temperature state of the cathode.

One can use an electromagnetic beam e12 (a laser, for example) to heat the cathode e13 in parallel with or alternatively to inductive heating; electromagnetic beam heating can also be used to bring the surface of the cathode into an excited state to improve the overall efficiency of the ELMATHRON's operation.

The first step of the working cycle of the forward converter creates high voltage on the secondary winding e16, so that the cathode e13 assumes a negative charge and the anode e6 assumes a positive charge, forcing the emission of electrons from the cathode to the anode.

The second step of the working cycle exchanges the polarity of charges between cathode and anode, thereby locking the electron beam to the backward direction.

When printed on the inner and outer side of the tube e9, the secondary winding e16, diffraction grating e7, connections e5, e11, e15, and the anode e6 may be organized as a thin metallic film that is chemically deposited or sprayed.

The spaces between traces are preferably burned/etched by the optical/laser heater, so that a 1-100 µm thin layer with 1-10 µm of trace deviation accuracy is afforded during production.

Having the thin layer on the printed coil e16 with a total length of 10 cm may provide a pulse-width of less than 10 n5 with 1000 V/ns and $10^5$ watts of peak power at the coil. Parameters even better than this may be achieved.

Due to its construction, the working cycle of the forward converter may be as brief as several nanoseconds and may be chosen to match the duration of the excitation NMR pulse sequence, during which each pulse is modulated with the electron Larmor frequency. Hence, the ELMATHRON works as a polarizer (on the electron Larmor frequency), as an NMR transmitter (on the nuclear Larmor frequency), and as a phased-array transmitter (taking the diffraction grating e7 into consideration and/or several ELMATHRON vessels working in parallel).

It is evident that instead of the forward converter scheme, it is possible to use full-bridge, half-bridge, and many other similar transformer schemes. However, the forward converter maximally reduces the total count of components and appears to be optimal for the outlined goal—providing a dual-band Larmor electron and nuclei frequency generator.

Magnets

Since the magnitude of the electric response from an NMR experiment grows quadratically with regard to the magnetic field strength used, it is important to use magnets with the highest possible field strength. As discussed previously, the magnets may be either:
- an external magnetic source as, for example, is disclosed in FIG. 18, or
- embedded permanent magnets as, for example, are disclosed in FIGS. 13-17, 20.

In the case of embedded permanent magnets being used, they may have either:
- anisotropic magnetization, where the entire magnet(s) are magnetized in one direction (FIGS. 21A, 22 and 23), or
- well-known Halbach structure or any other similar structure where the magnetic field in the predetermined zone may be larger (often by several times) than could be achieved with anisotropic magnetization.

Nowadays, Halbach structures are often used in NMR spectrometry; however, they always require joining many small magnetic parts.

In the case of one transmitter and receiver coil assembly (FIG. 12) being used, the optimal Halbach magnetization occurs as in FIG. 24.

In the case of an ELMATHRON with several coil receivers (FIGS. 14-18) being used, the optimal Halbach magnetization may be even more complicated, as shown in FIG. 25. Here, the direction of the magnetic field in the receiving coils is anti-parallel to the direction of the magnetic field in the ELMATHRON vessel.

In the case where such an array is constructed with several pieces of magnets, one needs to combine an enormous number of magnetized pieces; doing so may be commercially ineffective.

In the case of MR. NIB technology (FIG. 20) being used, the optimal Halbach magnetization may be even more complicated and looks as in FIG. 21B. The key advantage of this method is to generate an extremal (high or low) magnetic field strength on a point situated far from the magnets, and to not have any such extremal magnetic strength anywhere in the neighborhood of this point or in the area where the patient's body may be situated. This result is achieved simply by appropriate magnetization of the magnets. A representative contour plot of magnetic field strength sandwiched between these magnets is given in FIG. 21B.

In addition, the combination of a modulated ELMATHRON beam, magnetic field, and appropriate non-zero-spin isotope opens the new possibility of using an electromagnetic field of nuclear Larmor frequency on said non-zero-spin isotope instead of or in parallel with said modulated ELMATHRON's beam.

Hence, the key advantage compared to U.S. Pat. No. 8,148,988 consists of the direct magnetization of magnetic material during magnet pressing/sintering/casting/forming, either
1. to achieve a field strength outside the magnets that is higher than the maximal possible field strength of anisotropic magnets for the same material, or
2. to produce a local extremum of magnetic field strength (this case is mainly useful with MR. NIB technology).

Consider making each magnet of the ELEGANT NMR and MR. NIB technologies, i.e. every g7, g8, g9, g10, g11, and g12, independently as cylinders or, in general, as any arbitrary shape. It is easy to predict by numerical computation an optimal magnetization for each point of these magnets that yields the maximal possible magnetic field strength in a measured area outside of the magnet itself. In the embodiments comprising ELMATHRON(s), said maximal possible magnetic field strength should be in the measured area and inside the ELMATHRON's vessel. There are two variants with parallel and anti-parallel magnetic fields in said measured area and ELMATHRON vessel. Both variants work well, and which variant should be used depends on the device and magnet sizes.

Hence, distribution of the anisotropy of magnetic particles inside the magnets should be as in FIGS. 21B, 24-27, and this magnetization should provide the maximal possible magnetic field in the desired area.

The optimal magnetization of magnets g11 and g12 is highly dependent on device size, the set of non-zero-spin isotopes used for MR. NIB therapy, and the general requirement to generate an extremum of magnetic field strength, so many different magnetizations may be suitable.

Nowadays, there are two main technologies for permanent magnet construction:
- forming magnets from powder, and
- casting magnets.

Both technologies require a permanent magnetic field to be applied during forming or casting, and after this procedure, one needs to magnetize the magnet.

Formation of a magnet may be realized through many methods: by pressure, by additional lubricant and/or glue, by sintering pressed powder, etc. In all cases, it usually involves additional pressure being applied to the powder, and may require postprocessing (heating/sintering, etc) after this procedure.

Casting a magnet requires liquid magnetic material at high temperature, and that the material is crystallized in an external magnetic field during cooling.

In this patent application, we proposed to apply a non-uniform magnetic field of special shape during casting or forming.

Consider first the forming of magnets from anisotropic magnetic powder.

To make such a magnet, the following method and corresponding apparatus (FIG. 29) is suggested. It is comprised of
- a molding matrix g19,
- a molding tool g18,
- a set of one or several magnetic field creating and adjusting materials g21:
  - permanent magnets, and/or
  - ferromagnetic materials, and/or
  - permanent electromagnets, and/or
  - superconductor electromagnets, and/or
  - any other non-magnetic materials, and/or
  - permanent magnet(s) previously manufactured with the same technology, and
- a magnetic powder g20 with particles that can be anisotropically magnetized, whereby
said magnetic powder is situated in said molding matrix, said molding tool acts on said magnetic powder, reducing its volume and forming a molded magnet, and
said magnetic field creating and adjusting materials are situated in a predetermined spatial configuration.

To predict said predetermined spatial configuration, one needs to use a well-known equation that computes the magnetic field in a point $Y \in \mathbb{R}^3$ occurring from a magnetic dipole situated at a point $X \in \mathbb{R}^3$ with its magnetization direction $\overline{M} \in \mathbb{R}^3$:

$$B(\overline{M}, X, Y) = \frac{3(Y-X)(Y-X)^T\overline{M} - \overline{M}(Y-X)^T(Y-X)}{\|Y-X\|_2^5}, \quad (f21)$$

and performs the following algorithm.

Algorithm Nr. 3.
1. perform finite element discretization of the complete area where the molded magnet is being pressed,
2. for the spatial distribution of every permanent magnet and/or permanent electromagnet,
 3. find the numerically appropriate magnetization direction for every said finite element, checking that discretization in that finite element is fine enough to achieve a smooth and accurate solution,
 4. take each finite element and scale the magnetic field in such a way that it is maximally magnetized,
 5. compute with the help of (f21) a magnetic field from the all finite elements in
  6. the measured area; and
  7. if needed, the ELMATHRON's vessel;
  8. the area of the patient's body where MR. NIB therapy is to be used,
9. perform steps 3-8 maximizing/optimizing the magnetic field in the desired area; if needed, constrain divergence of the field in that area; and find the best possible configuration of permanent magnets and/or permanent electromagnets.

Said algorithm delivers the optimal configuration of permanent magnets and/or permanent electromagnets and, if a sintering device FIG. 29 is constructed according to these rules, the magnetic field of the pressed magnet will be as large as possible with respect to magnet size and desired area and constraints in magnetic field divergence.

Additional fluids, and/or ultrasound, and/or shaking of the area g20 may be helpful, because adding fluid will make Bingham fluids from this powder and allow the rotation of magnetic particles with less external magnetic flux, while ultrasounding and/or shaking improve the transformation of this mixture into Bingham fluid.

Hence, magnet production can be performed by the following steps:

1. Based on physical shapes and numerical simulations, choose the appropriate geometry of magnet g20 and area g21 with
 permanent magnets, and/or
 ferromagnetic materials, and/or
 permanent electromagnets, and/or
 superconductor electromagnets, and/or
 any other non-magnetic materials, and/or
 permanent magnet(s) previously manufactured with the same technology.
2. Insert magnetic powder with/without fluids into the area g20,
3. Slowly apply pressure from g18 to perform pressing and, in parallel to this procedure, apply shaking and/or ultrasonic vibration. At the first stage, a constant pressure should be applied based on the shape and size of the magnetic powder. During this stage, magnetic particles may rotate to situate themselves in the direction of the external magnetic field organized by g21. When the volume of the magnet g20 has become less than the possible volume where each average particle touches its neighbors, the pressure should be slowly increased until cold sintering occurs.
4. The constructed magnetic part is then sintered according to the appropriate process for its material. During sintering, the magnet usually loses its magnetic power; however, it becomes stable with physical stress since all magnetic particles become fixed.
5. The constructed part is next inserted into a device FIG. 30 that is similar to that used in stages 1-3; however, instead of permanent magnets/electromagnets, a pulse magnet(s) g22 that may achieve a pulse magnetic field of several Tesla with similar magnetic field configuration is situated in the area g25, and a short electromagnetic pulse is applied so that the magnet becomes magnetized.

Hence, this method allows making a magnet such that it will produce higher magnetic strength outside of its shape than if it were a large anisotropic magnet constructed from the same magnetic material. As an example, we were able to achieve a magnetic field of 2 T for magnets of 24 mm diameter and FIG. 25 shape with material that can deliver at maximum 1 T in an anisotropic version.

Magnet casting may be performed with similar technology; however, instead of applying pressure to the magnetic powder, we should apply heating.

The key idea in this case is to use the same electromagnetic coils and/or materials to generate the external magnetic field and to produce heat. Heating may be organized by:
 resistive heating of one or several coils, and/or
 inductive heating of casted material, and/or
 inductive heating of conductive crucible with casted material, and/or
 resistive heating of casted material.

Hence, magnet production can be realized through the following steps:

1. Based on physical shapes and numerical simulations, choose the appropriate geometry of magnet g20 and area g21 with
 permanent magnets, and/or
 ferromagnetic materials, and/or
 permanent electromagnets, and/or
 superconductor electromagnets, and/or
 any other non-magnetic materials, and/or
 permanent magnet(s) previously manufactured with the same technology.
2. Insert magnetic material for casting into the area g30,
3. Switch on heating so that said magnetic material melts.
4. After the magnetic material is melted, switch off heating and switch on the electromagnets on a level such that they produce a magnetic field.
5. By controlling the cooling of electromagnets and resistive heaters, with/without the help of additional temperature sensors, perform slow cooling of said magnetic material while keeping the magnetic field at a level that is sufficient to cast an anisotropically-oriented magnetic structure.
6. When the crystalline structure of casted magnetic material is frozen and the magnetic material is below its Kuri point, one should apply a pulse magnetic field of several Tesla with similar magnetic field configuration as was used during casting, so that the magnet becomes magnetized.

Hence, this method also allows making a magnet such that it will produce a higher magnetic strength outside of its shape than if it was a large anisotropic magnet constructed with the same magnetic material. As an example, we were able to achieve 3 T for magnets of 24 mm diameter and FIG. 24 shape with material that can deliver at maximum 1.4 T in an anisotropic version.

In-situ portable spectrometers, based on ELEGANT NMR with and without ELMATHRON, are preferably constructed with small magnets. These magnets may lose their magnetic strength over time because they can be demagnetized when placed in inappropriate conditions, e.g. near electromagnets or large iron parts. To extend their working lives the device of FIG. 30 or a variant of FIG. 31 without heating may be used to recover depleted magnets.

Magnetic Material

Nowadays, there are many magnetic materials available for magnet construction by either sintered or casted processes;

sintered magnets may contain Nd—Fe—B, Sm—Co, Al—Ni—Co—Fe, Mn—Bi, Mn—Al, and many other alloys, while casted magnets contain mainly Al—Ni—Co—Fe alloys.

If casted, the magnetic material should be placed at high temperature and slowly cooled. Doing so requires that the casted material be held in forms resistant to high temperature.

If sintered, the magnetic material should be placed on a close form and additional pressure applied. This requires that materials resistant to high pressure to be used to hold the sintered material.

The construction process requires an external magnetic field. To create a permanent magnetic field with anisotropy over a large region, one can use Helmholtz coils. In this case, the area with high magnetic field strength and anisotropy is situated physically far from the area where magnets are casted or sintered. Hence, there is no difficulty in placing the forms for casting or sintering far away from the electromagnetic coils that generate the permanent magnetic field.

The typical permanent magnetic field is sourced from copper coils, which are not very resistant to a high-pressure environment. The typical pressure for synthesizing sintered magnets is above 3000 bar; withstanding this requires the enclosure for this process to be constructed precisely. For some magnetic materials that sinter at very high pressure (above 5000 bar), making copper coils that can withstand that pressure may be almost impossible.

Similar difficulties complicate the casting of Halbach-like structures—here, one should place a permanent magnetic field source very close to the casted material while it is at high temperature. The typical copper coils do not withstand temperatures above 1000° C., and at elevated temperatures additionally have their electric conductivity reduced six-fold. It is thus necessary to provide a good thermal barrier between the coils and the casted material, or else to find an alternative field source material for magnet production.

For the magnet being constructed, alloys of Al—Ni—Co—Fe are very promising materials in both casted and sintered processes because they are capable of achieving 1.4 T of residual magnetization as anisotropic magnets. These alloys consist of two independent magnetic crystals: $CoFe_2$ crystals with high coercivity and magnetic field strength, and Al—Ni crystals which have poor magnetic properties but allow the building of the so-called matrix, where the $CoFe_2$ crystals freeze during casting.

However, these alloys have very high temperatures of casting (from 700° C. to 1100° C.), which restricts their use in the casting of Halbach-like structures. Furthermore, sintering these alloys requires enormous pressure (above 4000 bar), which also restricts their usage in sintered Halbach structures.

We suggest the substitution of AlNi crystals in Al—Ni—Co—Fe alloys with other magnetic materials that have lower melting temperature and/or less resistance to high pressure. A good candidate would be the well-studied MnBi crystals that, when more Bi is incorporated, can be melted at temperatures as low as 400° C. Any other low-temperature and low-viscosity magnetic material can be also used, for example MnAl alloys.

As a good example of magnetic material for Halbach casting, we suggest a mixture of CoFe (or SmCo) crystals, MnBi alloy, and Bi (and/or In) with molar ratio of 1:1:1/4 or similar. The CoFe crystals are the main phase of Al—Ni—Co—Fe magnets and have a body-centered cubic (BCC) structure. One can increase the molar ratio of CoFe up to three to obtain a slightly stronger magnet at the cost of requiring higher temperature for casting. If the molar ratio of CoFe is below one, the magnet becomes weaker.

In addition to adjusting the relative molar ratio of CoFe, magnet properties are affected by the alloy proportions; all $Co_xFe_{1-x}$, where $x \in [0.2, 0.8]$ form a BCC structure, were tested and can be used for the production of magnetic material.

To make said magnetic material, we take Co, Fe, Mn, Bi, and In at a molar ratio of 1:2:1:1.1:0.27 and in the form of ultrafine powders (1-10 um). These are placed in a vacuum chamber ($10^{-4}$ Torr) and heated at 200° C. for about one day. After that, we increased the vacuum to $10^{-6}$ Torr for several hours, sealed the chamber, and heated it to ca. 1500° C. for another hour. It is important to seal the chamber because at this temperature, bismuth evaporates with high pressure (ca. 1 bar) and Mn and other metals can immediately react with oxygen from the air. We successfully tested two different methods for heating, inductive and heat transfer. We expect that any other heating methods such as resistive or discharge should also work well. After said heating, we slowly (0.5° C. per minute) cooled the material to room temperature.

As an alternative to vacuum heating or melting, it is possible to use argon or any other inert gas melting, or to heat under low pressure hydrogen or inert gas flow, only taking into account that all oxygen, nitrogen, and other active gases should be removed from initial powder components.

The following physical properties were observed: the mixture of powders melts at circa 1500° C. with a density of about 2.5-3 g/cm³, in contrast to a density at room temperature of about 7.5 g/cm³ (and ca. 5.5 g/cm³ before sintering/casting). If the melting procedure described above is performed, the obtained magnetic material solidifies at ca. 400° C. and liquifies at circa 900-1000° C. At temperatures of 200° C. and above, this magnetic material irreversibly reacts with oxygen from the air, completely losing its magnetic property. The magnetic material can be milled to fine powder, and can be pressed and sintered at pressures starting from ca. 100 bar, with good results achieved below 1000 bars. In the case of casting in a magnetic field with this material, it is possible to start casting at 450-500° C. with slow cooling (0.2° C. per minute) to 300° C.

The key difference of this prepared magnetic material (FIG. 28) from commonly-used materials is that it builds BCC $Co_xFe_{1-x}$ crystals g32 that are situated on another material (low temperature melting alloys g34 including one or several elements of In, Bi, Sn, Ga, Tl, Cd, Zn, Pb, Te, and/or ferromagnetic like Mn—Bi g33). This combination gives new mechanical, thermal, and magnetic properties, i.e. the achieved material can be sintered at low pressure (1000 bar), can be casted at low temperature (500° C. and below), and is perfectly suitable for a Halbach-like sintering/casting process as proposed in our patent application.

Hence, said magnetic material used in said magnet sintering/casting process makes possible the affordable production of small magnets that focus a magnetic field to very high levels, allowing a field strength that is several times larger than the currently available 1.4 T magnets.

Method of DNP-NMR Measurements

Hence, the following method of DNP-NMR measurement is suggested:
- one or several microwave beams with a carrier frequency that refers to the electron Larmor frequency are directed at the measurement area (FIGS. 14-18);
- every microwave beam is amplitude modulated with frequency referring to the NMR excitation frequency and/or pulse sequence (FIG. 11), so that each microwave beam acts as both the polarizer (by electron Larmor frequency) and the transmitter (by nuclear Larmor frequency);
- one or several receiving coils and/or optical detectors (a6, a25) are situated over, and/or around, and/or near the materials being measured, so that said beams with their modulations act to measure substances crossing the permanent magnetic field;
- the same permanent magnetic field generator a26 may be used for the measuring area and for electron acceleration in the ELMATHRON vessels a4.

This method allows the advantage of constructing two applications, an in-situ NMR detector (FIGS. 13-15) and a chromatography NMR detector (FIGS. 16-18), as well as offering a new processing method for DNP-NMR measurement that benefits from many receiving NMR coils and one or several ELMATHRONs, with or without diffraction grating in the ELMATHRONs to enable different excitations of measured substances around the receiving NMR coils.

An embodiment in FIG. 18 demonstrates the ability to upgrade the currently available permanent magnetic source with the DNP-NMR system, so that the same permanent magnetic field can be used for both the measuring area and for electron acceleration in ELMATHRON vessels.

In-Situ NMR Detector

Two embodiments are proposed (FIGS. 13-15): the first one (FIG. 13) comprised of coils to transmit and receive the NMR signal, and the second one (FIG. 14) using the ELMATHRON to transmit and polarize measured substances. Both embodiments are comprised of two parts, the first part a16 containing magnets and the second part a15 electronics, and advance from the situation where several versions of the first part are constructed with different materials that are compatible with different temperature ranges, pressure ranges, and chemical exposures.

Said first part a16 is comprised of
- permanent magnets a1;
- one or several receiving coils (a20 or a25) situated between magnets a1, with these coils connected to plug a13, which is incorporated in case a16; and
- one or several transmitters a20 or a4.

The transmitter may be constructed with one or several ELMATHRON vessel(s) a4 having microwave emission point(s) situated between the magnets a1 (FIG. 14A), and/or one or several transmitting coil(s) a20 situated between magnets a1 (FIG. 13A).

Said first and second parts of the in-situ NMR detector are hermetically isolated from each other. In addition, said second part may be environmentally conditioned with regards to temperature, pressure, and physical isolation from outside chemical substances. Hence, the second part is carefully protected and may be comprised of sensitive electronic parts a14.

Figure 12:
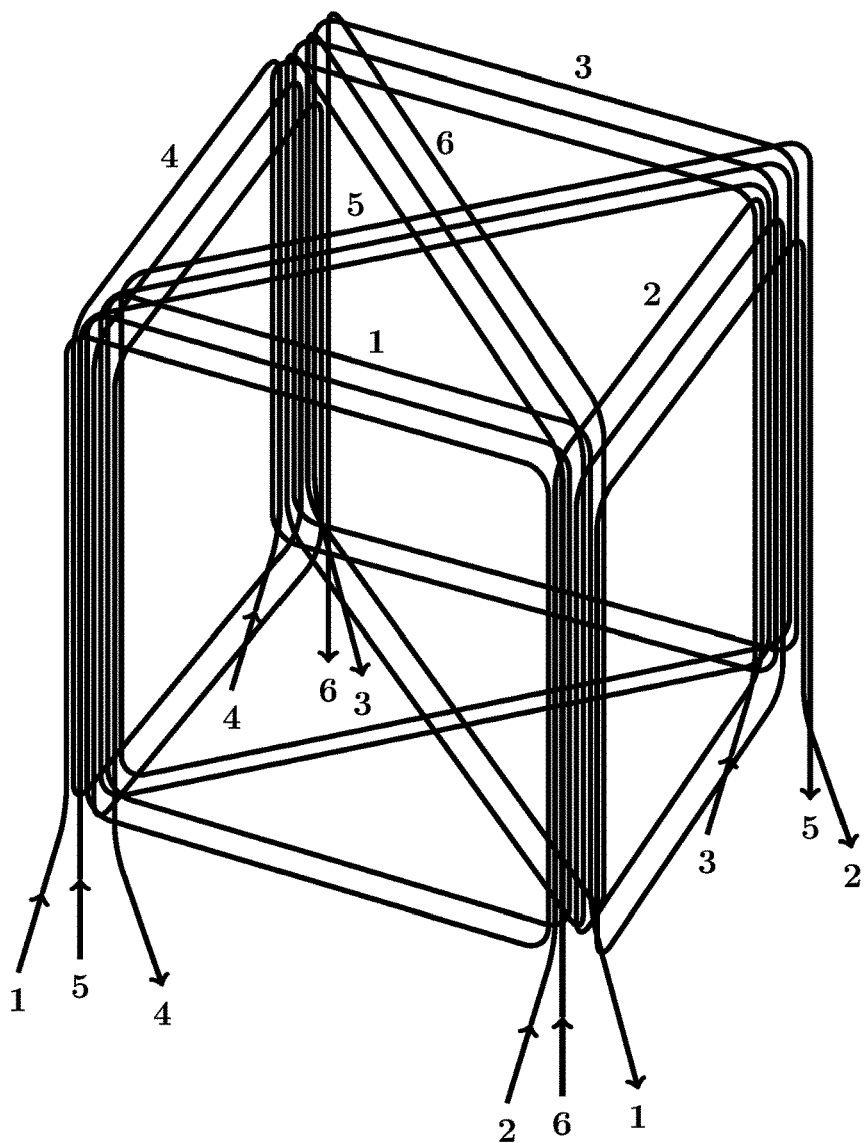
FIG. 12: Six coils situated on the edges of a parallelepiped (three-dimensional figure formed by six parallelograms). The total number of turns for each coil may be two or more. The numbers of turns on coils within each subset {1, 2, 3, 4} and {5, 6} are equal, i.e. coils 1-4 must be the same and coils 5-6 must also be the same, but coils 1-4 can differ from coils 5-6. The optimal number of turns in each subset depends on the dimensions of the device, the magnetic field's strength, and the electronics used. Depending on the embodiment, each coil subset may be comprised of transmitting and/or receiving coils.

A simplified version of the in-situ NMR detector may be equipped with two receiver and four transmitting coils a20 according to the drawing in FIG. 12, with said coils situated in the first part a16 so that the receiving coils correspond to numbers {5, 6} and transmitting coils correspond to numbers {1, 2, 3, 4}.

In an embodiment with the ELMATHRON (FIG. 14), an energy and signal transmission from its second part a15 to the ELMATHRON vessel a4 situated in the first part a16 occurs by means of inductive coupling.

The advantage of coupling small magnets to the electronics relies on the fact that the conductive traces a19 between electronic chips on PCB boards and coils are several times shorter than the wave length of the largest electromagnetic wave traveling on them; this permits disregarding the wave impedance of electromagnetic signals traveling on said traces a19.

In addition, using a conductive magnetic material for the magnets in a1 and/or a24 reduces the electromagnetic interference of signals traveling on said traces a19 because said magnets act as electromagnetic shields.

For high viscosity fluids or, in the case of needing to clean a measuring area fouled by solids or precipitates, we suggest using one magnet and performing measurements on the surface of that magnet, albeit lower magnetic field strength achieved.

The key difference of our approach from, for example, the approach of Bluemich (1998) (i.e. one-side NMR) resides in the following advantages:
- the usage of dual band transmitters (ELMATHRON) that improve the signal to noise ratio by about two orders;
- the usage of magnets with non-uniform magnetization, which improves the smoothness and strength of the magnetic field and also leads to the improvement of signal to noise by a factor of ten; and
- the main electronics are equipped with constant temperature control by fluid thermostatting a11, which allows the use of this device in heavy industrial conditions.

Several non-uniform magnetizations for systems with and without ELMATHRON are referenced in FIGS. 24-27, so that the magnetic field direction can be either parallel (FIGS. 24, 25, and 27) or perpendicular (FIG. 26) to the main axis of the device.

Since the magnet is situated to the side of the device, one can perform final magnetization after the magnet is produced, allowing one to recharge depleted magnets.

The shape of the magnet surface need not necessarily be a plane, and may be optimized for considerations such as easiness of cleaning of the device, or improving the magnetic field and its smoothness.

An additional advantage of this in-situ NMR detector is that that it can be used for the measurement of many physical properties of liquids.

Temperature can be determined based on the temperature dependence of a magnet's field strength.

The measurement of viscosity and two-dimensional flow speed (all dimensions perpendicular to the main axis of the magnets a1) is performed as follows. Consider two tubes with different inner diameters both situated in a permanent magnetic field. Now consider that pulse sequences are applied to this material at several places:
- the area around the measured area, so that the fluid passes predetermined excitation points before and after the measured area;

in proximity to the tube's centers and in proximity to their walls; and within the two tubes with different inner diameters.

Signal responses from all the above-mentioned places are stored in a multidimensional array and tabulated for different flow speeds and viscosities. The resulting table is sufficient for determining the flow speed and viscosity of a measured fluid. Since the sensor may be equipped with four holes, as demonstrated on the FIG. 13D, then if at least two sensors with different linear dimensions are used, one can obtain the viscosity and two-dimensional flow speed of the measured fluid.

An in-situ NMR detector equipped with ELMATHRON and with several coils also benefits from the fact that different sizes of coils can be used, so that the measurement of viscosity and two-dimensional flow can be performed readily.

Pressure can be measured if an additional elastomer cylinder is situated near coils a20, and this elastomer is impregnated with predetermined non-zero-spin isotopes. If pressure increases, then the linear size of this cylinder decreases, and this change in size can be measured by the exciting/receiving coils of a20.

The measurement of density can be performed by taking the molar mass of each nonzero-spin isotope based on their responses and dividing by the isotope's relative natural occurrence.

Finally, some additional parameters like level sensor measurements can also be determined as derivatives of the measurements mentioned above.

Chromatography and Flow-Through NMR Detector

The main advantage of this embodiment resides in the possibility of using DNP in compact laboratory equipment, so several different embodiments of said chromatography and flow-through NMR detectors are shown in FIGS. 16-18. All of these embodiments are comprised of several receiver coils a6 that are turned over capillary a2 or organized according to the drawing in FIG. 12, and/or optical NMR detectors a6, and also contain one or several ELMATHRON vessels a4 that send their beams along capillary a2.

Said capillary and ELMATHRON vessels are both situated in either the permanent magnetic field, which is organized by permanent magnets a1, or an external permanent magnetic field a26 that may be constructed with permanent magnets or superconductor magnets.

Having many receiver coils working in parallel plus wave interference from one or several ELMATHRONs equipped with diffraction grating leads to the unique possibility of performing NMR measurements in flow along the entire length of the capillary.

To improve sensitivity, the capillary a2 and coils a6 can be constructed of materials with zero-spin isotopes. However, it is often not fiscally reasonable to do so. Alternatively, the capillary may be divided into two or more regions, each comprised of different isotope types in its coils and capillary. By making simultaneous measurements in all regions and applying methods described above, one can use information from each region to distinguish isotope spectra that are absent in that region.

For a useful example of this capability, consider two regions: the first has a quartz glass capillary with copper coils, and the second has a polytetrafluoroethylene (PTFE) capillary with silver coils. Hence, the part with the quartz glass capillary is sensitive to all isotopes except 29Si, 63Cu, and 65Cu, while the part with the PTFE capillary is sensitive to all isotopes except 19F, 13C, 107Ag, and 109Ag. With the help of the algorithm described in Appendix 1, one can get pure spectra of all non-zero-spin isotopes and remove any influence from magnetic field fluctuation. At the same time, said isotopes act as markers reducing the influence of any instability in the magnetic field and oscillator(s).

Any other alternatives with two or more regions comprised of different non-zero-spin isotopes are also suitable.

The advantage of coupling sending/receiving coils a6 to the electronics a3 relies on the fact that the conductive traces between electronic chips on PCB boards a3 and coils a6 are several times shorter than the wavelength of the largest electromagnetic wave traveling on them; this permits disregarding the wave impedance of electromagnetic signals traveling on said traces.

In addition, using a conductive magnetic material for the magnets in a1 reduces the electromagnetic interference of signals traveling on said traces because said magnets act as electromagnetic shields.

To improve the analysis of mixtures of different chemical components, the tube a2 may be filled with absorption components and function as a classic chromatography column.

Here, either the complete tube is filled with the same absorption component, or particles of varying size may be distributed along the tube/column/capillary a2. In this case, pumping an unknown mixture over this tube/column/capillary produces NMR responses that are different in time and that also differ along the length of tube/column/capillary a2. Thus, different components in the investigated mixture build different mixture sets in context of position, time, and NMR spectrum response. According to Kruskal's theorem (1977), if a large enough measurement of the mixture can be performed in three or more dimensions (i.e. the time domain, length along the tube/column/capillary, and at least one NMR spectrum dimension), it is possible to collect pure spectra as well as the relative concentrations at all points of measurement.

The stationary phase in the so-called chromatography column (organized in the capillary a2) may intentionally have components with zero or almost zero response in NMR, i.e. zero-spin isotopes, or isotopes with non-zero-spin but with different atoms than are being investigated in the test mixture.

Alternatively, or in parallel, the stationary phase may be built with some non-zero-spin isotopes that are not available or rarely available in the test mixture. One can use for example, rare-earth elements, like 141Pr, 151Eu, 153Eu, or 165Ho, that deliver very sharp but short decay signals, or elements such as 107Ag or 109Ag that deliver weak, sharp, but long decay signals and usually have no presence in organic chemistry.

Alternatively, or in parallel, the stationary phase may be built with diamond crystals doped with 11B, 14N, 15N or any other non-zero-spin isotopes, or with rare earth fluoride crystals, so that it acts as an optical NMR transmitter and/or receiver.

In this case, these isotopes are excited d1, d5 and then transfer (d5 to d6) their spin magnetization to neighbor molecules d6. The neighbor molecules act exactly as do the molecules with high retention in a test mixture, leading to a higher response from these molecules. In the event the chromatographical separation of the mixture is not complete, however, said magnetization transfer occurs with some difference in magnitude, the NMR response of molecules close to the stationary phase is higher, and a larger difference in magnitude of NMR response for these components can be easily measured. This adds an additional dimension to the NMR experiment, improving resolution (according to said Kruskal theorem) and/or the signal to noise ratio, and allows the discrimination of chemical components that were not separated completely.

The use of electrophoresis along the eluent stream together with the use of DNP further increases the sensitivity of the method the charged particles of the mobile and stationary phases and the mixture of investigated substances are polarized during electrophoresis, which increases the intensity of electron polarization by the method of two-band excitation at the electron and nuclear larmor frequencies.

State of the art chromatography columns retain a test mixture for a long period, and the chromatography detector that is situated after the column then detects pure substances over short periods of time. Since an NMR experiment is not quick to complete, using NMR in conjunction with a chromatography column requires either stopping the flow or transferring eluted substances into some vessel for further detection. However, for most of the period in which a chromatography column is being run, the associated chromatography detector detects a known substance—the mobile phase.

Hence, we suggest combining the NMR detector with the chromatography column (or a system very similar to it with necessary modifications for use in NMR), rather than appending the detector to the end. The key advantage of this approach is that NMR detection starts upon the test mixture being injected into the column and continues while it travels, providing immediate feedback on separation quality. This embodiment drastically cuts detection time and allows the user to act if the mixture is not adequately separating, for example by changing eluent (mobile phase), pressure, or other factors.

In addition, part or all of the column can be filled with many short regions of different markers, or so-called stationary phases (FIG. 32). Each marker contains one or several active parts (we abbreviate them in FIG. 32 as A, B, C, D, E), that possess good affinity with different organic groups presented in the investigated mixture (A, B, C, D, E). This leads to different substances in the investigated mixture interacting with different sides according to the corresponding marker molecules and intermolecular interactions with them (A-A, B-B, etc.). For each region with a marker, we perform a different multidimensional NMR experiment, so that the magnetization transfer from each particular organic or element group in the marker only progresses to particular components or its parts in the unknown mixture. This multidimensional NMR experiment should be performed for each marker, and the resulting NMR spectra compared while substituting pure spectra of markers and pure spectra of investigated substances. The differences will give exact information regarding the concentration of each particular substance in the neighborhood of each particular marker. Using the mathematical theory of multidimensional decomposition will lead to rigorous proof of this phenomenon.

This approach is suitable for chiral chromatography as well as the detection and investigation of proteins and large organic molecules. It is well known that molecules in the investigated mixture may orient differently, but these differences are usually not sufficient for separation. The intermolecular interactions between markers and molecules change the positions of peaks in nuclear Overhauser effect (nOe) NMR experiments or any similar multidimensional NMR experiment depending on molecule orientation, because of transfer of nuclear spin polarization. Hence, this leads to the detection of a particular component in a mixture without physical separation from other components.

This approach is particularly important because separation is no longer required for the detection of components in a mixture, only changes of orientation in mixture components compared to the markers. This leads to drastic simplification of experiment design, with choice of marker types becoming the key consideration. It is well known that the difference of Gibbs energy of two substances interacting with the stationary phase ($\Delta U_1$ and $\Delta U_2$) refers to the separation coefficient $\alpha_{1-2}$ of these substances by the formula $$\alpha_{1-2} = e^{\frac{\Delta U_1 - \Delta U_2}{RT}}.$$

If the Gibbs energy of interaction of one component $\Delta U$ with the stationary phase is around 10 kJ/mol or greater, that component interacts so strongly with the stationary phase that it may chemically bind to molecules of the stationary phase, leading to degradation of the separation column. Conversely, if a difference in Gibbs energy ($\Delta(\Delta U)$) between two components is below 1 kJ/mol, separation columns with large numbers of theoretical plates are needed to separate them. This usually requires larger separation columns, higher pressure (20000 psi and above), and a very sophisticated experimental setup.

Our method allows scenarios where the Gibbs energy of investigated substances interacting with markers ($\Delta U$) and the difference in said Gibbs energies for different substances ($\Delta(\Delta U)$) may be as low as several J/mol, thus a wide variety of markers can be used and overall device construction is drastically simplified.

The inventors performed a test experiment aiming to detect all four stereoisomers of 6-methyl-2-pipecolic acid using two 4-hydroxyproline markers impregnated on silica gel containing $Cu^{2+}$, where the first marker was the natural L-isomer and the second was a racemic mixture of all 4-hydroxyproline isomers. The Gibbs energies of different stereoisomers of 6-methyl-2-pipecolic acid with 4-hydroxyproline ($\Delta U$) in association with $Cu^{2+}$ are about 1-2 kJ/mol, and the differences between each possible pair of stereoisomers ($\Delta(\Delta U)$) are a little bit lower than 1 kJ/mol, which would conventionally require a good separation column with hundreds of effective theoretical separation plates. We intentionally used a system with only a few effective theoretical separation plates, so that detection of all four stereoisomers of 6-methyl-2-pipecolic acid by conventional separation is impossible. Our method detected all four stereoisomers with about 1% error in quantifications by performing 63Cu-65Cu-14N-1H and 15N-13C-1H multidimensional NMR measurements in a 1.5 T field, and needed only 20 minutes of measurements.

Usage of markers composed of porous substances/materials with high relative surface area works the same as in chromatography separation, leading to improvement of the signal/noise ratio that in general improves the efficiency of this method.

In addition, to save on the component count, we can excite magnetic resonance (MR) spectra at an arbitrary position with markers (i.e. if we focus on it with several transmitter coils, or with one or more ELMATHRONs or other dual-band transmitters) and detect the response from several neighbor MR detectors as the linear combination of responses as described on (f10). The position of excitation can be adjusted during the experiment and optimized according to the most suitable markers for the detected substances. So, after making preliminary measurements, we can detect most chemical groups in the measured substances, and then move the excitation point to the most suitable corresponding markers for those chemical groups. Hereinafter we will use the magnetic resonance (MR) term to abbreviate both the nuclear magnetic and the electron paramagnetic resonances/electron spin resonances.

In the event only a very small volume of the measured mixture is available, we can inject this mixture into an area with one marker, and by means of additional flow of the stationary phase move the investigated substance to the appropriate markers. In addition, an area with a plurality of markers may be moved so that the measurement area and the investigated substance are always situated in the proximity of MR detectors (FIG. 33).

We have to place the detecting mixture in contact with one or several marker molecules, where the marker is a substance causing the molecules of at least one of the investigated substances to adopt a predetermined orientation by means of intermolecular interactions. The marker can interact with substances by means of Van der Waals interactions or reversible chemical transformations. In practical terms, markers and substances collide in all possible orientation combinations, some of which have greater thermodynamic stability; these so-called more stable combinations statistically persist for longer periods of time than do others. It is possible that there are many thermodynamically stable orientations or a continuum of thermodynamically stable orientations. The important point for us is that the marker and investigated substance remain in specific relative orientations for greater amounts of time than they spend in other orientations, so that we will detect the MR spectra of these orientations.

There are numerous possible configurations of this setup. We can use one electron and nuclei MR transmitter or several MR transmitters; coil-based or dual band-based systems, like ELMATHRON; one or more MR receivers; and the MR receivers may be coil-based, optical, or antenna type. Both transmitters and receivers may be situated around, inside, deeply inside, or immersed in the measurement area. The measurements may be performed simultaneously by many MR systems at once or in succession.

In the case having a mixture with many substances and all of them adopt different orientations relative to one or several different marker molecules, we are able to collect many sums of the spectra of such marker-substance complexes. Each sum of spectra has particular scaling coefficients that relate to the marker type, its concentration, and other properties. Let us define the spectra variations as a three or more dimensional structure, $a_{n_1}, \ldots, n_K \in \mathbb{R} N_1 \times N_K$, in which the first dimension $n_1 = 1, \ldots, N_1$ corresponds to the MR spectrum (in the frequency, or in the time domains) and the other dimensions correspond to variations in the properties of the marker and substance.

In this case, we will use a general method of data approximation called a tensor decomposition $$a_{n_1, \ldots, n_K} \simeq \sum_{r=1}^{R} b_{r,n_1}^{(1)} \times \ldots \times b_{r,n_K}^{(K)},$$

so that a one-dimensional member of the decomposition of the first dimension $b_{r,n_1}^{(1)}$ corresponds to a set of spectra representing R substances and their intermolecular complexes with the markers, and one-dimensional members of the decomposition correspond to molecular properties. It is then possible to obtain pure spectra for the substances in the mixture when only having a set of the sums of such spectra. Furthermore, the substances can be identified by matching each pure spectrum against a database of pure MR spectra or by some other method. Finally, the norm of each spectrum will refer to its relative concentration. If one substance in a mixture is known for example, a solvent that is used for dissolving this mixture then by scaling its absolute concentration to the computed relative concentration, we will obtain an absolute concentration for all substances in the mixture. The spectrum of a marker and its absolute concentration can be also used to transform computed relative concentrations into absolute concentrations.

There are many possible properties that can scale a pure spectrum, some of which are listed below:
  marker concentration,
  marker chemical composition,
  the type of MR excitation sequence,
  the type of non-zero-spin isotope used for excitation,
  the type of non-zero-spin isotope used for spectrum detection,
  the spatial location of the MR transmitter,
  the spatial location of the MR receiver,
  the magnetic field intensity,
  the location of the mixture as determined by the external flow and its physical and chemical properties, and
  spatial separation of the mixture into components as a result of sorption.

In addition, some entries in this three or more dimensional structure may be not measured, or may be lost during measurement. In this case, a so-called sparse tensor is formed:

$$a_{n_1, \ldots, n_K} \omega_{n_1, \ldots, n_K} \simeq \omega_{n_1, \ldots, n_K} \sum_{r=1}^{R} b_{r,n_1}^{(1)} \times \ldots \times b_{r,n_K}^{(K)},$$

where $w_{n_1}, \ldots, n_K \geq 0$ and some $w_{n_1}, \ldots n_K$ are zero. Methods for the effective numerical solution of this approximation have been suggested by Ibragimov, published in NLAA in 2001.

The use of many different markers and/or different concentrations of the same markers will improve the overall performance/speed/accuracy of the system, but may be more expensive in terms of production. It is possible to use as markers standard chromatography sorbents like silica gel, diamond, aluminum oxide, zirconium oxide, or a metal oxide impregnated with $-(CH_2)_n-CH_3$, n=1, ..., 24, $-CN$, $-NH_2$, $-NO_2$, $-(C_6H_4)-NO_2$, as well as many other materials. Here we have less requirement for consistent production quality of markers than is necessary in chromatography chromatography sorbents should be very similar in order to obtain similar retention times, but in MR detection, we only require similar molecule orientations. The marker itself may consist of isomer molecules, or also stereo-isomer molecules, to achieve selectivity in the orientations of stereo-isomers or chiral molecules.

The diamond crystals doped with 11B, 14N, 15N or any other non-zero-spin isotopes, further impregnated with $-(CH_2)_n-CH_3$, n=1, ..., 24, $-CN$, $-NH_2$, $-NO_2$, $-(C_6H_4)-NO_2$, as well as many other materials, make additional advantage in combination of NMR optical detector with markers that require only molecule orientations.

In many cases, a plurality of MR spectra is obtained in a volume defined by or including a surface bearing one or more of the markers. The surface may form one or more tubes, may form one or more plates, may be flat or curved, or may have any other arbitrary shape.

Additionally, we are able to use a large variety of isotopes to excite MR spectra as well as different isotopes to detect the response, and to use different magnetic field strengths in order to obtain different response types.

Non-zero-spin particles within the volume are excited by one or more MR transmitters with different spatial intensities, or the spatially non-uniform responses of non-zero-spin particles within the volume are received by one or more MR receivers located within and/or near the volume.

Excited isotopes may be situated in markers or in substances in a mixture, and isotopes that generate MR spectra may be situated in the same molecule or in the molecule with which a molecule containing an excited isotope is interacting. If marker molecules and substances in the mixture have similar fragments, the use of additionally enriched isotopes like 2H, 13C, 15N, 17O, 25Mg, 29Si, or 43Ca will help to better differentiate the MR spectra. The intensity of transmitted energy for isotope excitation may be intentionally organized so high that the emitting MR response interferes with the excitation wave, producing local heat that may additionally be used to affect molecular properties.

A distribution of markers across several regions with different relative concentrations will help in obtaining different spectral intensities for each particular component, and also will help provide better data approximation.

For the manufacture of a system in which the markers are located in the volume, it may be necessary to create significant pressure to introduce and place these markers inside this volume. On the other hand, it is desirable to have a minimum wall thickness so that nonzero-spin isotopes of the walls do not participate in the absorption and emission of the MR spectra. To solve this problem, we suggest placing additional removable walls that would withstand higher pressure, only to fill the system with markers, and then remove such walls before starting measurements.

A flowing fluid additionally forwarded into the volume containing markers and the investigated mixture, which can be varied in terms of its chemical composition, flow speed, direction, and physical parameters, generates additional variations in spectra and, as a result, thereby generates dimensions in said multi-dimensional tensor, improving approximation quality and the accuracy of computed pure spectra.

Hence, this approach opens new possibilities for detecting similar components that are difficult to decompose by chromatography methods, which makes this method universal for black box chemical composition detection without a priori knowledge.

Method for Estimation of Droplet Size Distribution

It is very often the situation that an investigated mixture has different phases, droplets, particles, or large molecules, and it is important to determine information about these components and their distribution. In this case, one can use a tube a2 without stationary phase, or with stationary phase that does not react chemically with the mixture.

Consider a mixture of two phases of chemicals (FIG. 19), for example oil and water, and assume that pure spectra are known for each phase. The spectrum of the mixture represents a linear combination of the spectra of the pure phases (oil and water in the example), and the weights of that linear combination refer to the relative proportions of these phases in the mixture.

If there is an isotope's type that is represented in one phase but has no presence in the second (for example, carbon is available in the oil but has no presence in water), excitation by this type of non-zero-spin nucleus will excite only matching nuclei (carbons d1-d2 in the example). The spin energy from these excited nuclei d5 (carbons) will also excite other nuclei that are situated nearby, inside the same phase, and also at the surface between phases d7 (for example, hydrogens in the water phase on the surface close to oil). By measuring the spectra of these different, simultaneously excited nuclei (hydrogen d4, d6 and carbon d2), one can determine how much energy was transferred from one type to another d7 and calculate the total size of the surface between phases. If the droplets have spherical shapes (and normally they do), the droplet size distribution can be computed by a simple relational formula.

The same approach is applicable for determining:
the droplet size distribution of oil and its products,
the droplet size distribution of milk and its products,
the count per volume of leukocytes and/or erythrocytes in a blood sample,
the count per volume of bacteria and/or viruses in a liquid sample,
the count per volume of particles in engine lubricant and motor oil, and
the count of any other droplets or particle-size distributions in any fluid mixture.

Solid-State NMR

Usage of several receiving coils pointed in different directions, with all axes of these coils situated in the plane that is perpendicular to the permanent magnetic field as shown in FIG. 12, opens new horizons for making solid-state NMR possible without highly intensive rotation of the measured substance. If the solid-state material to be measured is placed into a tube, and this tube is filled with said material to a length that is several times larger than the tube's diameter, one can push and pull the tube through the coils assembly (FIG. 12) and measure all responses from the receiver coils. If appropriate algorithms are used, as was described in the section "ELEGANT NMR" of this patent application, one can get highly accurate results without intensive rotation of this tube around its axis, because responses from differently pointed receiving coils allow for even better signal averaging than does the high-speed rotation at 100,000 rpm that is nowadays used in many solid-state NMR systems.

This advantage opens the possibility of constructing a portable NMR spectrometer based on FIG. 13, with the variant of FIG. 13C such that the tube with solid-state material for the measurement is placed into connectors a22 and may be slightly rotated and push-pulled during measurements. This variant construction allows arbitrary solid-state NMR measurements with a portable device even in field conditions.

Another embodiment for solid-state NMR is based on the construction described in FIG. 17, wherein one or several ELMATHRONs may be used and the tube with measured material may be installed into capillary a2. Alternatively, this capillary may be absent, but all coils a6 are nonetheless situated as if the capillary is present, and said tube is placed, rotated, and push-pulled in the position indicated by the label a2 in this drawing (FIG. 17).

This embodiment is not limited to the measurement of solid-state matter, and may be used for any homogeneous or heterogeneous material that can be situated inside said tube.

MR. NIB

Magnetic Resonance Non-Invasive Blade and Magnetic Resonance Non-Invasive Beam (MR. NIB) is the proposed method of this patent application for non-invasive tissue ablation using heat generated by NMR and/or DNP-NMR without the need to invade the body with probe(s). It employs a non-uniform permanent magnetic field (NUPMF) n6 (FIG. 20) with an appropriately sized gradient of magnetic field inside the patient's body.

The interaction of a permanent magnetic field and an alternate magnetic field (AMF) without DNP and/or without magnetic field focusing is well known, but never used for ablation or heating of tissues because the method has poor spatial accuracy. This poor spatial accuracy results from to the low frequency waves involved in AMF (100 MHz and less), which are several meters in length and cannot be accurately focused on the intersection of the permanent magnetic field and AMF.

MR. NIB will direct the NMR device to generate a NUPMF of predetermined shape n6 via several permanent or superconductor magnets n1 including the magnets proposed above to focus NUPMF; the movements of these magnets are controlled in real time from the MR.

NIB computer appliance. Movement of the magnets provides a coarse magnetic field shape; fine tuning/adjustment is performed by adjusting the (gradient) coils.

The fact that a permanent magnet assembly with focused permanent magnetic field produces a high intensity magnetic field only over a region of small size additionally improves the safety of this system regarding possible accidents with magnetic parts during surgical operation and treatment.

Perpendicular to, or at least non-parallel to, the direction of the NUPMF, one or several transmitters of microwaves of Larmor electron frequency with amplitude modulated AMF are controlled by block n5 to support mechanical movement in real time. The AMF is generated with a predetermined sequence of pulses in order to ensure that it will contain one or several mixtures of predetermined frequencies. To ensure that the focal point of the ablation is targeted to the tumor and/or ablated tissue, and/or tissue for heating, the shape and focal point n7 of the alternate field can be changed in real time.

In addition, the physical position of the focal point n7 may be moved by means of the mechanical movement of magnets and alternate magnetic field (AMF) transmitters, or by means of altering the intensities of permanent magnets using adjacent coils. This allows the focal point n7 to be forwarded on a distribution of medicaments, pharmaceuticals, or means with predetermined non-zero-spin nuclei that are injected and/or ingested by the patient and then physically distributed through tissues. As the injected and/or ingested medicaments, pharmaceuticals or means may migrate during treatment, the focal point n7 is moved in order to follow their actual position.

The patient body that is the object of the surgical procedure must be able to be physically situated within the physical MR. NIB components. Accordingly, a physical constraint that must be addressed in the construction of hardware is the need to ensure sufficient separation between magnets/transmitters and the patient's body, so that they do not cause discomfort to the patient during the treatment.

The key differences of this proposed non-invasive heating method are in its usage of a non-uniform permanent magnetic field that is focused only on the region intended for ablation/heating and/or the usage of dual band DNP-NMR systems as proposed above regarding ELMATHRONs.

As discussed previously, MR. NIB represents a fully non-invasive method of heating and/or activation of pharmaceuticals for internal organs in human bodies. This property supports the surgeon in the performance of surgical operations using NMR energy without making any cuts in the body. Hence, an accurate monitoring and visualization process is required for accurate guidance of the non-invasive, electronic "surgical scalpel." If used with a real-time database method (Algorithm Nr 2 of this patent application), MR. NIB provides an electronic and/or human surgeon with that necessary real-time visualization, which can be leveraged to provide fully automatic, semi-automatic, or fully manual control over the surgical procedure.

The key difference in the proposed visualization approach from traditional methods is the use of the real-time method discussed in the section "real-time method of signals from repeating processing method," which supports the creation and storage of an a priori interactive map of the target surgical zone.

In the case where any receiver's response n2 does not match a previously collected response and its corresponding image, this method will automatically and immediately switch the energy generation system off for one or more time periods until synchronization of the receiver's responses to pre-stored images is achieved. Automatically turning off the heating energy in this manner is necessary to ensure that the position where the magnetic resonance "blade/scalpel" function is being applied is definitively established, and will avoid tissue destruction occurring external to the target region. In parallel, a new image will be computed for this new sensor data set and used to update the database.

This electronic scalpel/blade can be automatically switched off in a few milliseconds and is controlled by dedicated computing resources. The MR. NIB method controls imaging and scalpel/heating operation at the same time without any impact to other functions. If desired, the guidance capability can be configured to use programmatic control of the targeting functions, thereby supporting a fully automatic ablation procedure.

Hence, the implementation of the MR. NIB method for guidance is comprised of the following steps:

The method integrates several mechanically-controlled receiving antennas (n2 and n3) and requisite computing appliances to perform deterministic matching and inverse solution of MRI calculations according to Algorithm Nr. 1. These components utilize an inverse Maxwell equation solver for the generation of a visualization to support a surgeon's visualization of the procedure and automatic/semiautomatic guidance of the non-invasive blade.

An a priori database is constructed for an individual patient according to Algorithm Nr. 2 through a short (several minutes) mapping session prior to performance of the surgical scalpel procedure. Data collected, computed, and stored here for the intended ablation session provides recallable information on every possible location of the target tumor, including effects and movement from patient activity such as breathing. The volume of data to be available for instant recall from conventional NMR and/or MRI sensors is several dozen gigabytes per second, or approximately 200 Tb in total for a two-hour ablation session.

The proposed real-time method, together with signal processing methods described in FIGS. 1-2, compresses this data to a few gigabytes of matrix factors, including a computational database made for every possible magnet/adjusting coil/frequency combination, and makes it possible to perform the guidance in real time and to drastically reduce hardware expenses.

An important feature of the MR. NIB approach lies in the fact that its guiding function may also be applied with other ablation methods such as HIFU.

APPENDIX 1. ALGORITHM FOR SOLUTION OF (f12)

The minimization function in problem (f12) is independent on the t variable, hence it is sufficient to solve:

$$\min_{x,y} \sum_{j=1}^{J} \|A_j - y(q_j + x) *\|_2^2,$$

where $x \in \mathbb{C}^N$ and $y \in \mathbb{C}^I$ are unknowns that refer to $\psi_n(t)$ and $\varepsilon_i(t)$, $A_j \in \mathbb{C}^{I \times N}$ $\{a_{inj}\}$ refers to $\tilde{\psi} z_{inj}(t)$, $q_j \in \mathbb{C}^N$ refers to $\hat{\psi}_{nj}(t)$ for each given t. The following objects should be computed step-by-step:

$$P = \sum_{j=1}^{J} A_j,$$

then compute the SVD of $P = UDV^*$, $U \in \mathbb{C}^{I \times R}$, $U^*U = I$, $V \in \mathbb{C}^{N \times R}$, $V^*V = I$, $D = \text{diag}(d)$, $\in \mathbb{R}^{R \times R}$ $d = (d_1, \ldots, d_R)^T$, $d_1 \geq \ldots \geq d_R$, $R = \min(I,N)$ and afterwards compute $$a = \sum_{j=1}^{J} \|q_j\|_2^2, \quad b = V * \sum_{j=1}^{J} q_j = (b_1, \ldots, b_R)^T,$$

$$c = U * \sum_{j=1}^{J} A_j q_j = (c_1, \ldots, c_R)^T.$$

Find by the bisection method a root of $$Ja - \|b\|_2^2 = \sum_r \frac{|Jc_r - b_r d_r|^2}{\gamma J - d_r^2}$$

by the variable in an open interval $\gamma > d_1^2/J$ with the upper bound taken as the computer precision and compute $$\forall r = 1, \ldots, R: z_r = \frac{\gamma b_r - d_r c_r}{d_r^2 - J\gamma}, \quad x = V_z, \quad y = \gamma \|Dz + c\|_2^2 (Px + Uc).$$

There are many special cases, for example if one or several isotopes are missing in the investigated substances. In the case where only two input coils are considered (J=2) and the first coil reads reference spectra only, the solution reads as: $y = A_1 q_1 / \|q_1\|_2^2$, $$x = \frac{\|q_1\|_2^2}{\|A_1 q_1\|_2^2} A_2^* A_1 q_1 - q_2.$$

The invention claimed is:

1. A method for detecting at least one chemical substance and its concentration in a mixture using magnetic resonance, the method comprising:
   placing the mixture in contact with at least one marker;
   obtaining a plurality of magnetic resonance spectra that represent the mixture in combination with the markers;
   analyzing the plurality of magnetic resonance spectra so as to recognize the substances and their concentrations;
   wherein the marker is a substance that through intermolecular interactions causes a predetermined orientation of molecules for at least one of the mixture components.

2. The method of claim 1, wherein the intermolecular interactions refer to Van der Waals interactions.

3. The method of claim 1, wherein the intermolecular interactions refer to reversible chemical transformations.

4. The method of claim 1, wherein the intermolecular interactions between the marker and any of the substances in the mixture result in a difference in Gibbs free energy less than that required to perform a sorption-based chromatography separation.

5. The method of claim 1, wherein the plurality of magnetic resonance spectra is obtained simultaneously using plural magnetic resonance detectors.

6. The method of claim 1, wherein the plurality of magnetic resonance spectra is obtained subsequently using at least one magnetic resonance detector.

7. The method of claim 1, wherein the magnetic resonance spectra refer to nuclear magnetic resonance spectra.

8. The method of claim 1, wherein the magnetic resonance spectra refer to electron spin resonance spectra.

9. The method of claim 1, wherein the plurality of magnetic resonance spectra is obtained using a plurality of markers.

10. The method of claim 1, wherein the plurality of magnetic resonance spectra is obtained using different concentrations of at least one marker.

11. The method of claim 1, wherein the plurality of magnetic resonance spectra is obtained using different excitations of non-zero-spin particles in the markers or the substances in the mixture.

12. The method of claim 1, wherein the plurality of magnetic resonance spectra is obtained with at least one known substance presents in the mixture, wherein each of the known substances has a known magnetic resonance spectrum or a known concentration.

13. The method of claim 1, wherein magnetic resonance excitation of molecules of the markers and the substances in the mixture is provided by a two-band microwave transmitter with one band referring to Larmor frequency of electrons and the other band referring to Larmor frequency of non-zero-spin nuclei.

14. The method of claim 1, wherein molecules of the markers and the substances in the mixture are distributed across a plurality of regions having different magnetic field strengths.

15. The method of claim 1, additionally comprising at least one permanent magnetic field source, wherein the permanent magnetic field source is built with at least one permanent magnet having a non-uniform magnetization, so that the intensity of the permanent magnetic field achieved at said point is higher than the magnetic field intensity achievable when using the same magnet material with uniform magnetization.

16. The method of claim 1, wherein at least one marker is comprised of a predetermined ratio of isomers.

17. The method of claim 1, wherein at least one marker is comprised of a predetermined ratio of chiral isomers.

18. The method of claim 1, wherein at least one marker is comprised of porous substances or materials.

19. The method of claim 1, wherein at least one of the magnetic resonance detectors comprises a receiver coil.

20. The method of claim 1, wherein at least one of the magnetic resonance detectors comprises an optical sensor.

21. The method of claim 1, wherein the plurality of magnetic resonance spectra is obtained in a volume defined by or including a surface bearing at least one marker.

22. The method of claim 21, wherein non-zero-spin particles within the volume are excited by at least one magnetic resonance transmitter with different spatial intensities.

23. The method of claim 21, wherein spatially non-uniform responses of non-zero-spin particles within the volume are received by at least one magnetic resonance receiver located within the volume.

24. The method of claim 21, wherein spatially non-uniform responses of non-zero-spin particles within the volume are received by at least one magnetic resonance receiver surrounding the volume.

25. The method of claim 21, wherein the surface is defined by at least one tube.

26. The method of claim 21, wherein the surface is defined by at least one plate.

27. The method of claim 21, wherein the volume is mechanically moved so that the mixture remains near the magnetic resonance detectors.

28. The method of claim 21, wherein the marker contains a predetermined non-zero-spin isotope that can be excited by a high-intensity magnetic resonance transmitter so as to cause heating of the marker and its surrounding medium.

29. The method of claim 21, wherein the mixture is separated into independent groups of substances due to the intermolecular interactions.

30. The method of claim 21, further including an electrical current cased in the volume.

31. The method of claim 21, wherein a source of one magnetic resonance spectrum among the plurality of spectra is located between a plurality of magnetic resonance detectors, and the magnetic resonance spectrum obtained is based on a combination of signals from the magnetic resonance detectors.

32. The method of claim 21, wherein distribution of the substances within the volume is controlled by means of a flow of a fluid of known chemical composition.

33. The method of claim 32, wherein speed and direction of the flow are controlled over time.

34. The method of claim 32, wherein the known chemical composition is controlled over time.

35. The method of claim 32, wherein physical parameters of the flow are controlled over time.

36. The method of claim 1, wherein variations of the magnetic resonance spectra of marker-substance pairs form at least three dimensional structure $a_{n_1}, \ldots, n_K \in \mathbb{R}^{N_1 \times N_K}$, in which the first dimension $n_1 = 1, \ldots, N_1$ corresponds to an associated magnetic resonance spectrum and the other dimensions correspond to variations in properties of the marker and the substance, and the method comprises approximating the three or more dimensional structure by a tensor decomposition $$a_{n_1,\ldots,n_K} \simeq \sum_{r=1}^{R} b_{r,n_1}^{(1)} \times \ldots \times b_{r,n_K}^{(K)},$$

so that a one-dimensional member of the decomposition of the first dimension $b_{r,n_1}^{(1)}$ corresponds to a set of spectra from R substances and their intermolecular complexes with the markers, and other one-dimensional members of the decomposition correspond to the varied properties.

37. The method of claim 36, wherein an magnetic resonance spectrum is not obtained for at least one entry of varied property, so that the three or more dimensional structure forms a sparse tensor:

$$a_{n_1,\ldots,n_K} \omega_{n_1,\ldots,n_K} \simeq \omega_{n_1,\ldots,n_K} \sum_{r=1}^{R} b_{r,n_1}^{(1)} \times \ldots \times b_{r,n_K}^{(K)},$$

where $\omega_{n_1}, \ldots, n_K \geq 0$ and at least one $\omega_{n_1}, \ldots, n_K$ is zero.

38. The method of claim 36, wherein at least one of the one-dimensional member of the decomposition corresponds to a variation in one of the following properties:
marker concentration,
marker chemical composition,
type of magnetic resonance excitation sequence,
type of non-zero-spin isotope used for excitation,
type of non-zero-spin isotope used for spectrum detection,
spatial location of the magnetic resonance transmitter,
spatial location of the magnetic resonance receiver,
magnetic field intensity,
location of the mixture as determined by the external flow and its physical and chemical properties, or
spatial separation of the mixture into components as a result of sorption.

39. The method of claim 1, wherein at least one marker contains at least one chemical element enriched with its non-zero-spin isotope.

40. The method of claim 1, wherein at least one marker contains a chemical group of atoms from the set of: $-(CH_2)_n-CH_3$, n=1, ..., 24, $-CN$, $-NH_2$, $-NO_2$, $-(C_6H_4)-NO_2$.

41. The method of claim 1, wherein at least one marker contains diamond particles dopped with non-zero-spin isotope.

* * * * *